United States Patent
Hess et al.

(10) Patent No.: US 11,490,815 B2
(45) Date of Patent: Nov. 8, 2022

(54) METHODS FOR EXTRACTING SUBJECT MOTION FROM MULTI-TRANSMIT ELECTRICAL COUPLING IN IMAGING OF THE SUBJECT

(71) Applicant: Oxford University Innovation Limited, Oxford (GB)

(72) Inventors: Aaron Hess, Oxford (GB); Matthew Robson, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 393 days.

(21) Appl. No.: 16/497,079

(22) PCT Filed: Mar. 24, 2018

(86) PCT No.: PCT/IB2018/052014
§ 371 (c)(1),
(2) Date: Sep. 24, 2019

(87) PCT Pub. No.: WO2018/173009
PCT Pub. Date: Sep. 27, 2018

(65) Prior Publication Data
US 2020/0375463 A1 Dec. 3, 2020

Related U.S. Application Data

(60) Provisional application No. 62/476,250, filed on Mar. 24, 2017.

(51) Int. Cl.
*A61B 5/00* (2006.01)
*A61B 5/055* (2006.01)
(Continued)

(52) U.S. Cl.
CPC ............ *A61B 5/0044* (2013.01); *A61B 5/055* (2013.01); *A61B 5/7207* (2013.01);
(Continued)

(58) Field of Classification Search
CPC ......... A61B 8/463; A61B 8/06; A61B 8/4427; A61B 8/5261; A61B 8/4416; A61B 8/467; A61B 8/5238
See application file for complete search history.

(56) References Cited

U.S. PATENT DOCUMENTS 9,864,021 B1* 1/2018 Habara ............... G01R 33/288
2004/0212363 A1* 10/2004 Epstein ................. G06N 10/00
324/309

(Continued)

*Primary Examiner* — Bo Joseph Peng
(74) *Attorney, Agent, or Firm* — Thomas|Horstemeyer, LLP

(57) ABSTRACT

Described herein are methods and systems for extracting or determining subject motion from multi-channel electrical coupling in imaging of the subject, in particular in magnetic resonance (MR) imaging of the subject. The motion can be of a region of interest of the subject (such as an organ or specific tissue). Changes in the position of the subject and the subjects organs can be monitored by measuring how external coils, such as RF coils, couple to the subject and to one another and change the scattering of the RF coils, for example scattering of RF pulses transmitted by the coils. Changes in position influence this coupling and the scattering and can be detrimental to the quality of the imaging The present methods and systems address and overcome this problem.

18 Claims, 43 Drawing Sheets

(51) Int. Cl.
*G01R 33/56* (2006.01)
*G01R 33/567* (2006.01)
*G01R 33/58* (2006.01)

(52) U.S. Cl.
CPC .......... *A61B 5/7278* (2013.01); *A61B 5/7289* (2013.01); *G01R 33/5608* (2013.01); *G01R 33/5676* (2013.01); *G01R 33/583* (2013.01)

(56) References Cited

U.S. PATENT DOCUMENTS

| | | | | |
|---|---|---|---|---|
| 2006/0125475 | A1* | 6/2006 | Sodickson | A61B 5/0536 600/416 |
| 2009/0076377 | A1* | 3/2009 | Findekelee | G01R 33/365 600/422 |
| 2014/0139218 | A1* | 5/2014 | Findeklee | G01R 33/3628 324/318 |

\* cited by examiner

| Subject ID | Breathing | # of Heart Beats | Feature 4 (Diastasis) | | Feature 5 (Atrial Systole) | | Feature 6 (Atrial Systole) | | Feature 7 (R-wave) | | ECG | |
|---|---|---|---|---|---|---|---|---|---|---|---|---|
| | | | Se [%] | PPV[%] | Se [%] | PPV[%] | Se [%] | PPV[%] | Se [%] | PPV[%] | Se [%] | PPV[%] |
| 1 | Breath hold | 57 | 100.0 | 100.0 | 100.0 | 100.0 | 100.0 | 100.0 | 100.0 | 100.0 | 100.0 | 100.0 |
| | Free-Breathing | 96 | 99.0 | 100.0 | 91.7 | 100.0 | 86.5 | 100.0 | 97.9 | 100.0 | 100.0 | 100.0 |
| 3 | Breath hold | 48 | 100.0 | 100.0 | 100.0 | 100.0 | 85.4 | 93.2 | 100.0 | 100.0 | 100.0 | 100.0 |
| | Free-Breathing | 87 | 100.0 | 96.7 | 98.9 | 98.9 | 90.8 | 94.0 | 100.0 | 100.0 | 100.0 | 100.0 |
| 4 | Breath hold | 52 | 100.0 | 100.0 | 100.0 | 100.0 | 100.0 | 100.0 | 100.0 | 100.0 | 100.0 | 100.0 |
| | Free-Breathing | 96 | 100.0 | 100.0 | 95.8 | 100.0 | 100.0 | 99.0 | 100.0 | 100.0 | 100.0 | 100.0 |
| 5 | Breath hold | 23 | 100.0 | 100.0 | 100.0 | 100.0 | 100.0 | 79.3 | 100.0 | 100.0 | 100.0 | 100.0 |
| | Free-Breathing | 40 | 100.0 | 100.0 | 100.0 | 100.0 | 100.0 | 78.4 | 100.0 | 100.0 | 100.0 | 100.0 |
| 6 | Breath hold | 29 | 89.7 | 100.0 | 89.7 | 100.0 | 89.7 | 100.0 | 100.0 | 100.00 | 100.0 | 100.0 |
| | Free-Breathing | 51 | 86.3 | 97.8 | 84.3 | 100.0 | 92.2 | 97.9 | 100.0 | 100.00 | 54.9 | 100.0 |
| Total | | 579 | | | | | | | | | | |
| Mean | | | 96.5 | 98.6 | 96.0 | 99.9 | 94.4 | 94.2 | 99.8 | 100.0 | 96.1 | 100.0 |

FIG. 4

| Subject | Mean ±SD (mm) Unfiltered | Total drift (mm) |
|---|---|---|
| 1 | 0.0 ± 1.2 | 0.7 |
| 2 | -3.7 ± 13.9 | -79.8 |
| 3 | -0.1 ± 1.3 | 4.2 |
| 4 | -0.3 ± 1.4 | -2.7 |
| 5 | 0.1 ± 0.8 | 1.9 |

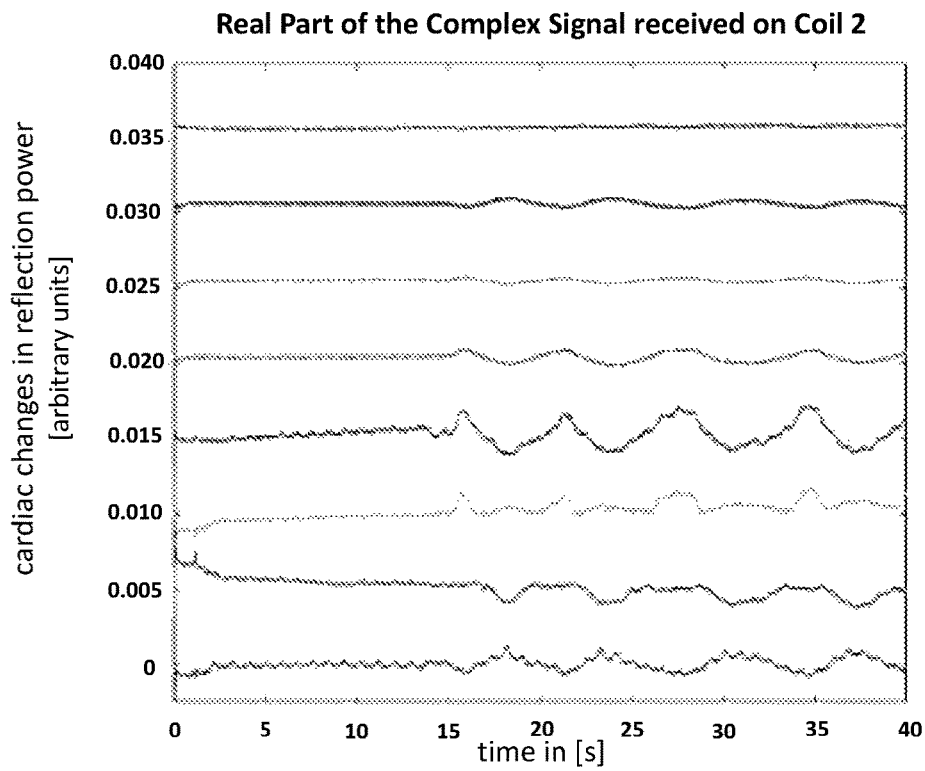
FIG. 29A1
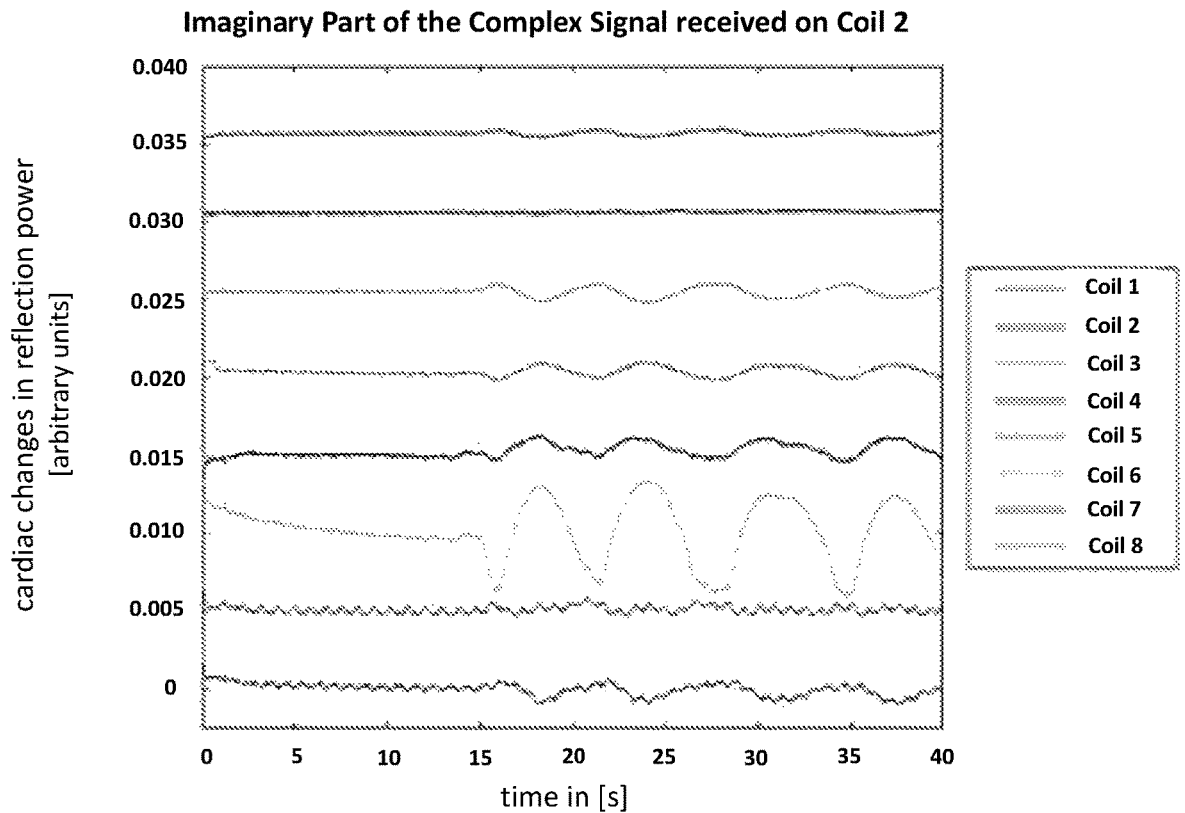
FIG. 29A2

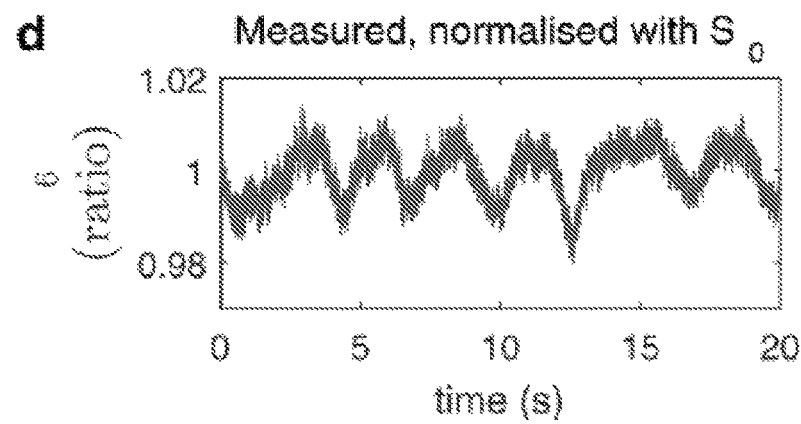
FIG. 36D
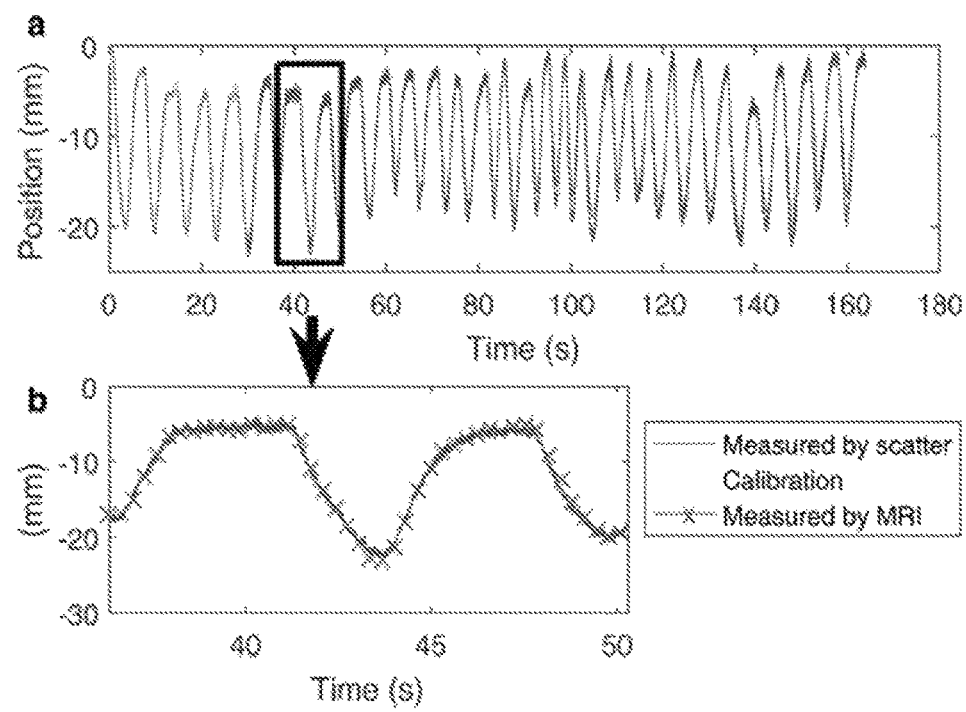
FIG. 37A
FIG. 37B

METHODS FOR EXTRACTING SUBJECT MOTION FROM MULTI-TRANSMIT ELECTRICAL COUPLING IN IMAGING OF THE SUBJECT

CROSS-REFERENCE TO RELATED APPLICATIONS

This application is the National Stage of International Application No. PCT/IB2018/052014, filed Mar. 24, 2018, which claims the priority to U.S. Provisional Application No. 62/476,250, filed Mar. 24, 2017, which are entirely incorporated herein by reference.

TECHNICAL FIELD

The present disclosure generally relates to methods for extracting or determining patient motion from multi-transmit electrical scattering, in particular in magnetic resonance imaging.

BACKGROUND

Magnetic resonance (MR) imaging (MRI) is a common non-invasive imaging modality useful for structural and functional imaging of living subjects. Subjects to be imaged (or scanned) are placed in or adjacent to a scanner, a magnetic field is applied, and one or more radio frequency (RF) pulses are generated that excited and align proton spins. Following the RF pulse(s), protons relax, generating RF emissions that are detected by receivers in the scanner, and an image is generated.

MRI quality is particularly subject to voluntary and involuntary motion of a subject in a scanner. Subject motion can create artefacts and issues with image reconstruction, and given the cost and length of MR procedures, subject motion is not desirable. While minimizing voluntary motion is relatively straightforward, involuntary motion is not. Two main sources of involuntary motion in a subject are the movement of the diaphragm during respiration and the movement of the heart during cardiac cycles. Breath holding is the common method used to minimize involuntary motion of a subject during MRI. Breath holding to minimize diaphragm movement, however, limits scan time (at most 15 seconds in most cases). Controlling for cardiac motion during cardiac cycles requires external hardware, which can be complex (requiring additional technicians) and can slip out of place during a scan.

Accordingly, there is a need to address the aforementioned deficiencies and inadequacies. New methods and systems to minimize motion during MR scanning and improve MRI quality are desired.

SUMMARY

The present disclosure is directed to improving imaging quality for example, medical imaging quality. In various aspects, a method is provided to monitor changes in the position of a subject's (for example, a patient's) organs by measuring how external RF coils couple to the subject and to one another during imaging, Changes in position influence this coupling and are reflected in the scattering of the network of coils, By measuring the scattering whilst also collecting images, for example rapid MRI images, mappings can be generated that describe subject motion as a function of the scattering. Subsequently the scattering measurements can be used on their own to accurately predict the position of the subject. Effects of drift in the scattering that are not due to patient motion can be monitored and compensated by additional infrequent image data. The subject motion can be used to correct for and obtain better image quality either by using this information to change the timing (gating) of the image acquisition and/or to change the image reconstruction. Motions that can be corrected include breathing, cardiac, and involuntary motions (i.e. coughing, sneezing, twitching, swallowing, head movements, limb movements, etc.). In various aspects, the present disclosure can be used to improve magnetic resonance (MR) image quality.

The present method also makes for faster patient set-up, safer patient environment (no RF burns from ECG equipment for example), and reduced cost. Further the approach can monitor more independent characteristics of motion, for example, than with ECG and respiration monitoring that are limited to 2 degrees of freedom that are detected. With coil coupling and a multi-channel system there are more parameters that can be detected which provides a more detailed measurement of the patient. For example, with an eight channel system there are 64 complex scattering parameters that can be detected. Further the coil scattering approach provides information at a temporal resolution of the RF pulses, which for a rapid steady state free procession (SSFP) sequence can be around 3 ms temporal resolution.

The present multiple channel approach can utilize imaging data to convert the dynamic scattering parameters into useful motion parameters. This combined imaging and scattering solution and the associated methods provides a solution that will work in all subjects and can be readily translated onto clinical MRI scanners.

The changes in the electrical scattering are due to movement of the conductive components of the human body. As the subject breathes or its heart beats the conductive tissues move around. The RF coils on or adjacent the surface of the body of the subject (which may be already present and used for imaging in other ways) will then couple to each other and the subject in a different way. The scanner (for example a 7T scanner) may already contain hardware capable of sensing the forward and reflected power or voltage from these cods, and this can be used to dynamically determine the scattering between the RF coils and the motion.

In an embodiment, a method for extraction of subject motion from multi-transmit electrical coupling in imaging of the subject is provided. The method can comprise positioning a subject in association with a scanner, wherein the scanner has one or more transmit coils; starting one or more MR imaging pulse sequences, wherein the one or more MR imaging pulse sequences comprise a plurality of RF pulses; collecting one or more S-matrix measurements over a period of time using the scanner, wherein the measurements are based on the reflected power of the plurality of RF pulses; performing a calibration on the one or more S-matrix measurements to determine a mixing vector and a constant; determining a reflection coefficient from the one or more calibrated S-matrix measurements; forming a measurement vector from the reflection coefficient; determining a position of an anatomical structure of the subject using the measuring vector, mixing vector, and constant: and outputting the determined position of the anatomical structure of the subject. In an aspect, the starting of the one or more MR imaging pulse sequences can further comprise diaphragm navigator imaging with the scanner. The diaphragm navigator imaging can be carried out simultaneously with the starting of the MR imaging pulse sequences.

In an embodiment, the method can comprise positioning a subject in association with a scanner, wherein the scanner has one or more transmit coils; activating one or more MR imaging pulses comprising a plurality of RF pulses; collecting a plurality of scattering matrix (S-matrix) measurements over a period of time using the scanner to create a time series of S-matrix measurements, wherein the plurality of S-matrix measurements are based on the reflected power of the plurality of RF pulses; splitting the time series of S-matrix measurements into real and imaginary components to form split S-matrix measurements: processing the split S-matrix measurements; extracting and identifying a raw cardiac signal of the subject from the processed split S-matrix measurements; determining a mixing vector from the raw cardiac signal; establishing a signal from the mixing vector; analyzing the signal from the mixing vector; detecting features of a cardiac cycle from the analyzed signal; and correlating the detected cardiac cycle features with cardiac motion of the subject.

In an embodiment, a system is provided. The system can provide for extraction of subjection motion from multi-transmit coupling in imaging of the subject. The system can comprise; a magnetic resonance (MR) scanner including one or more transmit coils; at least one computing device having a processor and a memory; and at least one application executable in the at least one computing device stored in the memory of the computing device. When executed by the at least one computing device, the application can cause the at least one computing device to: start one or more MR imaging pulse sequences with the scanner, wherein the one or more MR imaging pulse sequences comprise a plurality of RF pulses; collect one or more S-matrix measurements over a period of time using the scanner, wherein the measurements are based on the reflected power of the plurality of the RF pulses; perform a calibration on the one or more S-matrix measurements to determine a mixing vector and a constant; determine a reflection coefficient from the one or more calibrated S-matrix measurements; form a measurement vector from the reflection coefficient; determine a position of an anatomical structure of the subject using the measuring vector, mixing vector, and constant; and output the determined position of the anatomical structure of the subject. The output can be to a visual display, such as a computer monitor, which can be a part of the computing device, scanner, or both. In an aspect, the application can further cause the at least one or more computing devices to start diaphragm navigator imaging with the scanner.

In any one or more aspects of any one or more of the embodiments the starting of the one or more MR imaging pulse sequences with the scanner can be starting using the one or more transmit coils, for example a plurality of RF transmit coils. The plurality of RF pulses can be part of a gradient echo (GRE) sequence, an inversion recovery sequence, or a balanced steady state free precession sequence, individually or in combination. The scanner can have a plurality of transmit coils and the pulses can be the same on each individual transmit coil of the plurality of transmit coils of the scanner. The scanner can have a plurality of transmit coils and a pulse on at least one individual transmit coil of the plurality of transmit coils can be different than the pulses on the other transmit coils of the plurality of transmit coils. The plurality of RF pulses can be frequency multiplexed pulses, parallel transmit spokes, or parallel transmit spirals, individually or in combination. The split S-matrix measurements can comprise demeaning, de-trending or filtering the split S-matrix measurements, individually or in combination. The extracting and identifying a raw cardiac signal from the processed split S-matrix measurements can comprise using an independent component analysis. Determining a mixing vector from the raw cardiac signal can comprise using a Welch power spectrum density estimation. The analyzing the signal from the mixing vector can comprise using a discrete wavelet transform. The scanner can be a magnetic resonance (MR) scanner for MR imaging of a region of interest of the subject. The one or more transmit coils can be a plurality of transmit coils. The transmit coils can be RF transmit coils that can transmit the RF pulses. The signal from the mixing vector can be a scalar signal.

Other systems, methods, features, and advantages of the present disclosure for extracting or determining subject motion from multi-transmit electrical coupling in imaging of the subject, will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 4 shows results for accuracy for feature detection on cardiac motion estimation using reflected power.

FIG. 12A shows the RF returned to channel 6 from all channels (i=1 to 8). FIG. 12B shows all RF originating from channel 6 returned to channels (j=1 to 8).

FIG. 25D shows the cardiac signal extracted using the S-matrix measurements of the same data

FIGS. 29A-29D. FIGS. 29A1 and 29A2 show an example of the raw power reflection on Coil 2 resulting from scattering and reflection from all coils (compare FIG. 29D) and the resulting cardiac trace extracted by the ICA. FIG. 29B is the full time course and FIG. 29C two selected peaks, Main peak shown is with feature 1 (green star). Diastasis detection by the violet diamond (feature 2), atrial contraction with red and blue crosses (feature 3 and 4 respectively) and feature 5 indicated by the black stars. Vertical red lines are ECG-trigger time points (R-peak).

FIG. 33A is a trace of diaphragm position measured by the new method and MRI, the first 30 s is used for calibration. FIG. 33B is an excerpt showing the higher temporal resolution of the method. FIG. 33C illustrates the difference between the two after up sampling the MRI measure to the same temporal resolution as the new method (from 320 ms sampling to 5 ms sampling of the RF pulses)

FIG. 35A is a recording of the absolute change in scattering with time for all components returned to channel 6, the sixth row of the scattering matrix S(t), the scale bar i 1:1000. FIG. 35B is the temporal average scattering matrix and FIG. 35C represents the temporal standard deviation. Note the mean scattering matrix can be more than 100 times larger than the temporal fluctuations, and fluctuations occur with a similar magnitude on the diagonal and off-diagonal elements. Note also the larger intracoil scattering for the anterior (1-4) and posterior (5-8) sets of coils.

FIGS. 36A-36D show the formation of $\Gamma_6(t)$ showing element 6 and the data that are plotted in FIGS. 35A-35C. FIG. 36A plots $\vec{v}^{ret,ideal}(t)$, element 6 of the product of S(t) and a constant vector to remove all amplifier effects. FIG. 36B plots $\vec{v}^{ret,measured}(t)$, which includes amplifier drift and amplifier noise. FIG. 36C is a plot of the effect of normalizing $\vec{v}^{ret,measured}(t)$ using $\upsilon_6^{fwd}$. FIG. 36D illustrates $\Gamma_6(t)$, which is the return normalized using $S_0$.

FIGS. 37A-37C represent a plot of estimated and measured diaphragm position (FIG. 37A). FIG. 37B is an extract from FIG. 37A showing the temporal resolution of the estimate compared with imaging, FIG. 37C shows the difference between the estimate and MRI at the RF pulse-sampling frequency.

FIG. 39B representing the inset of FIG. 39A). Details of the trabeculation in the right ventricle can be observed, and no observable respiratory artifact is present.

FIG. 40A shows a conductivity map of chosen slice with location of coil elements depicted. FIGS. 40B and 40C are real (FIG. 40B) and imaginary (FIG. 40C) sensitivity of the impedance between coil 3 and coil 2 of a TEM array centred over the heart, Shown are distinctly different patterns of sensitivity for real and imaginary components.

DETAILED DESCRIPTION

Figure 1A:
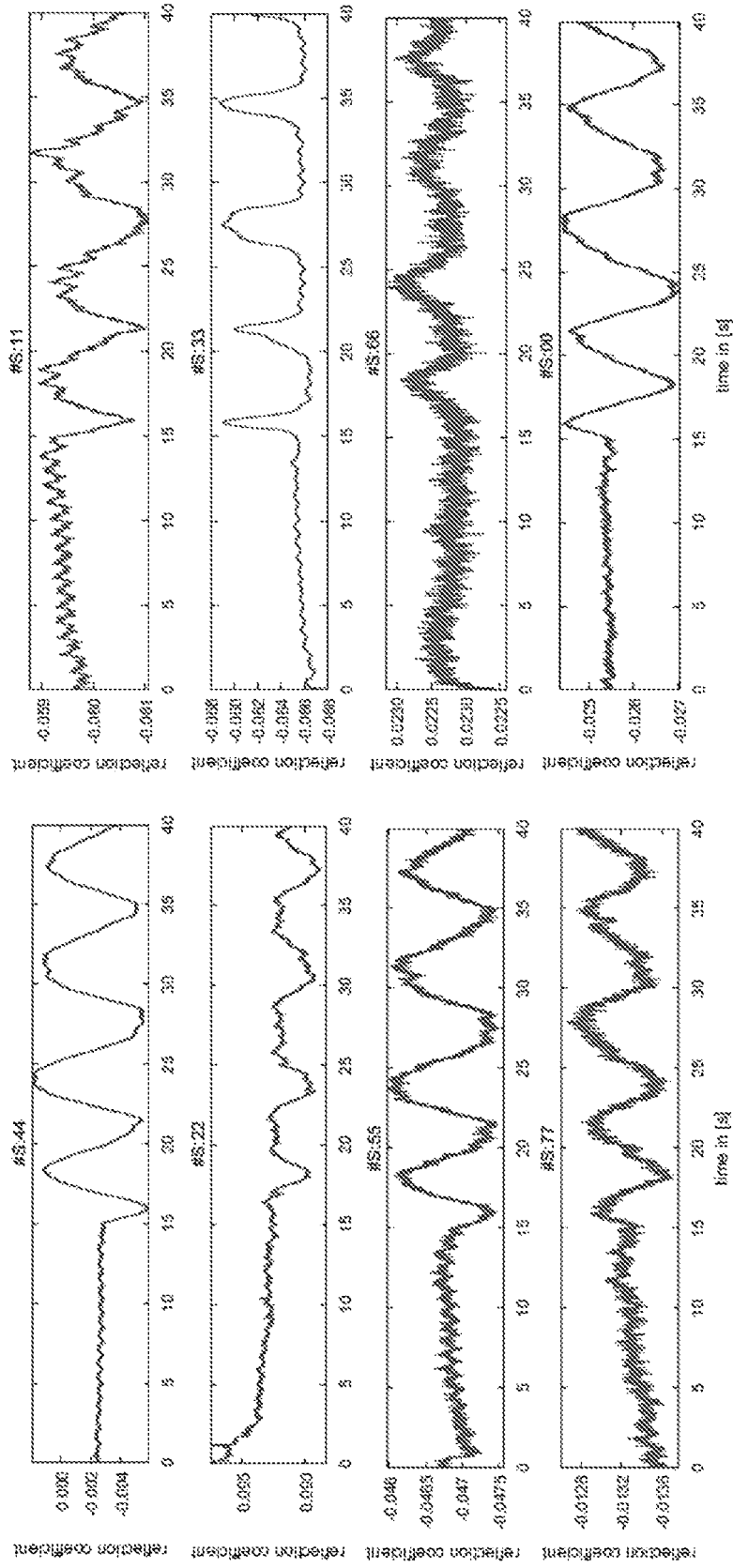
FIG. 1A shows examples of reflected power coefficients (diagonal of the scattering matrix S) during a 40 second scan with approximately 15 second breath hold followed by free breathing showing the reflection of each coil element.

Described below are methods for' extracting subject motion from multi-channel electrical coupling in imaging of the subject. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It is to be understood that, unless otherwise indicated, the present disclosure is not limited to particular types of methods and systems relating for extracting subject motion in imaging of the subject, and particular software[s] for post-processing and analysis, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a scanner" includes a plurality of scanners. In this specification and in the claims that follow, reference will be made to a number of terms that shall be defined to have the following meanings unless a contrary intention is apparent.

Description

Provided herein are systems and methods to monitor changes in subject motion relating to imaging, for example magnetic resonance (MR) imaging, of a subject. In some aspects, motion can be of a subject or a region of interest of subject (such as an organ or specific tissue). In various aspects, the subject can be a human patient. As described herein, changes in the position of the subject and the subject's organs can be monitored by measuring how external RF coils couple to the subject and one another' and change the scattering of the RF coils, for example scattering of RF pulses transmitted by the coils. Changes in position influence this coupling and the scattering and can be detrimental to the quality of the imaging.

Changes in electrical scattering can be due to movement of the conductive components of the subject's body. For example, as a patient within an MR scanner breathes or heart beats the conductive elements move around. The RF coils on or adjacent to the surface of the body (that may be already present and used for imaging) will then couple to each other and the subject in a different way. Existing scanners of various field strengths can contain hardware capable of sensing the forward and reflected power from these coils and this can be used to dynamically determine the scattering between the RF coils or RF coil network. However, until now they have not be so used.

By measuring the scattering whilst also collecting images, for example rapid MR images, mappings can be generated that describe subject motion as a function of the scattering. Subsequently the scattering measurements can be used on their own to accurately predict the position of the subject. Effects of drift in the scattering that are not due to subject motion can be monitored and compensated by additional image data, for example additional infrequent MR image data. Knowledge of the subject motion can be used to correct for and obtain better image quality either by using this information to change the acquisition gating (i.e., the timing for pulse initiation and subsequent data acquisition) and/or to change the image reconstruction, providing improvements over existing systems and methods in the field.

Systems and methods as described herein provide for improvements in existing systems and methods for generating and acquiring MR images. Systems and methods as described herein can be used to improve MR image quality when imaging subjects by controlling and/or compensating for subject motion. Motions that can influence scattering and that can be corrected can include breathing, cardiac, and involuntary motions (i.e. coughing, sneezing, twitching, swallowing, head movements, limb movements, etc.). Scattering measurements that detect these changes can be used on their own to predict subject motion and can provide for better MR images by appropriately gating image acquisition, or they can be used for motion reconstruction to compensate for motion during image reconstruction following acquisition.

Systems and methods as described herein are improvements upon and different from existing systems and methods in several ways. First, in various aspects no additional external hardware connected to the patient is necessarily required, making for faster subject set-up, a safer subject environment (no RF burns from ECG equipment for example), and reduced cost. However, existing hardware has not been utilized to monitor motion in the manner as described below and herein Further, systems and methods as described herein monitor more independent characteristics of motion. Existing systems and methods with ECG and respiration monitoring are limited to detecting at most 2 degrees of freedom. In various aspects, systems and methods as described herein utilize a parallel processing approach with multiple parallel transmitter coils (from 2 to 16 coils or channels, for example) that couple to a subject, providing for more parameters that can be used to provide more detailed measurements than approaches with 2 degrees of freedom. For example, systems and methods as described herein using coil coupling and an 8 channel system can provide for 64 complex valued parameters that can be detected, which provides a more detailed measurement of the subject. Further the present coil coupling approach provides information at a temporal resolution of the RF pulses, which for a rapid SSFP sequence can be around 3 ms temporal resolution.

In various aspects, systems and methods as described herein improve upon those previously described by at least the use of a multiple channel approach that integrates the information from the multiple channels. In an aspect 8 channels can be used. Further, systems and methods as described herein can utilize imaging data to convert the dynamic coupling parameters into useful motion parameters. It is this combined imaging and RF scattering solution and the associated hardware and methods which makes this approach so valuable, as it provides a solution that will work in all subjects and can be readily translated onto clinical scanners (such as MRI scanners) for both image acquisition and image reconstruction.

Described herein are systems for acquiring and reconstructing MR images that can monitor subject motion. The subject can be, but need not be, a human patient. The subject can also be an animal, plant or inanimate subject. The subject can have a vascular system of interest. In various aspects, the methods and systems herein can comprise an MR scanner with a plurality of transmit channels and an image reconstruction computer (computers and processors described more in depth later in the discussion). They can also comprise a measurement and physiological control unit (MPCU), analog-to-digital converters (ADCs), a specific absorption rate (SAR) monitoring system, and a plurality of RF transmit, receive, or transmit/receive coils that can be positioned near or around a region of interest (ROI). In an aspect, there are at least two such RF coils. The components can be configured to send/receive data and/or electromagnetic signals (radio frequency pulses, for example) between each other.

The SAR monitoring system is a safeguard of MR scanners to measure the effects of transmitted RF voltages on a subject. As described herein, this system can be utilized to monitor subject motion using existing or custom hardware based on reflected power measurements. A SAR system can comprise directional couplers ("dicos", one for each transmit channel) that monitor the forward and returned RF voltage on each transmit channel. Signals in and out of the dicos can be demodulated and digitized by an ADC of the system and delivered in real time to a local SAR monitor (which can comprise software implemented on a computer, such as the image reconstruction computer).

The SAR monitoring system can also comprise a plurality of transmit/receive RF coils in parallel. These coils can capture measurements of the discos before they enter the SAR monitoring system. There can be one transmit/receive coil per transmit channel of the system. In an aspect, the plurality of parallel transmit/receive RF coils can be from 2 to 16 coils. The exact positioning and configuration of the parallel transmit/receive RF coils can be determined by an end user depending on field strength of the MR scanner and subject anatomy (i.e., ROI of the subject). The plurality of parallel transmit/receive coils can electrically couple to a subject during a scan, and the coils can also couple to each other during a scan.

Described herein are methods for monitoring diaphragm motion during an MR scan. The methods can use a reduced scattering matrix measured during an RF pulse with a plurality of parallel transmit coils. A method for determining diaphragm position can use changes in scattering or in the scattering coefficients of scattering matrices of returned voltages from RF pulses to track diaphragm motion. In one or more aspects, pulses as described herein can be part of a gradient echo (GRE), inversion recovery, balanced steady state free precession (SSFP), or other pulse sequences or specifically applied for the purpose of motion measurement. In embodiments, pulses as described herein can have a shapes characteristic of a sine, Guass, rect and/or hyperbolic secant, Pulses as described herein can be the same on each transmit coil or they can be different on each transmit coil, such as frequency multiplexed, parallel transmit spokes, or parallel transmit spirals.

Figure 22:
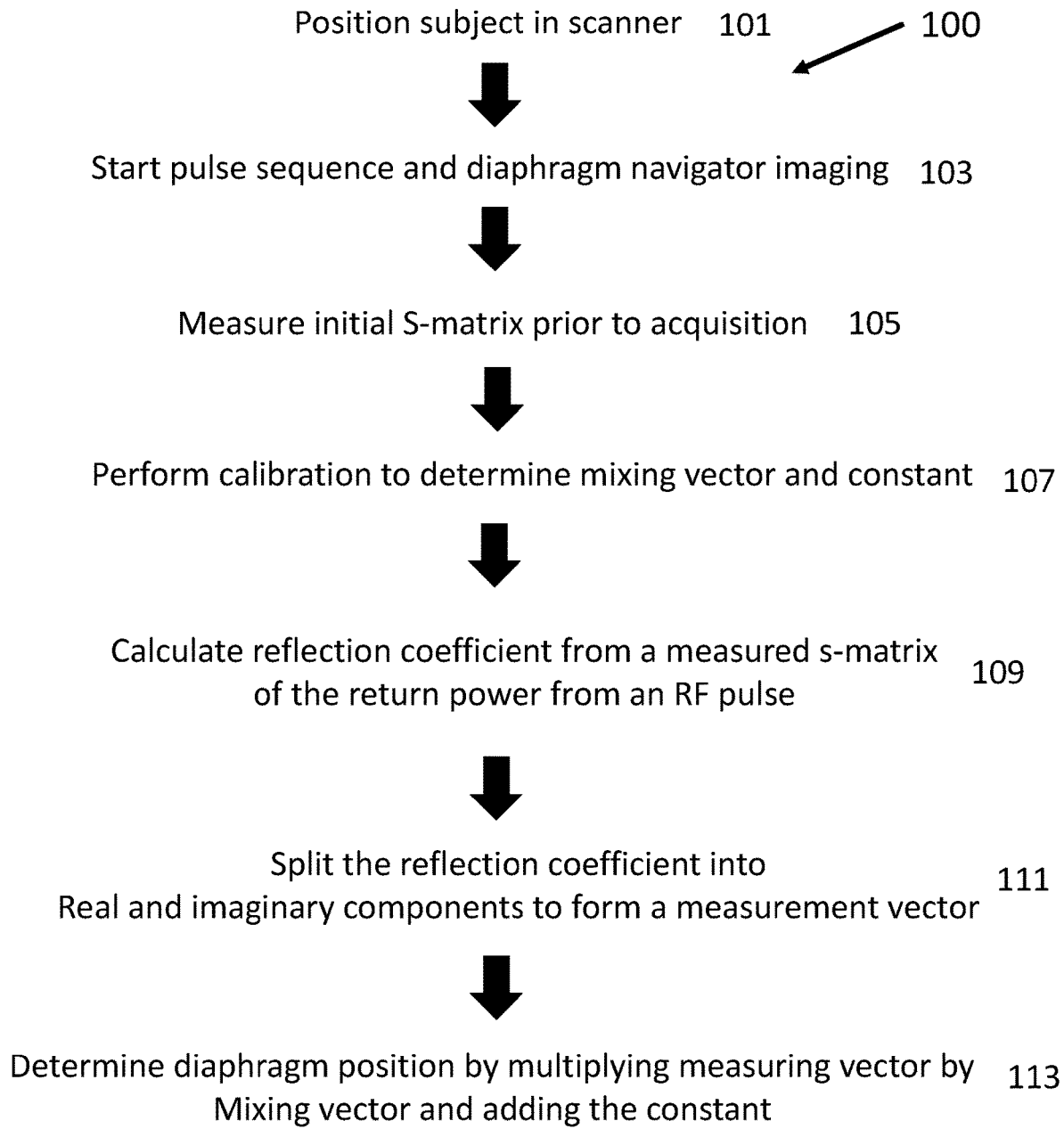
FIG. 22 is a flow chart showing an embodiment of the methods as described herein.

An embodiment of a method 100 to determine or extract diaphragm position is shown in FIG. 22. A subject can be positioned 101 in association with a scanner, for example an MR scanner with a field strength which contains an SAR monitoring system with a commercial parallel transmit (pTX) system containing a plurality of parallel transmit coils. A pulse sequence can be initiated 103 on the scanner and navigator imaging can be performed on an anatomical region of interest (ROI) of the subject, such as a diaphragm. The anatomical region of interest can be undergoing motion and can be undergoing motion according to a cycle, such as a relax-contract cycle. After pulse sequence and navigator imaging initiation, an initial S-matrix can be measured 105 prior to acquisition. A calibration can then be performed 107 with the initial S-matrix to determine a mixing vector and a constant. A reflection coefficient can be calculated 109 from a measured S-matrix of the return power from an RF pulse. The reflection coefficient can be split 111 into real and imaginary components to form a measurement vector, and the position of the anatomical region of interest can be determined 113 by multiplying the measuring vector by the mixing vector and adding the constant.

In an embodiment, an initial S-matrix (S(0)) is measured prior to image data acquisition. This matrix can be used to calculate an expected returned voltage, $V_{exp}(t)$, which will differ from the measured returned voltage at time t if S(t) has changed. The ratio of the return voltage to the expected return voltage is taken for each channel to generate complex scattering coefficients or reduced scattering matrix, for example $\Gamma_{i,k}$ is the scattering coefficient vector for channel i for a given RF pulse k. The scattering coefficients can then be separated into real and imaginary components. For example, in a 8 channel system for a vector $\Gamma_{i,k}$ as described above, a 16 element vector $\Gamma'_k$ can be formed by separating $\Gamma_{i,k}$ into real and imaginary components. Diaphragm position ($d_k$) can be determined according to the equation $d_k = \Gamma'_k M + c$, where M and c are a mixing vector and constants respectively that are determined in a calibration where the diaphragm position is measured with MRI and $\Gamma'_k$ is recorded for each diaphragm image. A least squares optimization (linear regression) can be carried out to find the optimal mixing vector such that it predicts the diaphragm position.

In this way, changes in the scattering coefficients can be transformed into quantitative diaphragm positions using a series of MR images. In an aspect, this can be done in a learning interval with a diaphragm navigator which determines the diaphragm edge. Diaphragm monitoring in this way can be used to gate MR image acquisition or image reconstruction retrospectively.

Also described herein are methods for monitoring cardiac motion during an MR scan. The methods can use the scattering from an RF pulse with a plurality of parallel transmit coils. A method for determining cardiac motion can use changes in scattering or in the scattering coefficients (reduced scattering matrix) of scatter matrices of returned voltages from RF pulses used for excitation, magnetization preparation etc, or specifically designed to track cardiac motion. In one or more aspects, pulses as described herein can be or required to be executed with sufficient transmit amplitude that they can be measured by the directional couplers. They can be repeated as often as required, either as part of the designated pulse sequence (GRE is used in methods shown here) or repeated as and when motion is to be measured.

Figure 23:
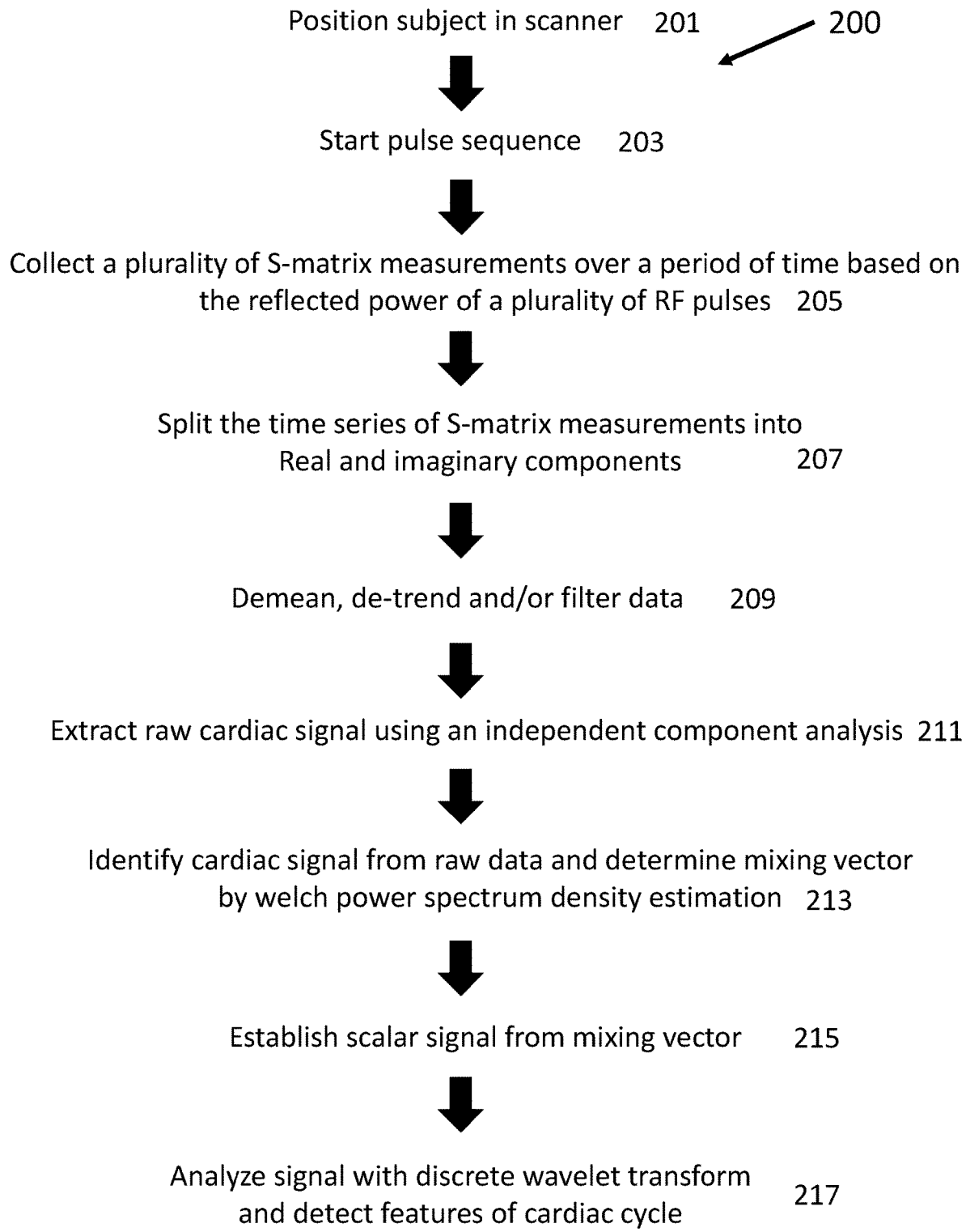
FIG. 23 is a flow chart showing an embodiment of the methods as described herein.
Figure 24:
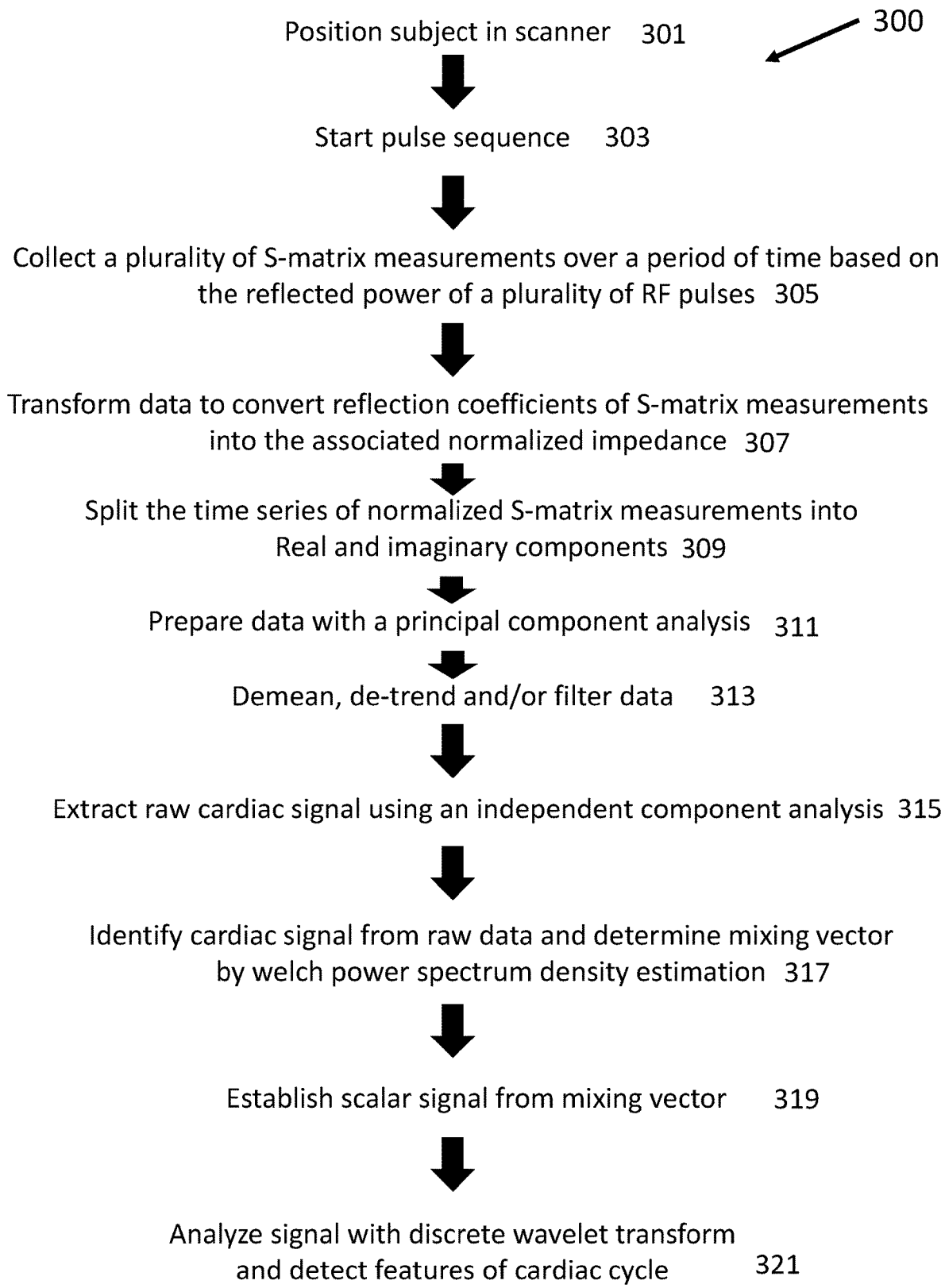
FIG. 24 is a flow chart showing an embodiment of the methods as described here.
Figure 25A:
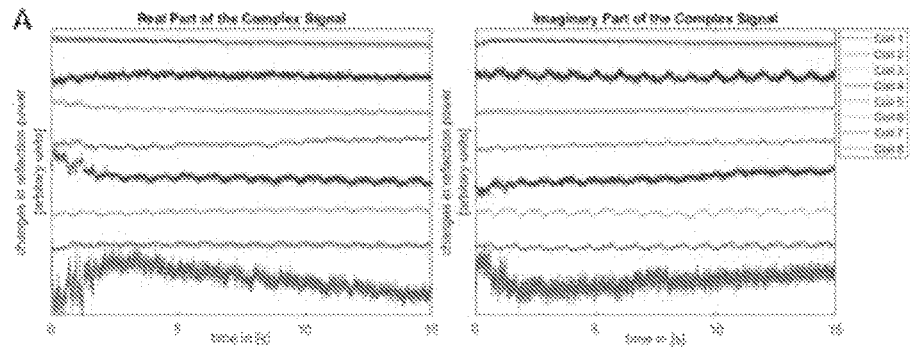
FIGS. 25A-25D show an example of raw measurements of the normalised complex returned voltage coefficient Γ (FIG. 25A), the extracted raw cardiac signal using the described methods (FIG. 25B) and two selected peaks (FIG. 25C). Peak detection was carried out on the filtered signal using discrete wavelet transformation with maximal overlap.
Figure 25B:
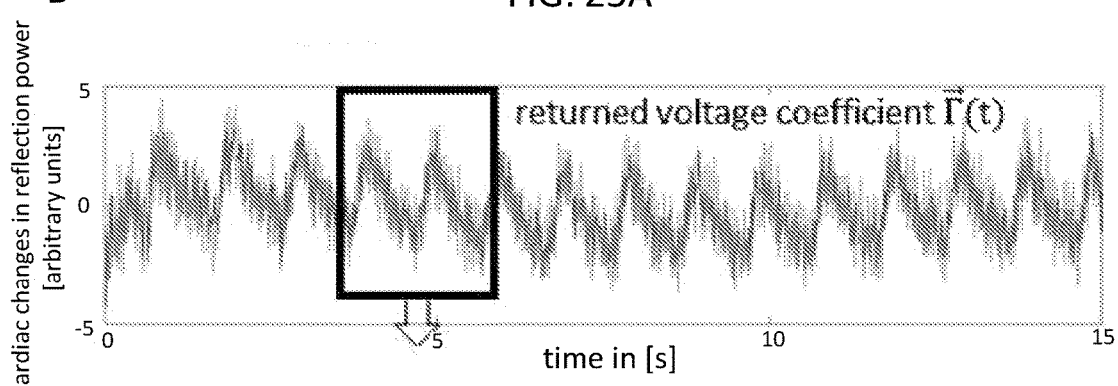
Figure 25C:
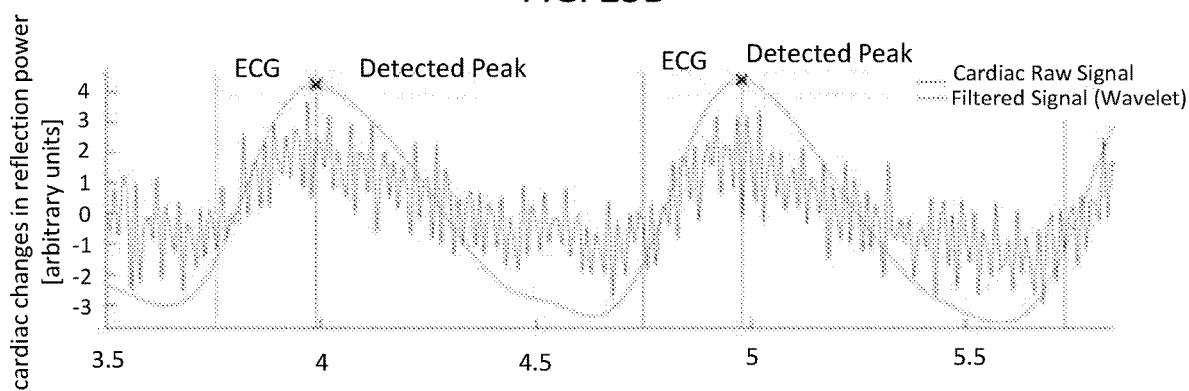
Figure 25D:
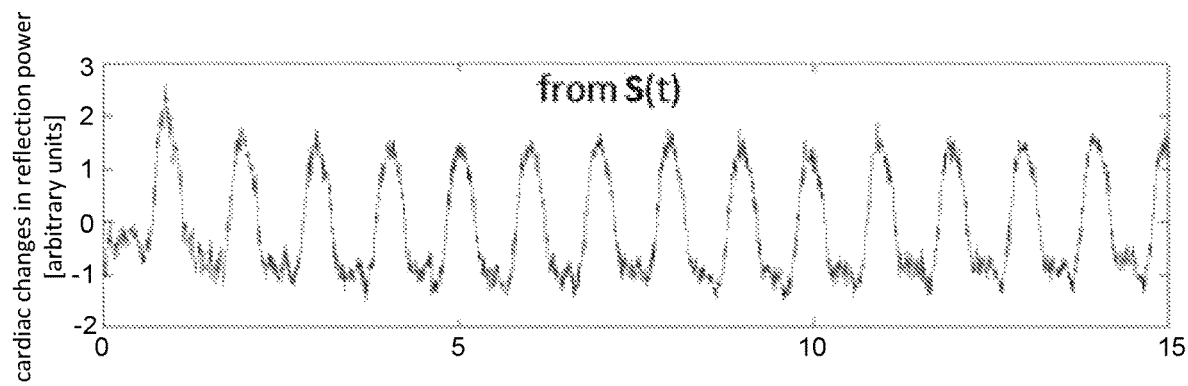

Embodiments of methods for extracting subject motion as described herein can also be seen in FIG. 23 and FIG. 24. In an embodiment, the method 200 can include positioning 201 a subject in association with a scanner, as previously described. A pulse sequence can be started 203 on the scanner to acquire measurements from the subject, A plurality of S-matrix measurements over a period of time can be collected 205 based on the reflected power of a plurality of RF pulses. At least one of these measurements can be used as a calibration signal, and a mixing vector and a constant can be determined from the calibration S-matrix measurement. The time series of S-matrix measurements can be split 207 into real and imaginary components, and these data can be demeaned, de-trended, and/or filtered 209. The raw signal of an anatomical region of interest (ROI), for example the diaphragm or the heart, can be extracted 211 from the processed S-matrix data using an independent component analysis. The anatomical signal can then be identified 213 within or from the raw data, and a mixing vector can be determined, for example by Welch power spectrum density estimation of other suitable technique. A signal, such as a scalar signal, can be established 215 from the mixing vector and analyzed 217 with discrete wavelet transformation or other suitable technique. The features of the cycle of motion of the anatomical region can then be determined, such as the cardiac cycle for example.

In an embodiment of the method 300, a subject can be positioned 301 in association with a scanner, such as an MR scanner with a SAR monitoring system comprising a plurality of parallel transmit coils. A pulse sequence can be initiated 303 on the scanner to acquire measurements from the subject. A plurality of S-matrix measurements over a period of time based on the reflected power of a plurality of RF pulses can be collected 305. Data from the S-matrix measurements can be transformed 307 to convert reflection coefficients of S-matrix measurements into the associated normalized impedance. The time series of normalized S-matrix measurements can be split 309 into real and imaginary components, and the data can be prepped 311 for further analysis using a principal component analysis or other suitable techniques. The data can be demeaned, de-trended, and/or filtered 313, and the raw signal from an anatomical region of interest, such as the heart, can be extracted 315 using an independent component analysis or other suitable technique. The signal from the anatomical region of interest (ROI) can be identified 317 from the raw data, and a mixing vector can be determined, for example by Welch power spectrum density estimation or other suitable techniques. A signal, such as a scalar signal, can be established 319 from the mixing vector, and the signal can be analyzed 321 with discrete wavelet transformation or other suitable technique to detect the features of the cycle of motion of the anatomical region or area of interest.

In embodiments, cardiac motion can be monitored and extracted by calculating one or more full complex S-matrices acquired from dico data following a parallel transmit pulse. The one or more S-matrices can be transformed to normalize impedance, by performing a Mobius transformation for example. The S-matrix or transformed S-matrix can be separated into real and imaginary components. Drifts can be removed by demeaning and de-trending the data. Data can then be filtered in backward and/or forward function to eliminate spikes and improve signal-to-noise (SNR) ratio. Independent component analysis (ICA) can then be performed to extract the raw cardiac signal. After ICA, the cardiac signal can be identified by a power spectral density estimate with highest power over a frequency corresponding to the heartbeat (0.6 hz to 2.4 hz for 40 bpm to 140 bpm, for example). From this data, a mixing vector can be extracted and the signal analyzed for cardiac cycle feature detection using a multiresolution discrete wavelet transform (DWT) with maximum overlay. Peak detection can be carried out to identify features of the cardiac cycle. These methods can be used in conjunction with others, such as ECG or the diaphragm monitoring described above, and can be used to gate the acquisition of MR images or the reconstruction of MR images.

Figure 21:
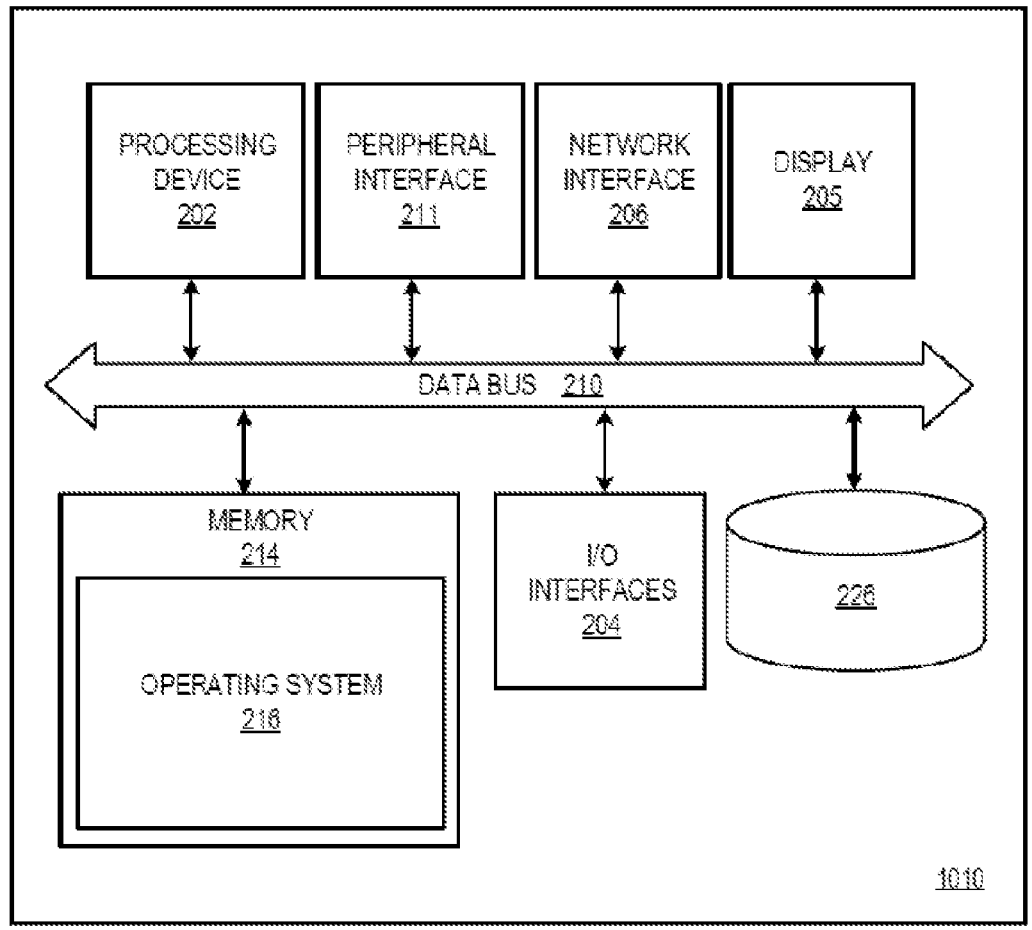
FIG. 21 shows an embodiment of a computing device or apparatus 1010 that can be implemented in the systems as described herein and which can implement methods as described herein.

FIG. 21 depicts an apparatus 1010 in which the systems, analysis systems, breadboard analysis systems, or other systems described herein may be coupled to in order to assist in automation of the system. The apparatus 1010 can be embodied in any one of a wide variety of wired and/or wireless computing devices, multiprocessor computing device, and so forth. As shown in FIG. 21, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 can be coupled to one or more peripheral measurement devices (not shown) connected to the apparatus 1010 via the peripheral interface 211.

The processing device 202 can include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications can include application specific software which may be configured to perform some or all of the methods described herein (Labview, for example), In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 can comprise a computer monitor, a plasma screen for a PC, a liquid crystal display (LCD) on a hand held device, or other display device.

In the context of this disclosure, a non-transitory computer-readable medium stores programs for use by or in connection with an instruction execution system, apparatus, or device. More specific examples of a computer-readable medium can include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 21, network interface device 206 comprises various components used to transmit and/or receive data over a network environment. For example, the network interface 206 can include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 can communicate with one or more computing devices via the network interface 206 over a network. The apparatus 1010 may further comprise mass storage 226. The peripheral 211 interface supports various interfaces including, but not limited to IEEE-1394 High Performance Serial Bus (Firewire), USB, thunderbolt, a serial connection, and a parallel connection.

The apparatus 1010 shown in FIG. 21 can be embodied, for example, as a magnetic resonance apparatus, which includes a processing module or logic for performing conditional data processing, and may be implemented either off-line or directly in a magnetic resonance apparatus. For such embodiments, the apparatus 1010 can be implemented as a multi-channel, multi-coil system with advanced parallel image processing capabilities, and direct implementation makes it possible to generate images, for example, immediate T1 maps, available for viewing immediately after image acquisition, thereby allowing re-acquisition on-the-spot if necessary. Examples of apparatus in which the present systems and methods may be implemented are described in U.S. Pat. Nos. 5,993,398 and 6,245,027 and U.S. Publication No. 2011/0181285, which are incorporated by reference as if fully set forth herein.

The flow charts of FIGS. 22-24 show examples of functionality that can be implemented in the apparatus 1010 of FIG. 21. If embodied in software, each block shown in FIGS. 22-24 can represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 21) in a computer system or other system. The machine code can be converted from the source code, etc. If embodied in hardware, each block may represent a circuit or a number of interconnected circuits to implement the specified logical function(s).

Although the flowcharts of FIGS. 22-24 show a specific order of execution, it is understood that the order of execution may differ from that which is depicted. For example, the order of execution of two or more blocks may be scrambled relative to the order shown. Also, two or more blocks shown in succession in FIGS. 22-24 can be executed concurrently or with partial concurrence. Further, in some embodiments, one or more of the blocks shown in FIGS. 22-24 can be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

EXAMPLES

Now having described various embodiments of the disclosure, in general, the examples below describe some additional embodiments. While embodiments of the present disclosure are described in connection with the examples and the corresponding text and figures, there is no intent to limit embodiments of the disclosure to these descriptions. On the contrary, the intent is to cover all alternatives, modifications, and equivalents included within the spirit and scope of embodiments of the present disclosure Example 1

Provided in this example is a novel approach that can use directional couplers from the commercial SAR monitoring system and an eight channel transmission line (TEM) coil to measure the scattering coefficient on each channel simultaneously. A scattering matrix was calculated to determine cardiac motion with an independent component analysis on 6 healthy subjects. 7 features were identified using maximal overlap discrete wavelets transform and gradients and were assessed for their eligibility for cardiac gating by comparison to ECG.

A robust estimation of cardiac motion is shown in periods of breath hold and free breathing. Three features were identified as potential cardiac trigger for pulse sequence initiation and image data acquisition. All three of these features had 100% positive predictive value and 100% sensitivity. Preliminary results for retrospectively gated and reconstructed 2D-CINE images using one of the presented features demonstrate the potential of cardiac gating using this method. This approach can improve cardiac imaging at ultra-high field CMR by providing robust triggering and an optimised workflow as it requires no additional set-up.

Introduction

Cardiovascular MRI (CMR) at ultra-high field strength is a growing field of research [1], [2]. As such there is a need for more reliable, accurate, and user independent gating and triggering methods. The current gold standard gating method for determining MRI pulse sequence initiation, ECG, is affected by strong magnetic fields through the magnetohydrodynamic effects (MHD). MHD effects result from the blood flow in the aortic arch [3], [4] where the resulting electric field overlays the surface potential of the ECG electrodes and leads to a distortion in the S-T interval and therefore to a misinterpreted R-wave detection [5]. Successful ECG lead setup requires lead re-positioning in a number of subjects [6], leading to increased setup time. Missed or false trigger results can increase scan time or significantly degrade image quality in CMR.

Different approaches have been developed to improve cardiac gating and estimate motion in high magnetic field MRI. For example, an improved QRS detection method using vectorcardiographic (VCG) gating enables improved R-peak detection [7][8]. Adapted navigating pulses coupled with multi-channel receive arrays have been used for automatic determination of the cardiac and respiratory motion [9]. Alternative external devices have been developed including acoustic cardiac triggering using heart tone [10], and pilot tone RF-signal [11] which is picked up by the received coils and is modulated by respiratory and cardiac motion [12], [13]. These methods can provide improved cardiac gating compared to standard ECG. There is still a need, however, for a gating setup that does not carry risk of surface heating [14], [15], require additional hardware, or have the need for complicated technical, expert, hardware setup.

A different approach, first introduced by Buikman et.al. [16], uses reflected power measurements to detect and assess motion. It was shown that patient movement changes the quality factor of the RF coil (a single coil) and therefore the reflection coefficient which could be measured using directional couplers (dico's) on a 2 T single transmit MRI system. Other previous work uses a single receive loop [17] or the commercial parallel receive coils [18] to measure the changes in the coil load and to assess respiratory or heart motion.

In this example 8-channel transmit coil on a commercial 7T MR Scanner equipped with dico's is used as part of its local SAR monitor, though as noted above fewer coils (at least two interacting coupled coils) or more coils can be used. Scattering matrix (S-matrix) measurements from these dico's are used to determine the cardiac motion with an independent component analysis (ICA).

Methods

Scattering Matrix

The principles of an S-matrix of a n-port electrical network are applied herein to describe the reflection and coupling properties of a multi-transmit (pTX) MRI coil. The S-matrix is complex and modulated by changes in the complex permittivity (conductivity and permittivity) of the load [19]. The complex permittivity observed by the coil is influenced by several physiological effects including the beating and moving or the heart, displacement of blood, and breathing. To ensure sensitivity to the complex nature of the underlying effect, a complex scattering coefficient is used.

The full scattering matrix was acquired using the dico data captured as part of the local SAR monitor in a commercial parallel transmit (pTX) system (Siemens 7.0 T Magnetom scanner, Erlangen, Germany). An eight channel pTX transverse electromagnetic resonator coil (custom made. [20]) was used with four posterior and four anterior elements spread over a 20 cm field of view (left to right and up to down) centered over the heart. A parallel-transmit pulse sequence with RF pulses (Gaussian shaped pulse duration=5 ms, TR=10 ms) with a different frequency on each transmit channel was applied. Each channel had a different transmit frequency ranging from 0 kHz to 14 kHz in 2 kHz steps to measure the S-Matrix The complex scattering coefficient Γ is defined as the ratio of the complex amplitude of the returned voltage divided by the complex amplitude of the expected returned voltage as defined by the scattering-matrix (S0).

$$\Gamma = \frac{V_{Reflected}}{V_{incident}} \quad (1)$$

The scattering is acquired by measuring the returned voltage not only from the forward channel but on all channels simultaneously. For example, in a multi-channel system the forwarded voltage $V_{F1}$ on channel 1 results in reflection $V_{i,\ reflected}$ on each channel, separated and determined by the scattering vector $S_{i,1}$. Applying the incident wave and measurements of the reflected wave on each channel simultaneously, results in the acquisition of the full S-matrix. Using a frequency offset for each channel, the complex scattering matrix $S_{i,j}$ is then defined as the ratio of the complex amplitude of the reflection observed on channel i at the frequency of channel j divided by complex amplitude of the incident wave on channel j:

$$S_{i,j} = \frac{V_{i,j,Reflected}}{V_{j,incident}} \quad (2)$$

A Möbius transformation was used to convert the S-matrix into the associated, normalised impedance:

$$Z_{i,j} = \frac{1 + S_{i,j}}{1 - S_{i,j}} \quad (3)$$

Cardiac Motion Estimation Using Reflected Power

The time series of S-matrix measurements was analysed using the following major steps:

1. The Möbius transformed S-matrix was separated into its real and imaginary parts with one measurement matrix M containing 128 signals with a length of 4000 points (t≈40 seconds, sampling frequency f=100 Hz).
2. Demeaning and de-trending was carried out to remove any drifts by using quadratic polynomials which were fitted and subtracted from the data.
3. A digital Butterworth low pass filter [21] was applied to eliminate spikes and to improve SNR (infinite impulse response design with an order of 17, passband frequency 7.5 Hz, stopband frequency 15 Hz). The filter was applied in a forward and backward fashion to avoid phase shifts in the filtered signal.
4. The FastICA Software package for Matlab (Version 2.5, [23]) was used for dimensionality reduction and whitening with a principal component analysis (PCA) to prepare the data for the use of an independent component analysis (ICA). The dimensionality reduction is based on the eigenvalues of the covariance matrix and values greater than a threshold of ε=0.75×10$^{-7}$ (default ε=1×10$^{-7}$ were kept and the dimension is reduced to the number of kept eigenvalues.
5. Performing an ICA assuming that the measurements $M_k$ of the normalized impedance coefficient can be described as a linear mixture of the different underlying signal components:

$$M_k = A \cdot s_k \quad (4)$$

where A is the linear mixing matrix and $s_k$ the source signals at a time instant k.

In an aspect of the present method, an ICA based on Hyvarinen's fixed-point method [22] (FastICA forMatlab V2.5, [23]) is used to find the corresponding demixing matrix W so that:

$$\hat{s} = W \cdot M_k \quad (5)$$

where $\hat{s}_k$ are the estimated source signals n at the time k (e.g. independent component) which are assumed to be noise, artefacts as well as the desired cardiac and respiratory information. $M_k$ is the measurement vector containing 128 signals at time k (8×8 channels, each with real and imaginary parts).

Lastly, the corresponding cardiac component $\hat{s}_{cardiac}$ was identified by finding the maximum power in a Welch power spectrum density estimation [24] within the frequency range of 0.6 Hz to 2.4 Hz which can correspond to a heart rate between 40 bpm and 140 bpm respectively. The stability of the independent component selection was increased by subtracting the high frequency content (>2.5 Hz). Finally, the corresponding demixing vector $w_{cardiac}$ was extracted from the demixing matrix W since only the cardiac information is needed for the following signal analysis in this work.

Data Acquisition and Subjects

The measurements of reflected power were performed outside and inside the MR Scanner during a breath hold of approximately 15 seconds followed by free breathing for another 25 seconds.

Four elements of the coil were placed anterior on the chest of the subject and the other four elements were placed posterior. Each set of 4 coil elements were in a fixed position relative to each other and positioned over the heart.

This study was conducted on 6 healthy adults (Male, age=24-39) with no history of cardiovascular disease. Cardiac cycles with abnormal cardiac activity (e.g. extra-systoles) were excluded from the dataset and the rest of the data was kept, ECG trigger times were recorded in the raw DICO measurement data from a 3-lead commercial vector ECG module (Siemens, Erlangen, Germany), Disposable, MR-compatible electrodes were placed on the chest wall according to the manufactures guidelines resulting in a reduced orthogonal 2-lead configuration. The vector ECG training period was performed outside the scanner with the subject lying on the table (home position).

All offline signal analysis was conducted in MATLAB (MathWorks, Natick, Mass.). Statistical evaluation was carried out using Minitab16 (Minitab Inc, State College, Pa.).

Retrospective Cardiac Signal Analysis

Figure 1B:
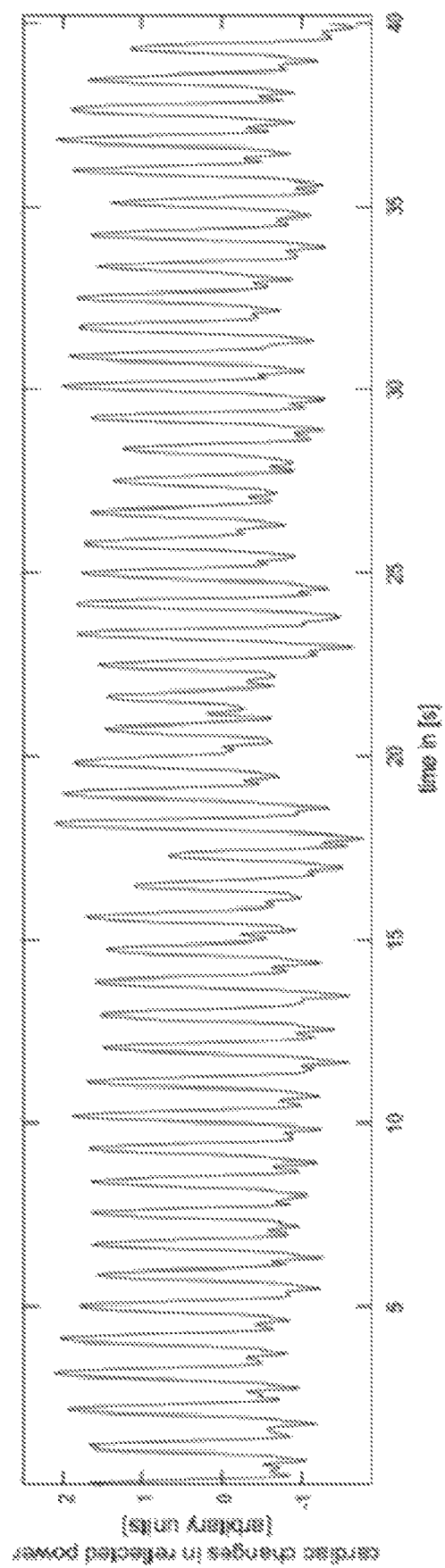
FIG. 1B shows the extracted and identified corresponding independent component $\hat{s}_{cardiac}$ using an independent component analysis (ICA).
Figure 2:
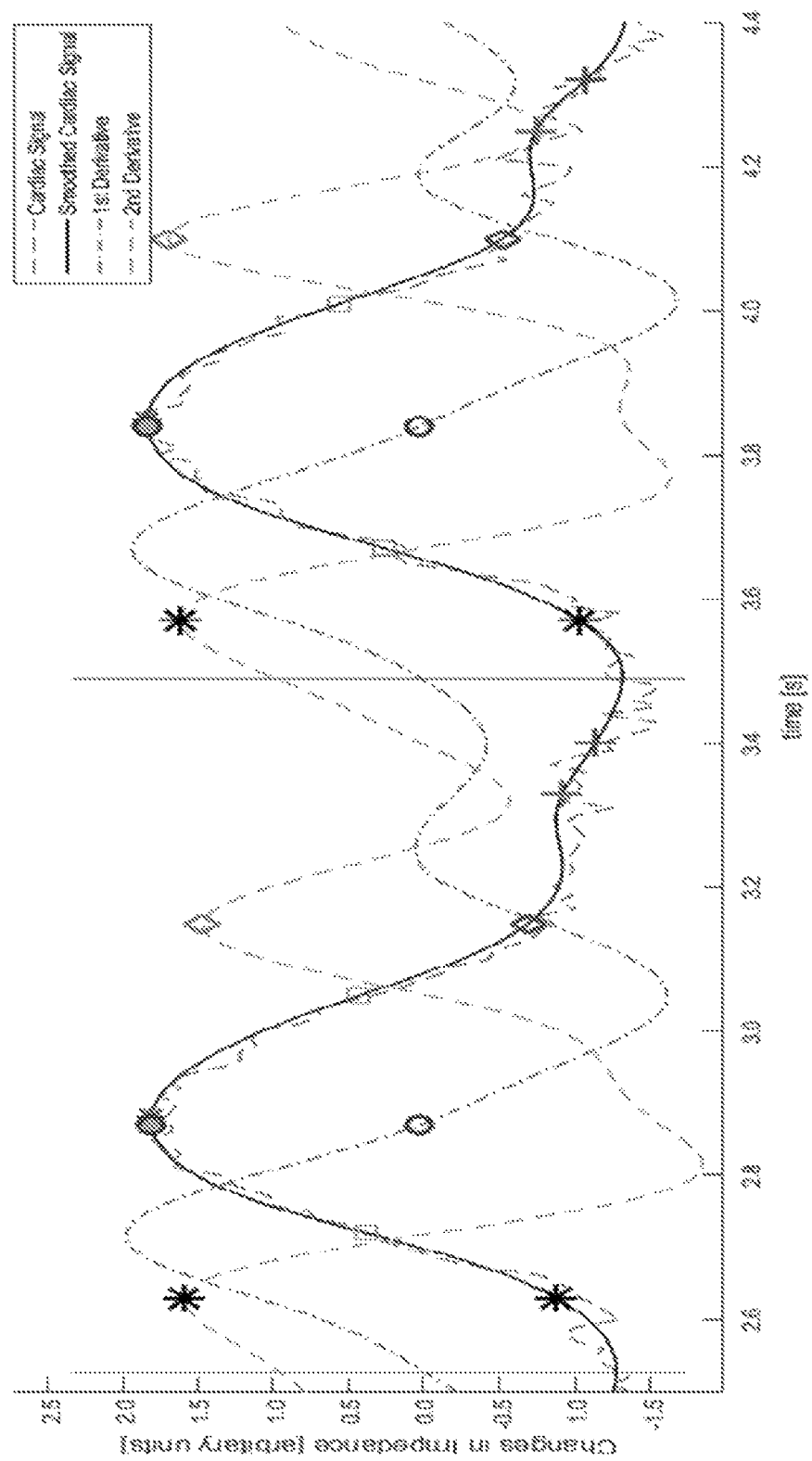
FIG. 2 shows an embodiment of feature detection in the extracted cardiac signal. Features are as follows: (*) Feature 1 (wavelet), (*) Feature 2 (wavelet) and (○) feature 3 (gradient) for main peak detection, (◇) feature 4 for start of diastasis (gradients),) (+) feature 5 to detect the end of diastasis (wavelet), (+) feature 6 for atrial systole (gradients) and (*) feature 7 for systole (gradients). Vertical red lines indicate the ECG trigger.

After the cardiac signal was extracted using reflected power measurements and an ICA (FIGS. 1A-1B), 7 features were identified and assessed in a retrospective signal analysis to detect different stages of the heart cycle. Three features for end systole, the main peak in the signal (features 1-3), one to detect the start of the diastasis when the heart is almost at rest (feature 4), two for the start of atrial systole (feature 5 and 6) and one to detect the start of ventricular contraction (feature 7). These features are plotted in FIG. 2 on the demixed signal. The demixed data either filtered or raw were used.

To ensure a consistent signal analysis, the polarity of the cardiac signal was normalized by performing a peak detection on the absolute demixed data followed by a k-means clustering (using the Matlab function k-means [25],[26]) with the corresponding peak height. End systole is identified as the larger of two peaks, the smaller peak is expected to be due to atrial contraction.

Two methods were identified for feature classification in the cardiac signal. The first using a discrete wavelet transform of the unfiltered but demixed data, the second using the first and second derivatives of the low pass filtered signal to identify rest and high velocity in the cardiac cycle.

A multi-resolution wavelet approach is used based on a maximal overlap discrete wavelet transform (DWT) [27]. A mother wavelet with N=5 vanishing moments of the family of symlets was chosen as it comes closest to the expected waveform of the cardiac signal. The data was reflected to minimize boundary problems at its ends.

The scaling factor a of the discrete wavelet was chosen in respect to the expected range of the heart rate given by the dominant frequencies. The following relationship between the factor a and the centre frequency f, of the wavelet [28] were used:

$$f_a = \frac{f_c}{a \cdot \Delta t} \tag{6}$$

Where $f_a$ is the pseudo-frequency corresponding to the scale a with fc, the centre frequency of the wavelet ($f_c$=0.667 Hz for a symlet, n=5) and $\Delta t$ the sampling period (in this work $\Delta t$=TR=0.01 s).

The second method uses the first and second derivatives to detect peaks in the signal using the zero-crossing as well as periods of rest through changes in the velocity. Before gradients of the signal were calculated, a Savitzky-Golay smoothing filter [29] of order 7 was applied using a frame with a number of points which corresponds to a signal length of 0.45 seconds (using a TR=10 ms in this work results in n=40).

Feature 1: Main Peak Detection using Wavelets

After applying a DWT on the cardiac signal, all coefficients except the one which corresponds with the expected heart rate, were thresholded or minimised before an inverse DWT was applied. A peak detection was carried out on the resulting signal to determine feature 1.

Features 2 and 5: Main Peak and Atrial Systole Detection using Wavelets

Features 2 and 5 were determined in a similar way to feature 1. The main difference is the use of a smaller wavelet scaling coefficient resulting in oscillations at a higher pseudo-frequency. In the expected cardiac waveform, this can lead to two main peaks where one is due to ventricular and one due to atrial contraction. Peak detection was carried out using the in-build Matlab function and a k-means clustering method was used to separate both in an automated fashion.

Feature 3: Main Peak Detection using First Derivatives

Zero-crossings of the smoothed first derivative within the positive parts of the signal were used to identify the peak at end systole.

Features 4 and 7: Start of Diastasis and Start of Ventricular Contraction using second Derivatives A peak detection on the smoothed second derivative was carried out to identify rapid changes in the cardiac signal. A k-means clustering method was used to distinguish between early diastole (negative slope) and the rapid changes of ventricular contraction (positive slope and higher peak). The peak detection was limited with a minimum peak prominence and peak distance to avoid false positives.

Feature 6: Atrial Systole using First Derivatives

Peak detection on the inverted first derivative was used to identify changes in the descending signal, corresponding to ventricular tilling from the atrial contraction. Changes from atrial contraction will be smaller than those from the ventricular refilling in early diastole, a k-means clustering is used to distinguish the two events.

Method Evaluation

Figure 3:
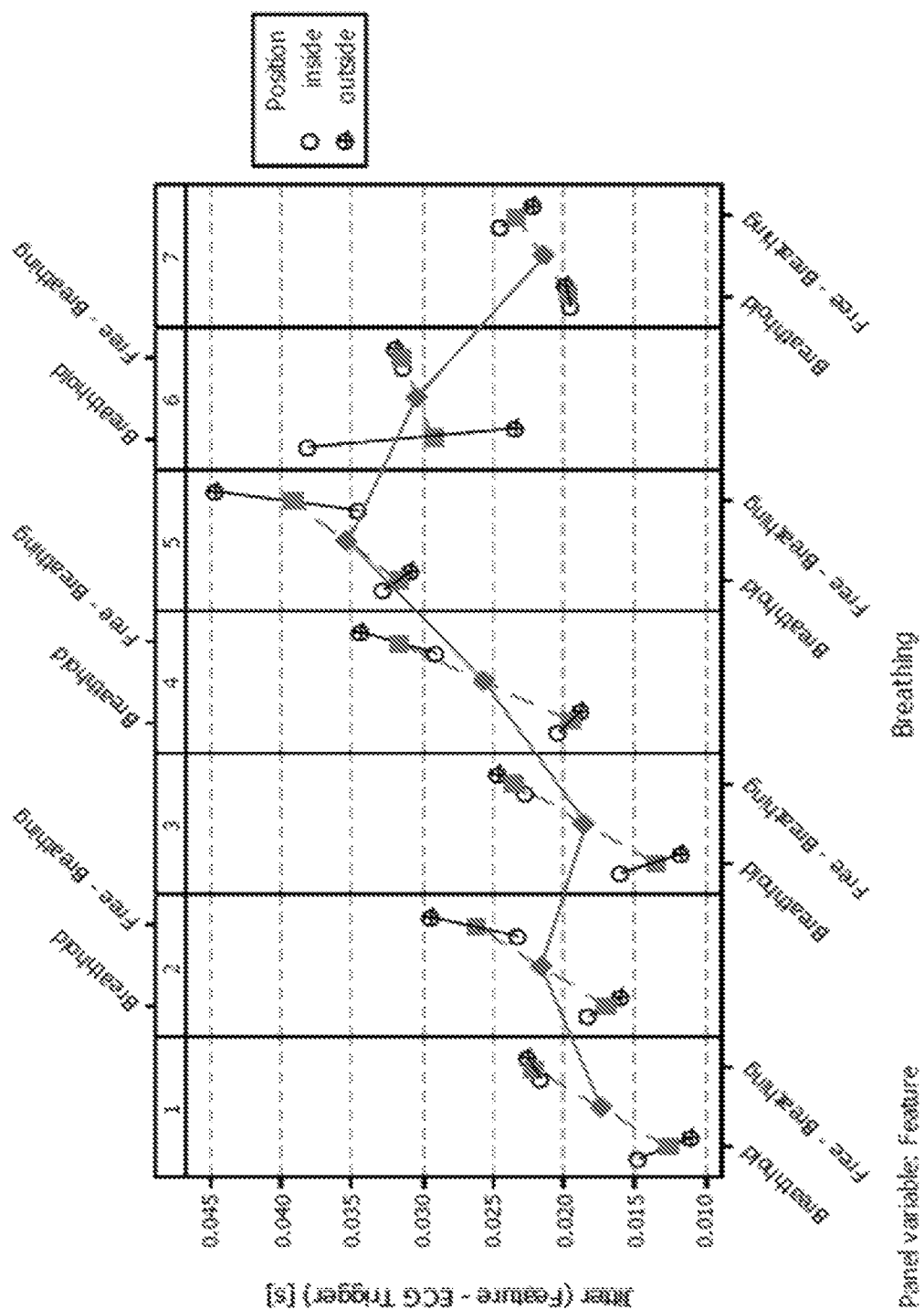
FIG. 3 is a Multi-Vari chart of the jitter of the difference between the features and ECG trigger shown by the different features and breath hold/free-breathing as well as positioning. The lowest mean jitter is achieved for the features 1-3 (main peak detection) during breath hold whereas features 5 and 6 show the highest variance.

The feature detection time was compared to the ECG trigger time as shown in FIG. 3. Breath hold and free breathing data were evaluated separately. The standard deviation of the time difference between the ECG trigger(R) and the corresponding feature(F) was denoted as jitter. The propagation delay between the ECG trigger and the features of the propose method were averaged to a mean trigger delay (MTD). A negative MTD defines a detection before the ECG trigger event.

$$\sigma = \sqrt{\frac{1}{N-1}\sum_{n=1}^{N}((R_n - F_n) - MTD)^2} \qquad (7)$$

$$MTD = \frac{1}{N}\sum_{n=1}^{N}(R_n - F_n) \qquad (8)$$

Further, the detection performance of each feature was evaluated individually by using the sensitivity (Se) and the positive predictive value (PPV) calculated with the equations in Eq. (9) and (10) respectively. Where TP (number of true positives) can define the number of a correctly detected feature and FN (false negatives) the number of missed or false trigger events. Each feature can be assumed to occur exactly one time during a normal heart cycle. Additional feature detection accounted as a false positive (FP) which were assessed by overlaying the ECG trigger events and the extracted cardiac signal.

$$Se = \frac{TP}{TP + FN} \qquad (9)$$

$$PPV = \frac{TP}{TP + FN} \qquad (10)$$

Retrospective, CINE Reconstruction

A 2D-CINE FLASH sequence (slice thickness: 4 mm, TR=2.9 ms, flip angle=12) in the previously describe setup was used to test the proposed method for retrospective cardiac gating. The reflected power was measured by the dico's that captured the data as part of the local SAR monitor and processed in a similar way to using the customized Gaussian pulse sequence. Measuring the reflected voltage on each channel simultaneously without separating scattering from reflection results in a reduced S-matrix or scattering coefficient for the imaging data. All images were acquired in a breath hold on subject 1.

Results

Cardiac Motion Estimation using the Full Scattering Matrix S and ICA

The cardiac motion can be estimated in all acquired datasets during the periods of breath hold as well as during free breathing, inside and outside the MR scanner. The independent component for cardiac information, $\hat{s}_{cardiac}$ was identified correctly in 18 out of 20 datasets using the power spectral density estimation describe in the methods section. The data of subject 2 has shown an unexpected systematic error with an overlaying frequency of exactly 1 Hz which affected the cardiac motion estimation and therefore this subject's data was excluded from further statistical analysis.

Assessment of Trigger Detection Variance

The results of the evaluation of the different features for cardiac gating are shown in FIG. 3 using the mean jitter of the difference between ECG and each feature (Eq. 7,8). The mean jitter in features 1 to 4 is 10.3 ms lower (paired t-test, a=0.01, p<0.001) during breath holds than for free breathing whereas features 5,6,7 showed no significant difference (paired t-test, a=0.01, p=0.09, p=0.27, p=0.11). For detection of features 1-3 has the lowest variation outside the MR-Scanner with a mean jitter of 11.0 ms, 16.0 ms and 11.5 ms respectively, although there was a small increase inside the scanner it was not statistically significant (paired t-test, a=0.01, p=0.66).

Assessment of Trigger Accuracy

The sensitivity and positive predictive value was 100% for features 1-3, the main peak in the cardiac signal with a combined total of 579 trigger events detected. A summary of the results for the other features 4-7 are shown in FIG. 4. The sensitivity (Se) and the positive predictive value (PPV) decreases for the features that aim to detect the Atrial Systole whereas feature 5, which uses wavelets, shows a better performance (Se=96%, PPV=99.9%) than feature 6 which uses first derivatives (Se=94.4%, PPV=94.2). ECG shows a good overall performance, inside and outside the MRI Scanner. Missed ECG trigger (false negatives) were observed in subject 5 and 6 and identified by assessing the extracted cardiac signal.

Figure 5A:
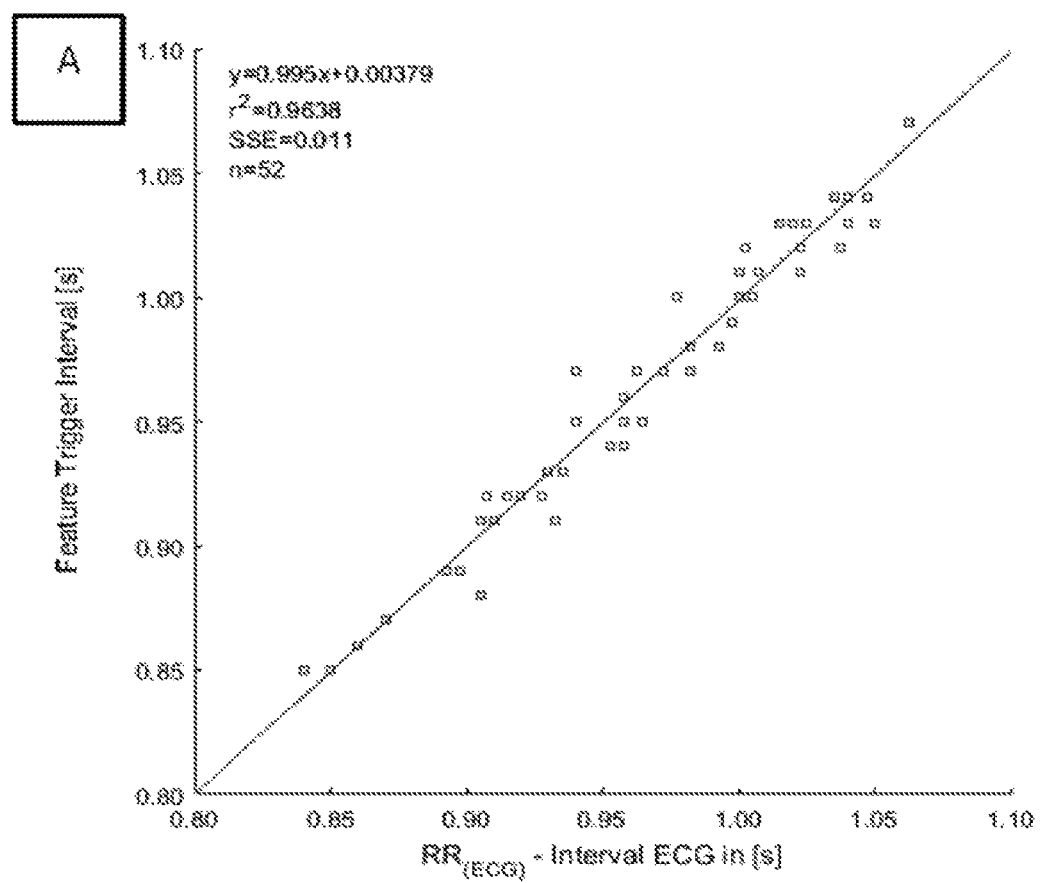
FIG. 5A is a scatter pot of Trigger interval for a subject during breath hold. A strong correlation can be shown between the RR-interval (ECG) and the feature interval.
Figure 5B:
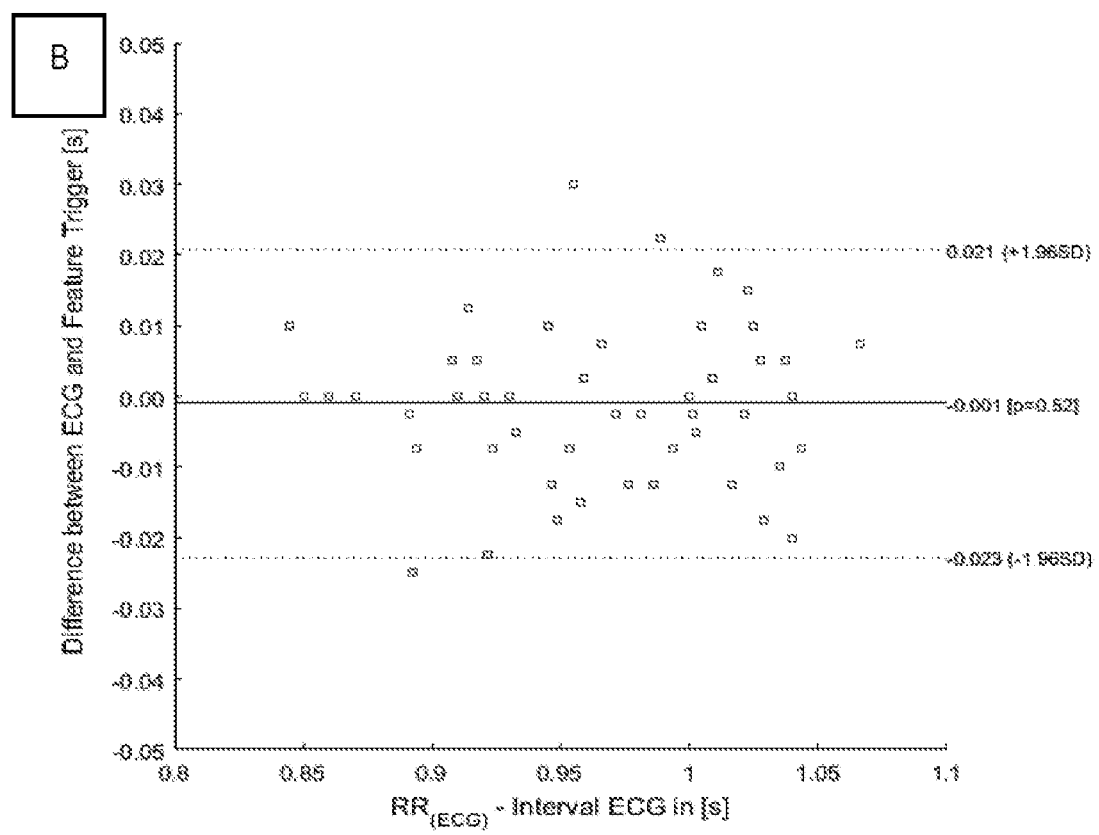
FIG. 5B is a Bland-Altman plot for subject 1 during breath hold. The plot reveals that the feature trigger event can occur within a range of 21 ms after an ECG trigger.

The Bland and Altman Plot [30] in FIG. 5B shows the variation for each cardiac interval between the ground truth, derived from the ECG, compared to the main peak detection (feature 1) using the method on subject 1 during a breath hold. A correlation graph in FIG. 5A between the ECG trigger (RR) and feature 1 intervals, shows a strong correlation with a squared Pearson R-value of 0.96.

Retrospectively Reconstructed 2D-CINE FLASH Imaging at 7.0 T

Figure 6:
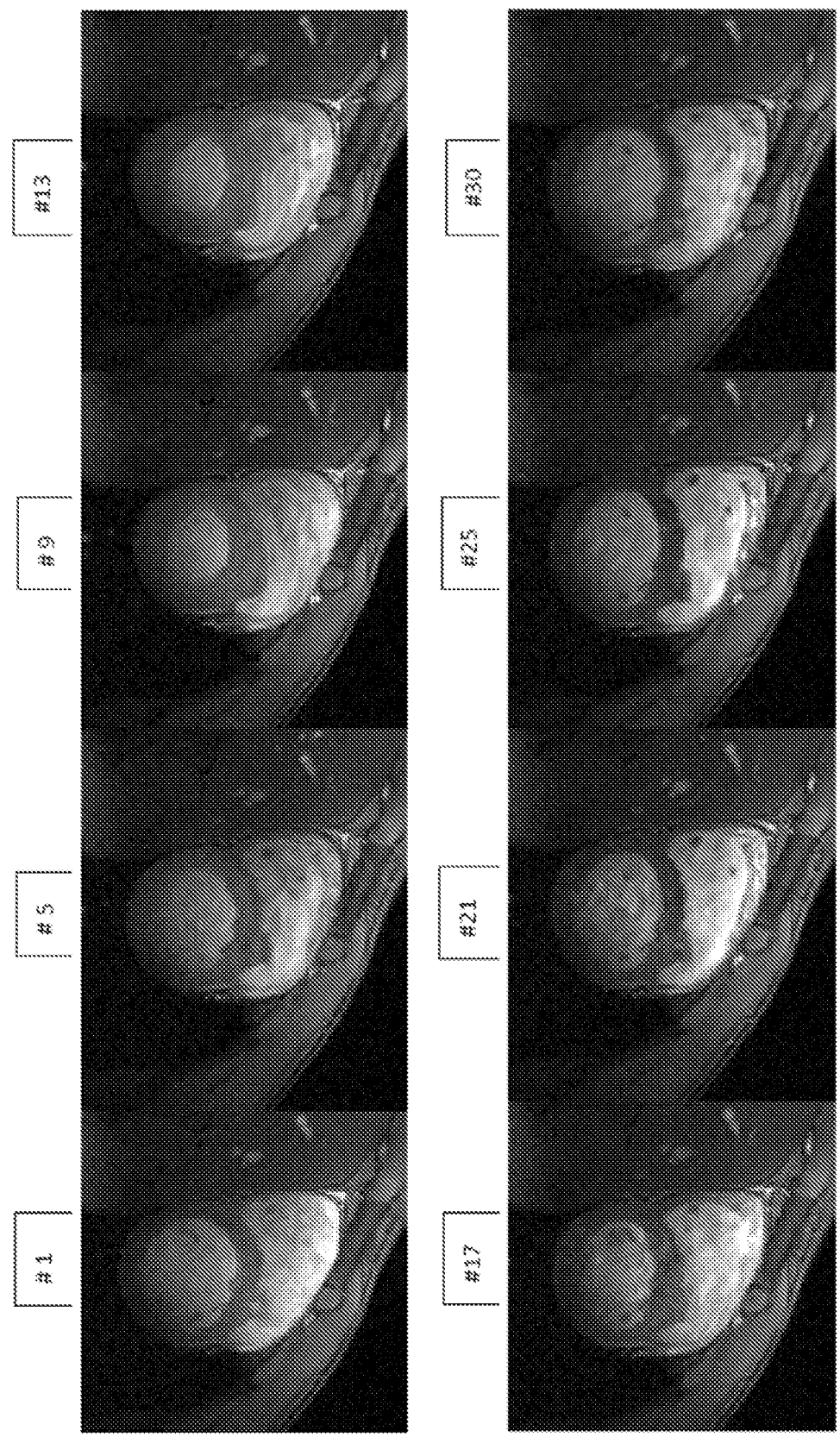
FIG. 6 is a short axis view of a 2D-CINE FLASH acquisition, reconstructed using cardiac trigger from an embodiment of a method at 7 T. The embodiment was used to extract the cardiac information and to assess the signal, Trigger feature 1 (wavelet peak detection) was used to retrospectively gate and reconstruct the CINE data. Images were obtained on subject 1 during breath hold.

Preliminary results for a retrospectively reconstructed 2D-CINE sequence using feature 1 of the proposed method are shown in FIG. 6.

Discussion

The method can achieve an automated estimation of cardiac motion using a full scattering matrix derived from reflected power measurements with the commercial SAR monitor of a 7TMRI. It can be seen that the cardiac motion can be estimated in-vivo during breath hold as well as in free breathing using an independent component analysis. The independent component analysis (ICA) and the automated dimensionality reduction (PCA) provides a robust estimation of underlying cardiac information. The threshold that determines which eigenvalues of the covariance matrix are kept, is a major and crucial parameter in this method.

The analysis showed good performance for detection of the main peak with 100% sensitivity and positive predictive value of 100%, which was better than the vector ECG which missed triggers (compare Table 1 (FIG. 4), subjects 5 and 6 during free breathing). The use of wavelets increases the accuracy and robustness of peak detection and enabled a further extraction of information about the state in the heart cycle (end of diastasis/start of atrial systole) whereas feature 1 shows the best performance in terms of temporal variability compared to vector ECG (overall mean jitter of 12.6 ms). The RR interval was within 21 ms of that calculated with ECG (96% confidence interval) (compare FIG. 5A).

Features 4 and 5, which aim to detect the atrial contraction (corresponding P-wave in the ECG), struggle for a reliable detection in subjects 3 and 5. A closer look at the cardiac information and raw reflected power data on those subjects revealed that the changes due to atrial contraction were around the noise floor of the data. Resulting in a lower sensitivity and positive predictive value for these subjects. Feature 4, which aims to detect the start of the diastasis where the heart is almost at rest, shows a good overall performance and can provide additional information about the cardiac cycle compared to ECG and its single peak detection. Only in subject 6 a lower sensitivity (mean Se=88%) is observed for feature 4, this may be a result of the higher mean heart rate of subject 6 (MHR=79 bpm) which gives rise to a reduced duration of the resting state of the heart and therefore a smaller change in the refilling is observed.

Features detection using the first and second derivatives are sensitive to the choice of an appropriate pre-filtering (Savitzky-Golay in this work) and smoothing. Feature extraction from these derivatives could be improved using a priori knowledge about the appearance of each feature so that false negatives can be avoided or further reduced.

The suitability of this method for cardiac gating at 7T has been shown with preliminary results on retrospectively gated 2D-CINE images. The images were acquired without any further external hardware nor sequence changes. This makes the proposed method unique compared to other cardiac triggering methods such as acoustic cardiac triggering [10], navigator pulse sequences approaches [9] or the use of additional RF sources [13]. It further speeds up the whole MRI scan as no additional preparation of the subject or the scanner set up is needed.

In an aspect, the potential of this method lies in an introduction of a training period to determine the demixing vector w before starting the actual image acquisition. This can lead the method from a retrospective analysis and gating tool towards a cardiac triggering method used during MR acquisitions.

Conclusions

A novel, robust estimation of cardiac motion at 7T MRI, using the multi-channel transmit coil and an independent component analysis (ICA), is presented. Shown for the first time is that the reflected power can be measured from directional couplers of the local SAR monitor and a full scattering matrix of the pTX coils can be calculated by applying a customized Gaussian RF-pulse sequences.

A set of different features were derived from the cardiac motion estimation and assessed for their applicability for gating in CMR. The three, main peak detection methods showed a good performance and can be used for cardiac gating and possibly outperform VCG inside a 7T MRI in terms of sensitivity.

Preliminary results on a 2D-CINE image reconstruction show the feasibility of cardiac gating using the present method. This provides a new approach of improving cardiac imaging at ultra-high field CMR by providing robust triggering as well as in workflow and application as no professional setup or changes in MR-Scanner hardware and sequences are needed.

REFERENCES

[1] T. Niendorf, D. K. Sodickson, G. A. Krombach, and J. Schulz-menger, "Toward cardiovascular MRI at 7 T: clinical needs, technical solutions and research promises," *Eur Radiol*, vol. 20, no. 12, pp. 2806-2816, 2011.

[2] T. Niendorf, K. Paul, C. Oezerdem, A. Graessl, S. Klix, T. Huelnhagen, F. Hezel, J. Rieger, H. Waiczies, J. Frahm, A. M. Nagel, E. Oberacker, and L. Winter, "W(h) ither human cardiac and body magnetic resonance at ultra-high fields? Technical advances, practical considerations, applications, and clinical opportunities," *NMR Biomed.*, vol. I, no. October 2014, 2015.

[3] V. Martin, A. Drochon, O. Fokapu, and J. F. Gerbeau, "Magnetohemodynamics effect on electrocardiograms," *Lect. Notes Comput. Sci. (including Subser. Lect. Notes Artif. Intell. Lect. Notes Bioinformatics)*, vol. 6666 LNCS, pp. 325-332, 2011.

[4] Y. Kinouchi, H. Yamaguchi, and T. Tenforde, "Theoretical analysis of magnetic field interactions with aortic blood flow," *Bioelectromagnetics*, vol. 32, pp. 21-32, 1996.

[5] T. Togawa, O. Okai, and M. Oshima, "Observation of blood flow E.M.F. in externally applied strong magnetic field by surface electrodes," Med, Biol, Eng., vol, 5, no. 2, pp. 169-170, 1967.

[6] J. J. Suttie, L. Delabarre, A. Pitcher, P. F. van de Moortele, S. Dass, C. J. Snyder, J. M. Francis, G. J. Metzger, P. Weale, K. Ugurbil, S. Neubauer, M. Robson, and T. Vaughan, "7 Tesla (T) human cardiovascular magnetic resonance imaging using FLASH and SSFP to assess cardiac function: Validation against 1.5 T and 3T," NMR Biomed., vol. 25, no. 1, pp. 27-34, 2012.

[7] S. E. Fischer, S. A. Wickline, and C. H. Lorenz, "Novel real-time R-wave detection method based on the vectorcardiogram for accurate gated magnetic resonance acquisitions," Magn. Reson. Med., vol. 42, no. 2, pp. 361-370, 1999.

[8] F. S. E. Chia J M Wickline S A, Lorenz C H, "Performance of QRS detection for cardiac magnetic resonance imaging with a novel vector cardiographic triggering method," J Magn Reson Imaging, vol, 688, pp. 678-688, 2000.

[9] T. Zhang, J. Y. Cheng, Y. Chen, D. G. Nishimura, J. M, Pauly, and S. S. Vasanawala, "Robust self-navigated body MRI using dense coil arrays," Magn. Reson. Med., vol. 00, 2015.

[10] T, Frauenrath, F. Hezel, W. Renz, T. de G. d'Orth, M. Dieringer, F. von Knobelsdorff-Brenkenhoff, M. Prothrnann, J. Schulz Menger, and T. Niendorf, "Acoustic cardiac triggering: a practical solution for synchronization and gating of cardiovascular magnetic resonance at 7 Tesla," J. Cardiovasc. Magn. Reson., vol, 12, no. 1, p. 67, 2010.

[11] P. Speier, M. Fenchel, and R. Rehner, "PT-Nay: a novel respiratory navigation method for continuous acquisitions based on modulation of a pilot tone in the MR-receiver," in ESMRMB, 129:97-98, 2015.

[12] L. Schroeder, J. Wetzl, A. Maier, R. R. Rehner, M. Fenchel, and P. Speier, "Two-Dimensional Respiratory-Motion Characterization for Continuous MR Measurements Using Pilot Tone Navigation," in Proc. Intl. Soc. Mag. Reson. Med. 24, 2016, p. 3103.

[13] L. Schroeder, J. Wetzl, A. Maier, L. Lauer, J. Bollenbeck, M. Fenchel, and P. Speier, "A Novel Method for Contact-Free Cardiac Synchronization Using the Pilot Tone Navigator," in Proc. Intl. Soc. Mag. Reson. Med. 24, 2016, p, 0410.

[14] A. Stecco, A. Saponaro, and A. Carriero, "Patient safety issues in magnetic resonance imaging: state of the art.," Radiol. Med., vol. 112, no. 4, pp. 491-508, 2007.

[15] H. Kugel, C. Bremer, M. Püschel, R. Fischbach, H. Lenzen, B. Tornbach, H, Van Aken, and W. Heindel, "Hazardous situation in the MR bore: induction in ECG leads causes fire.," Eur. Radiol., vol. 13, no. 4, pp. 690-694, 2003.

[16] D. Buikman, T. Helzel, and P. Roeschmann, "The rf coil as a sensitive motion detector for magnetic resonance imaging," Magn. Reson. Imaging, vol. 6, no. 3, pp. 281-289, 1988.

[17] A. C. S. B. Guido P. Kudielka, Christopher J. Hardy, Pierre-André Vuissoz, Jacques Felblinger, "Utilization of the receive coil for cardiovascular and respiratory motion representation," in Proc. Intl. Soc. Mag. Reson. Med. 23 (2015) 0705., 2015, vol. 2, p. 2015.

[18] I. Graesslin, G. Mens, A. Guillaume, H. Stahl, P. Koken, P. Vernickel, P. Harvey, J. Smink, K. Nehrke, and P. Boernert, "Advancements in Contact-free Respiration Monitoring using RF Pick-up coils," Proc. 18th Sci. Meet. Int. Soc. Magn. Reson. Med., vol. 47, no, 2, p. 3045, 2010.

[19] E. C. Burdette, F. L. Cain, and J. Seals, "In Vivo Probe Measurement Technique for Determining Dielectric Properties at VHF Through Microwave Frequencies," IEEE Trans. Microw. Theory Tech., vol. 28, no. 4, pp. 414-427, 1980.

[20] J. T. Vaughan and C. A. Lemaire, "Method and coils for human whole-body imaging at 7 t," US 2012/0032678 A1, 2012,

[21] S. Butterworth, "On the theory of filter amplifiers," in Experimental Wireless and the Wireless Engineer, 1930, pp. 536-541.

[22] A. Hyvärinen, "Fast and Robust Fixed-Point Algorithm for Independent Component Analysis," IEEE Trans. Neur. Net., vol. 10, no. 3, pp. 626-634, 1999.

[23] H. Gävert, J. Hurri, J. Särelä, and A. Hyvärinen, "FastICA package for MATLAB." Helsinki University of Technology, Helsinki, 2005.

[24] P. D. Welch, "The Use of Fast Fourier Transform for the Estimation of Power Spectra: A Method Based on Time Averaging Over Short, Modified Periodograms," IEEE Trans. Audio Electroacoust., vol. 15, no. 2, pp. 70-73, 1967.

[25] S. P. Lloyd, "Least Squares Quantization in PCM," IEEE Trans. Inf. Theory, vol, 28, no. 2, pp, 129-137, 1982,

[26] S. Arthur, D.; Vassilvitskii, "K-means++: The advantages of careful seeding," in Proceedings of the Annual ACM-SIAM Symposium on Discrete Algorithms, 2007.

[27] D. B. Percival and A. T. Walden, Wavelet methods for time series analysis. Cambridge University Press, 2000.

[28] P. Abry, Ondelettes et turbulence. Multirésolutions, algorithmes de décomposition, invariance d'échelles. Paris, 1997.

[29] A. Savitzky and M. J. E. Golay, "Smoothing and Differentiation of Data by Simplified Least Squares Procedures," Anal. Chem., vol. 36, no. 8, pp. 1627-1639,1964.

[30] J. M. Bland and D. G. Altman, "Statistical methods for assessing agreement between two methods of clinical measurement," Int. J. Nurs. Stud., vol. 47, no. 8, pp, 931-936, 2010.

Example 2

Synopsis

The reflected power of transmit RF coils can also be influenced by the position of the diaphragm. In this example the diaphragm position is measured in real-time for every RF pulse with a hybrid approach. The set of scattering coefficients are transformed into a diaphragm position using a series of MR diaphragm navigators at the start of the pulse sequence in a learning cycle. High quality respiratory gated data based on gating via this mechanism using standard SAR monitoring hardware with a real-time lag of 23 ms and temporal resolution of 4.5 ms are demonstrated.

Background

The electrical characteristics of RF coils can be affected by the objects they couple to. This has been used to detect respiratory and cardiac motions [31,32]. Shown in this example is that by using vendor provided parallel transmit (PTX) SAR monitoring hardware (Siemens 7T) the reflected power can be monitored on every RF pulse and this measurement can be related to motion using MR images. This strategy uses an MR image based learning interval to provide a hybrid method to quantify in real-time the diaphragm position at a 4.5 ms (image TR) temporal resolution.

Methods

The Siemens 71 PTX local SAR monitor samples the forward and reflected power of all RF pulses on each transmit channel via directional couplers that are then digitized by the imager. A programme was written on the image reconstruction computer to calculate scattering coefficients $S'_i$ at the end of each RF pulse on all eight transmit channels. $S'_i$ is defined as the ratio of forward to returned voltage on each transmit line. A change in $S'_i$ can occur when the diaphragm changes position, this $S'_i$ change can then be transformed into a quantitative diaphragm position using a series of MR images to measure the diaphragm position during an initial learning interval.

To assess the method two experiments were setup on a human 7T scanner (Siemens). The first (experiment 1), to assess the accuracy of the diaphragm position, and the second to evaluate whether this operates effectively within a real-time cardiac cine acquisition. Five healthy volunteers were scanned according to the appropriate institutional ethical guidelines. A sagittal gradient echo (GRE) acquisition placed over the right hemi-diaphragm with a TR/TE of 4.5/1.9 ms, image matrix of 304×156, resolution of 1.0 (HF)×1.9 mm (AP), and flip angle ~2° was conducted. The image was repeated 513 times every 321 ms for 2 min 45 s. The eight complex $S'_i$ values were calculated from the central 10 ps of each RF pulse. The diaphragm edge was measured in each image. The first 20 s of measurements were used as a learning cycle by performing a linear regression between the set of $S'_i$ and the diaphragm edge. In the regression the complex $S'_i$ was separated into real and imaginary components. One image, every 8 s, was used as an absolute position reference to remove effects of systematic drift in $S'_i$.

Figure 7:
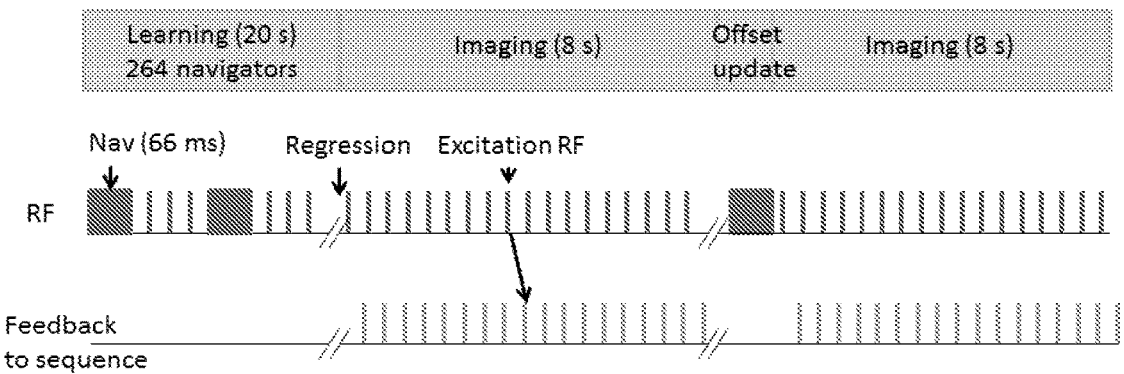
FIG. 7 illustrates a timing schematic for a diaphragm navigated pulse sequence according to an embodiment of the present disclosure.

In the second experiment (experiment 2) a pulse sequence was constructed to include a diaphragm image GRE navigator [33] that runs repeatedly for 20 s at the start of the sequence with three dummy excitation pulses between each navigator. After this the navigator was repeated every 8 s to measure and account for systematic drift in $S'_i$ (as illustrated FIG. 7). FIG. 7 shows a timing schematic for the diaphragm navigated pulse sequence, with a 20 s learning cycle consisting of 264 repeated GRE navigators, each of 66 ms duration. The diaphragm position is calculated and provided to pulse sequence for every imaging RF pulse. The navigator duration was 66 ms, resolution of 1.4 mm (HF)×15 mm (AP), slice thickness of 15 mm, flip angle ~2°. The position of the diaphragm was determined using the method above and used with a 5 mm window to prospectively respiratory gate the acquisition. A non-gated acquisition was acquired for comparison. A retrospectively ECG gated cine was acquired. Flip angle 12°, FOV 320×300, resolution 1.4× 1.4×8 mm³, TRITE 5.8/3.06 ms, bandwidth of 744 Hz/pix, and a temporal resolution of 52 ms. A Kalman filter was implemented in both experiments to increase the confidence when an offset is applied.

Results

Figure 8:
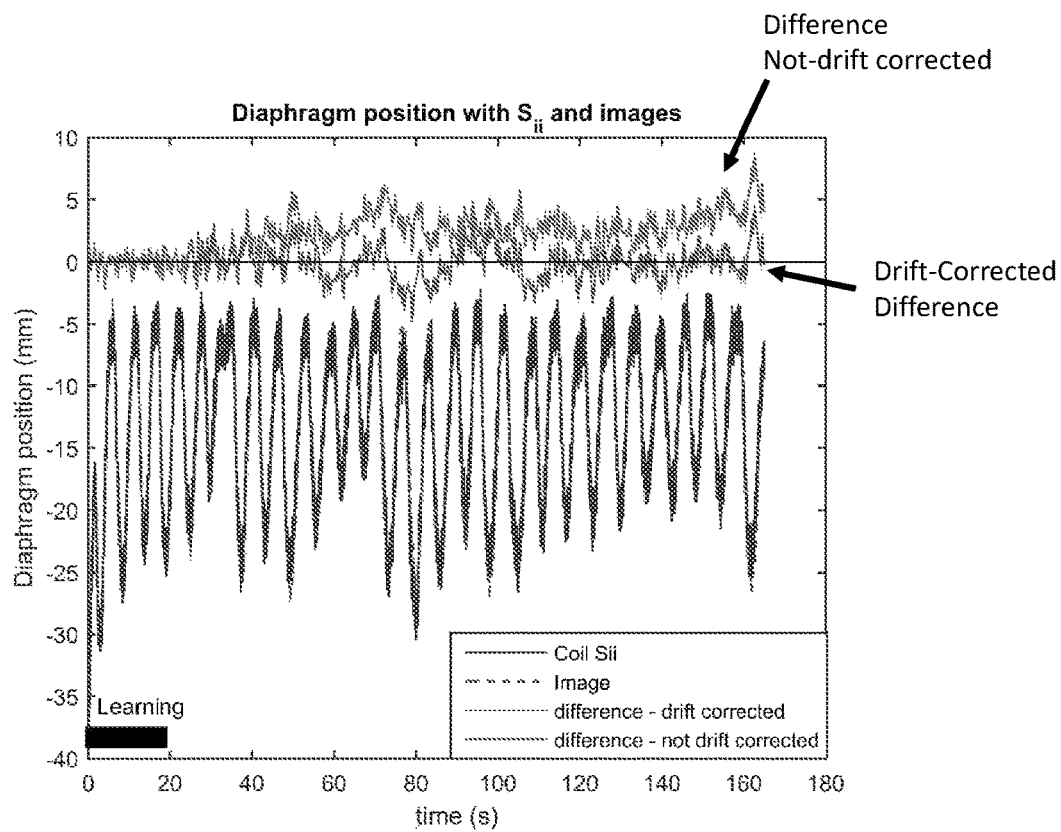
FIG. 8 is a trace of diaphragm position measured for every RF pulse using the coil reflection and measured with GRE images acquired with those RF pulses.
Figures 9, 10:
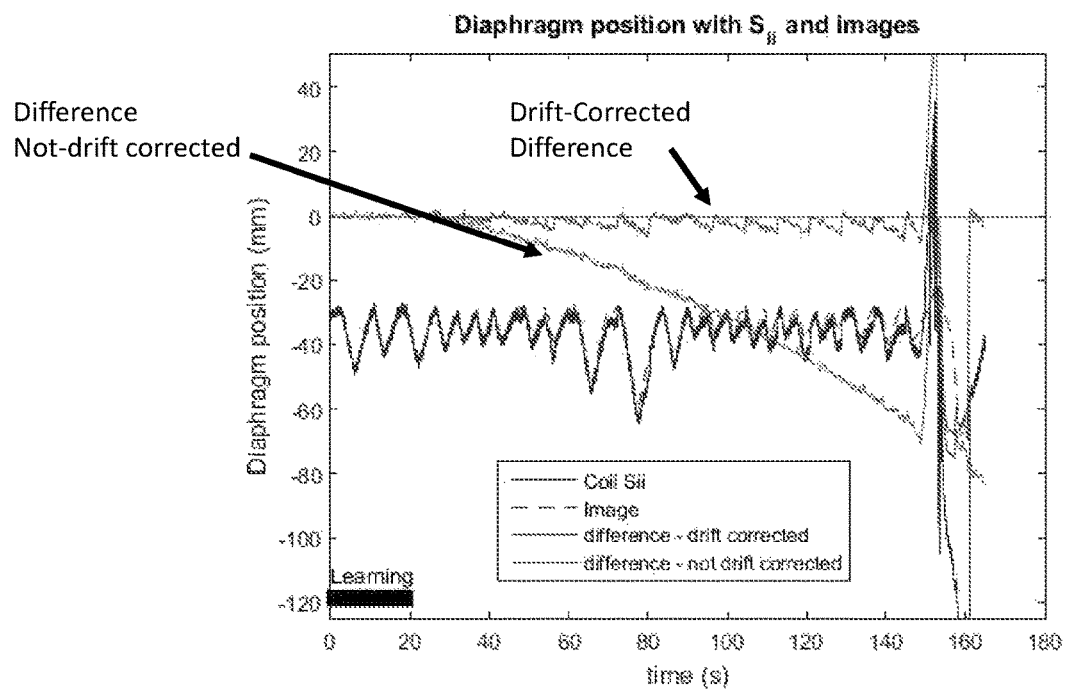
FIG. 9 is a trace from a subject showing a large system drift tracked by 8 s updates.
FIG. 10 shows differences between diaphragm predictions with coil reflection to that measured in the images.

For experiment 1: FIG. 8 and FIG. 9 show representative traces of the diaphragm position measured with the $S'_i$ method compared to that measured in the images for subjects 3 and 2 respectively, FIG. 10 lists the mean±standard deviation of the difference between the $S'_i$ diaphragm position and that measured in the images without filtering. The last column of the table of FIG. 10 shows the accumulated system drift over the scan, FIG. 8 shows a trace of diaphragm position measured for every RF pulse using the coil reflection and measured with GRE images acquired with those RF pulses. No filtering is performed for this plot. The difference between these measures is plotted for both drift corrected data and non-drift corrected data. FIG. 9 shows a trace from a subject showing a large system drift which is tracked by the 8 s updates at the end of a large change is shown in both the reflection and image based measures, possible the subject was coughing or moving.

Figure 11:
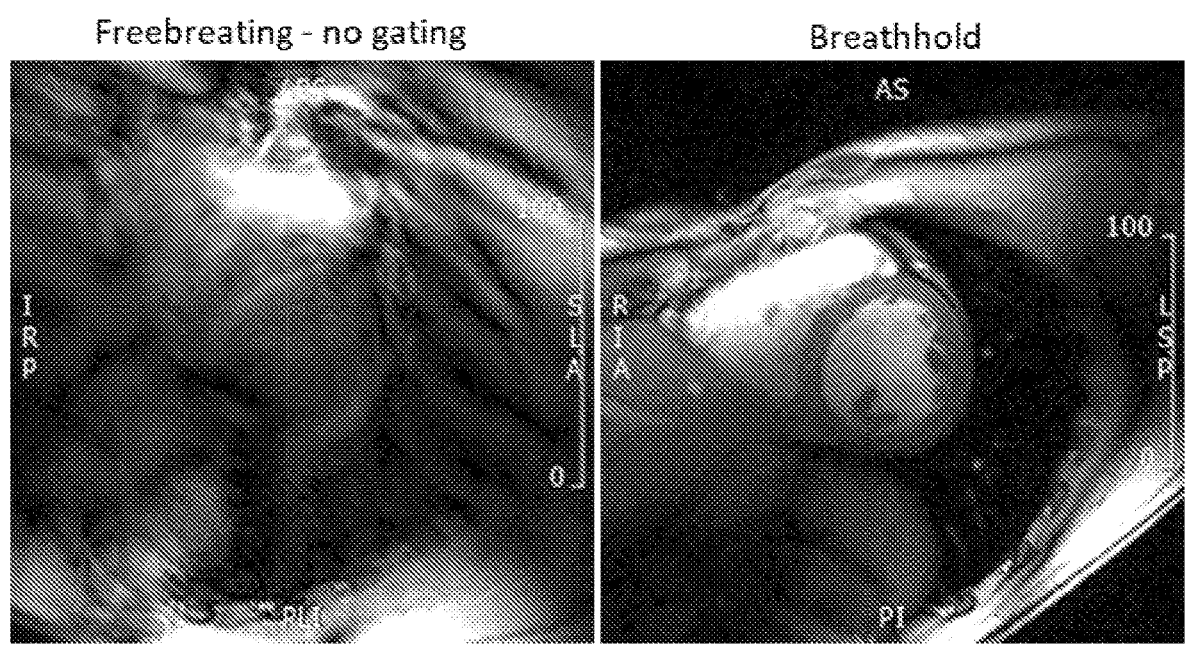
FIG. 11 shows two retro-gated cine cardiac short axis images, one acquired with no diaphragm-gating and the second with diaphragm-gating with a 5 mm acceptance window at end expiration.

For experiment 2: FIG. 11 shows a single cardiac cine frame for non-diaphragm-gated and diaphragm-gated cine acquisitions. There was a delay of 23 ms due to processing and networking constraints between measurements of the diaphragm position and updating the RF and gradient waveforms. The mean and standard deviation (SD) of the difference between diaphragm predictions with coil reflection to that measured in the images is shown. The drift, as measured in each of the 8 s updates is shown in FIG. 9.

FIG. 11 shows two retro gated cine cardiac short axis images, one acquired with no diaphragm-gating and the second is diaphragm-gated with a 5 mm acceptance window at end expiration.

Discussion and Conclusion

For all subjects except the outlier subject 2, the mean±SD of the difference between the image and $S'_i$ prediction was −0.1±1.2 mm. For subject 2, the trace of whom is shown in FIG. 9, both the image and measures indicate a large unusual motion, perhaps representing coughing at the end of the scan.

This method poses a number of benefits over conventional respiratory monitoring, i) it requires no additional hardware as it uses the existing RF coils and SAR monitoring hardware, ii) the pulse sequence maintains a steady state, iii) diaphragm positions are known with a real-time lag of 23 ms.

In conclusion, real-time diaphragm navigation has been demonstrated using vendor provided PTX local SAR monitoring hardware complemented by a position learning phase then infrequent navigator images.

REFERENCES

[31] Buikman, D., Helzel, T., Röschmann, P. The RF coil as a sensitive motion detector for magnetic resonance imaging. Magn. Reson. Imaging. 1988; 6:281-289.

[32] Kudielka G P, Hardy C J, Vuissoz P, Felblinger J, Brau A. "Utilization of the Receive Coil for Cardiovascular and Respiratory Motion Representation". ISMRM 2015 pp 705.

[33] Hess A T, van der Kouwe A J W, Tisdall M D, Neubauer S, and Robson M D. "2D Diaphragm Navigation with Rapid Gradient Echo Images: Validation at 3T and Application at 7T", ISMRM 2015, pp 2565.

Example 3

Described in this example is a novel contact free diaphragm monitor that measures during the RF transmit pulse providing rapid, quantitative and accurate monitoring of respiration. Respiratory motion remains a limiting factor in abdominal MRI. A novel method is described herein that can utilize RF safety measurements made by a commercial parallel transmit (PTx) scanner to measure the diaphragm position. The method is based on a PTx RF coil being a multi-port RF network interconnected via the subject with the properties of the network changing as a result of respiration and observed in the scatter-matrix.

A calibration phase where both scatter and diaphragm position are measured can be used to determine a mixing vector that maps the RF scatter to diaphragm position. For each subsequent RF pulse, the diaphragm position can be determined via RF scatter alone. The method was validated against MR imaging of the diaphragm in seven healthy subjects and evaluated in a free breathing cardiac cine.

The 95% confidence interval was about ±2.2 mm compared to the MRI diaphragm position. The differences were dominated by slowly varying effects from respiration, the cardiac cycle (±0.8 mm confidence interval), and imaging gradients (±0.2 mm confidence interval). The free breathing cine showed little to no respiratory artefact and sharp myocardial definition.

A number of solutions exist to limit the effects of respiratory motion in abdominal MRI, Existing methods can broadly be categorised into breath-hold methods [34,35] and respiratory resolved methods [36-38]. While breath-holding remains the mainstay the acquisition duration is limited to less than 15 s. The alternative is to resolve the respiratory cycle which can come with a trade-off between introducing a sequence design constraint, such as a navigator echo [36,39] and encoding strategies with self-gating attributes [37], or the use of a bellows that lacks the quantitative aspect of respiratory resolution [38,40,41]. Here we introduce a new method that is rapid, has no sequence design constraint, can be implemented using existing manufacture product parallel transmit (PTx) hardware, and provides a quantitative measure of respiration.

The system can utilize forward and return voltages measured by the local SAR monitor on a commercial PTx system to provide a measure of the diaphragm position in real time. The use of the transmit coil to measure respiration is not new, Buikman reported its use in 1988 [42], however the introduction of PTx with advanced RF monitoring hardware as described herein means that not only is this information readily available in real time but there are now multiple transmit coils providing multiple parallel observations. As described herein, methods are introduced to measure the diaphragm position from the scatter of an RF pulse on a PTx scanner.

Background

Figure 12A:
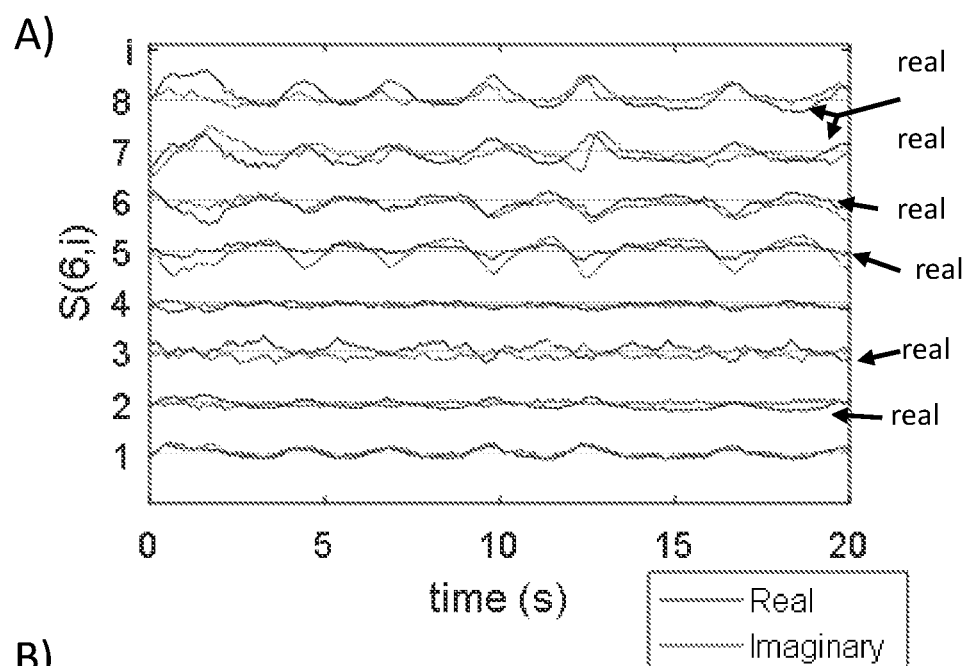
FIGS. 12A-12B show an excerpt of an S-matrix during free breathing plotted against time. The measure was acquired on a subject at 297 MHz using the body array described below. Real (lines labeled) and imaginary (lines not labeled) components exhibit independent sensitivities.
Figure 12B:
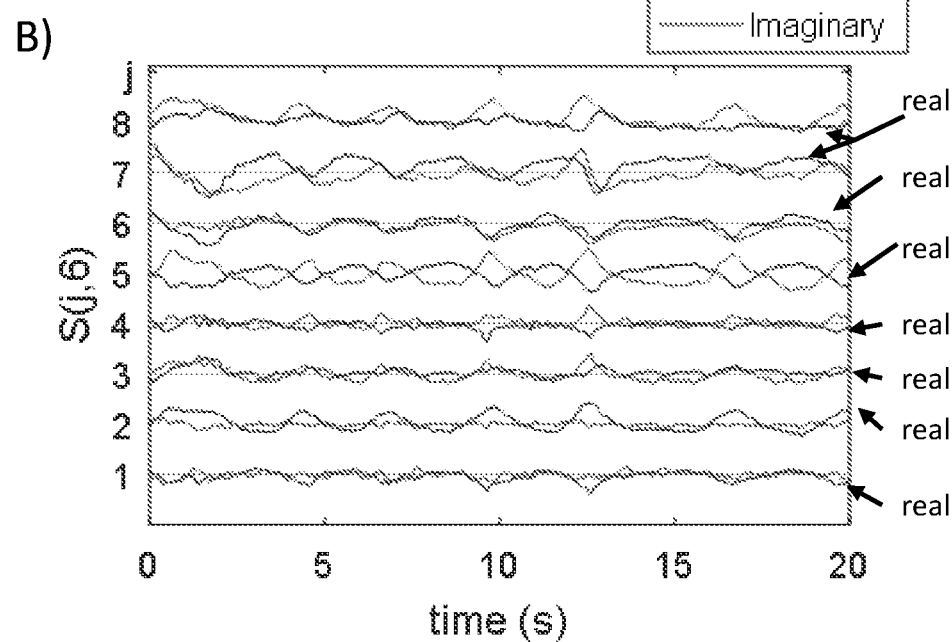

In PTx, the RF coil can be considered to be an N-port electrical network, where N is the number of transmit channels, this network has N inputs and N outputs, and the relationship between the ports is referred to as scattering and measured by the scattering-matrix, S-matrix or S. The diagonal of the S-matrix is the reflection coefficient while the remaining terms are the cross terms or coupling. The load of this network is the subject in the scanner which is a composite of multiple tissue types, each characterised electrically by their complex permittivity at the frequency of interest [43]. When respiration is present the changing air content of lungs results in changing of their complex permittivity [44] and ultimately a change in the port-to-port load of the network. The reflection coefficient (diagonal of S) has a well-known relationship to the load on a port (admittance as observed from the transition line). A recording of the S-matrix over 20 s of free breathing at 297 MHz is plotted in FIGS. 12A-12B from two perspectives, one when channel 6 is the destination port and one where channel 6 is the source port. FIGS. 12A-12B show an excerpt of an S-matrix during free breathing plotted against time. The measure was acquired on a subject at 297 MHz using the body array described below. Real and imaginary components exhibit independent sensitivities. The first row shows the RF returned to channel 6 from all channels (i=1 to 8). The second row shows all RF originating from channel 6 returned to channels (j=1 to 8). This further demonstrates how the complex nature of scattering results in two different measures one real and one imaginary.

For an RF excitation with a static PTx B1+ shim, the RF returned on all ports ($V_{ret}(t)$) is the product of the S-matrix ($S(t)$) and complex forward voltages as set by the B1+ shim ($V_{fwd}(t)$), as in equation 1.

$$V_{ret}(t) = S(t) V_{fwd}(t) \quad [1]$$

Methods

Setup

Figure 13:
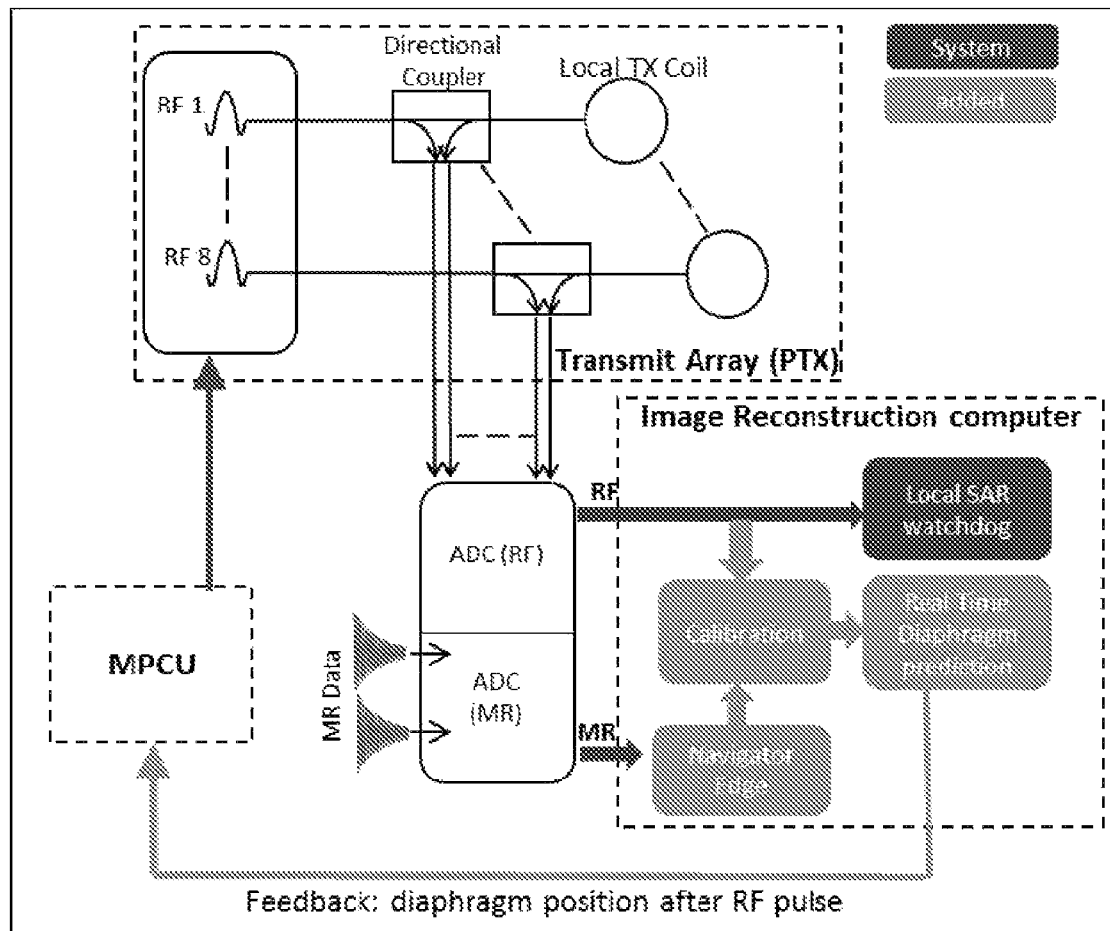
FIG. 13 is a schematic showing an embodiment of a system of the present disclosure. Methods as disclosed herein can be implemented on a system such as this.

All experiments were carried out on a Magnetom 7T (Siemens, Erlangen Germany) equipped with an 8 channel PTx and local SAR monitor (VB17 step 2.3). The local SAR monitor comprises of eight directional couplers, one for each transmit channel that monitor the forward and returned RF voltage on each transmit channel. They are demodulated by the carrier frequency and connected to the MR receivers' analogue to digital converter that digitizes them at 1 MHz during all RF transmissions. The digitized voltages are delivered in real time to the local SAR monitor, this is summarised in FIG. 13. FIG. 13 is a schematic showing components of a local SAR monitor and added software components. A local transmit receive RF coil was custom built using the transmission line or TEM method [45-48], it comprises 4 elements positioned posteriorly and 4 anteriorly, each element 15 cm long and separated by 50 mm centre to centre and positioned for maximum coverage of the heart.

Method

An S-matrix, $S(0)$, is measured prior to the acquisition and used to calculate an expected returned voltage, $V_{exp}(t)$, this will differ from the measured returned voltage at time t if $S(t)$ has changed. The ratio of return to expected return is taken for each channel as in equation 4 where k identifies an RF pulse and $t_k$ is the time of the peak of that pulse in µs and i the channel.

$$V_{exp}(t) = S_{exp} V_{fwd}(t) \quad [2]$$

$$\Gamma_{i,k} = \frac{\int_{-25}^{25} V_{ret,i}(t_k + \tau) \delta\tau}{\int_{-25}^{25} V_{exp,i}(t_k + \tau) \delta\tau} \quad [3]$$

This step takes into account variations in gain and noise from one amplifier to another. Using $\Gamma_{i,k}$, a 16 element vector $\Gamma_k$ can be formed by separating the real and imaginary components of $\Gamma_{i,k}$. The diaphragm position measured by the scattering during an RF pulse k is $d_k$ and determined by equation 5 where M is a mixing vector and c a constant offset.

$$d_k = \Gamma_k M + c \quad [4]$$

The mixing vector and constant (M and c, respectively) can be determined in a calibration where the diaphragm position is measured with MRI and $\Gamma_k$ is recorded for each diaphragm image. A least squares optimisation (linear regression) can be carried out to find the optimal mixing vector such that it predicts the diaphragm position.

Validation

To evaluate the accuracy and precision of methods as described herein, seven healthy male volunteers were recruited according to the appropriate institutional ethical practices. A B1+ shim was applied to maximise the minimum B1+ over the edge of the diaphragm for both inspiration and expiration [49]. A sagittal spoiled gradient echo (SPGR) image was setup through the right hemi-diaphragm from which both a diaphragm image and $\Gamma$ can be determined. The SPGR had a flip angle between 2° and 10°, a train of 71 sinc RF pulses of 1 ms long, a TR/TE of 5/2 ms, GRAPPA iPAT factor of 2 and 6:8 phase partial Fourier, matrix size of 304×156, FOV of 300×300 mm² for a total acquisition duration of 322 ms, repeated for 2 min 45 s (513 measurements).

The diaphragm images along with digitized forward and returned RF voltages were processed in Matlab (MathWorks, Natick, Ma.) according to the above steps. The diaphragm position in the images was determined using an edge detection and up-sampled to the RF pulse rate using a linear interpolation. The first 30 s of data (93 images) were used for calibration and the remaining 420 were used for evaluation.

To understand the nature of differences of the scattering measure to the MRI diaphragm position, a frequency analysis was performed on the difference for each subject. This was done with a Fourier transform of the difference followed by a Hanning apodization of 0.15 Hz. A scaling factor was used to take account of the apodization line width and frequency bin size to give units of oscillation amplitude in millimetres.

One subject was asked to cough four times during the acquisition after the initial 30 s calibration phase to evaluate the response and response time of the system to non-periodic respiration. For this assessment a Kalman filter [50] was used to estimate diaphragm velocity from both the scattering and image based diaphragm positions. The Kalman filter gain ($\Delta^*$) was 2.9 s$^{-1}$ for velocity and 0.16 for position. Velocities out of the standard range (−25 mm/s to 25 mm/s) are taken to be the start of coughing.

Real-Time Pulse Sequence

To evaluate the practicality of these methods for online, real time, respiratory state detection, a pulse sequence was developed that contained a SPGR diaphragm navigator [51] that was repeatedly acquired for 30 s at the start of an acquisition. The navigator had a matrix size of 210×21, FOV of 300×300 mm, slice thickness of 13 mm, TR/TE 3.5/1.5 ms. Three imaging RF pulses were inserted between each navigator to measure $\Gamma$, this was to allow the navigator and target imaging RF pulses to have different B1+ shims. For cardiac imaging a cine pulse sequence was developed that could open or close a respiratory driven gate independently for each TR as determined by the diaphragm position measured from scatter ($d_k$). To ensure synchronisation between all measurement and physiological control units (MPCU's) of the PTx, a feedback queue was implemented. This queue ensured that all MPCU's acted on the same feedback which contained both the diaphragm position as measured from scatter and time from last ECG event.

The above method was implemented on the scanner's image reconstruction system. This consisted of an image reconstruction and edge detection for the navigator images, a functional unit to perform the calibration and the online calculation of the diaphragm position from scattering that is transmitted back to the MPCUs of the PTx. These components are shown as "added" in FIG. 13.

A 2D cine SPGR pulse sequence was setup with B1+ shims set for the right hemi-diaphragm and right side of the heart for the navigator and image respectively, A +/−3 mm acceptance window at end expiration, flip angle of approximately 10°, TRITE 5/2 ms, matrix 304×256, field of view 300×253 mm and 29 ms per cardiac phase and slice thickness of 3 mm.

Results

Figure 14:
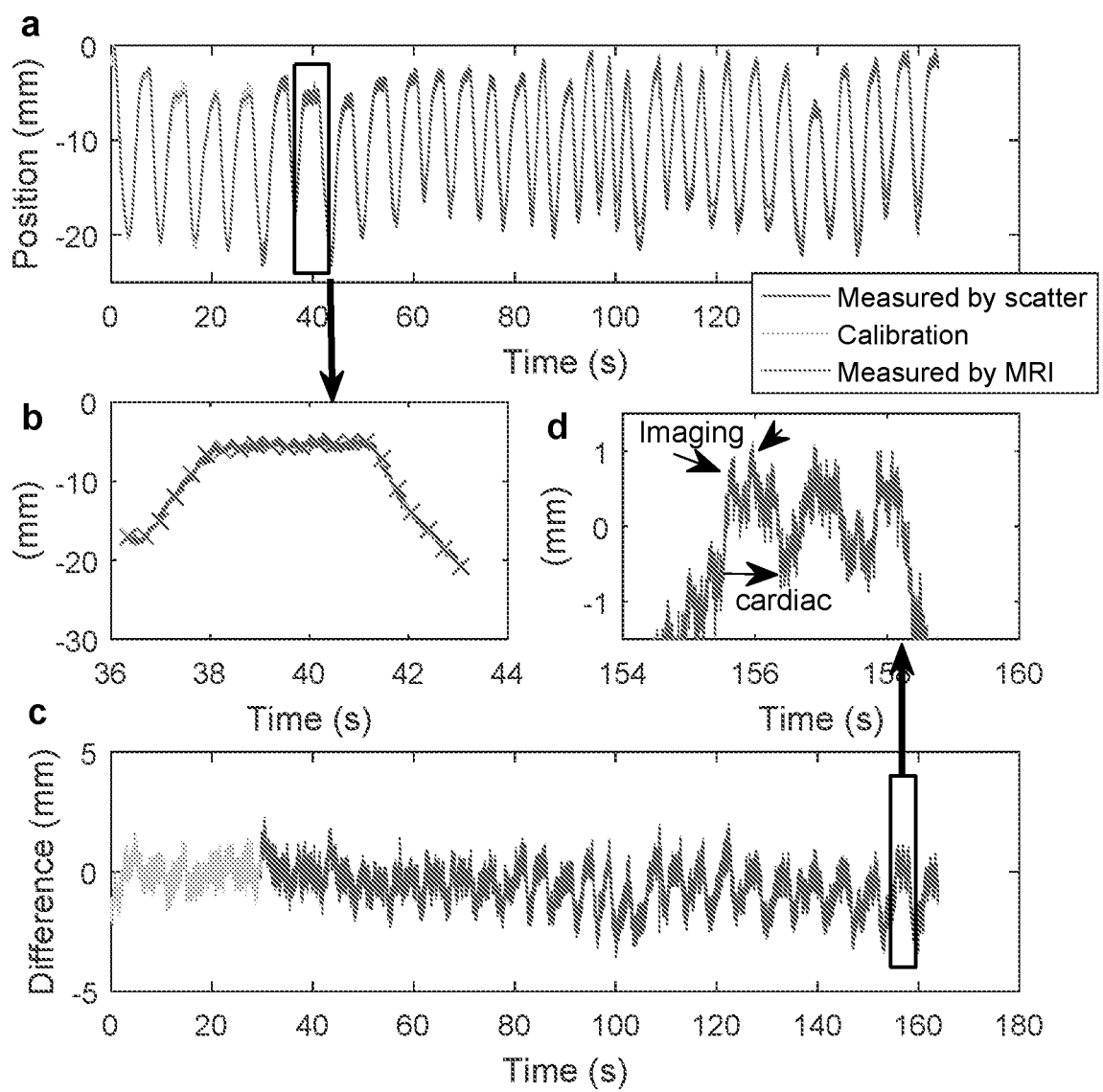
FIG. 14A is a plot of diaphragm position measured with scatter and MRI.
FIG. 14B is an extract from FIG. 14A showing the central position measured by scatter and position measured by MRI, FIG. 14C plots the difference between MRI and scatter measures at the RF pulse sampling frequency.
FIG. 14D is an excerpt from FIG. 14O in which oscillations are observed at the imaging frequency (3.1 Hz) and a lower frequency at the expected cardiac frequency (1 Hz).

The diaphragm position measured by scatter in one subject is shown in FIGS. 14A-14D compared to the diaphragm position measured with MRI. The figures plot the difference in diaphragm position measures between the two methods where the MRI is upsampled to the RF pulse rate. A systematic difference as a function of respiration is apparent. FIG. 14A shows a plot of diaphragm position measured with scatter and MRI. FIG. 14B is an extract from FIG. 14A showing the central position measured by scatter and position measured by MRI. FIG. 14C plots the difference between MRI and scatter measures at the RF pulse sampling frequency. FIG. 14D is an excerpt of this difference and shows two further periodic differences, the larger of the two at the cardiac frequency and a smaller periodic difference with at the imaging frequency.

In six subjects the standard deviation of the difference between the diaphragm position and that measured by scatter was 1.1±0.4 mm with a range of 0.6 mm to 1.5 mm, or a 95% confidence interval of ±2.2 mm. To compare the sample-to-sample noise to systematic error the standard deviation of the first discrete derivative with respect to time divided by square root of 2 was taken, this was 0.4±0.1 mm on average with a range of 0.3 to 0.6 mm.

In one subject the scatter position linearly drifted away from the MRI measure over its duration reaching 20 mm difference at the end. For this subject, two channels exhibited greater than 40% difference in the average returned voltage to that estimated by the S-matrix.

Figure 15:
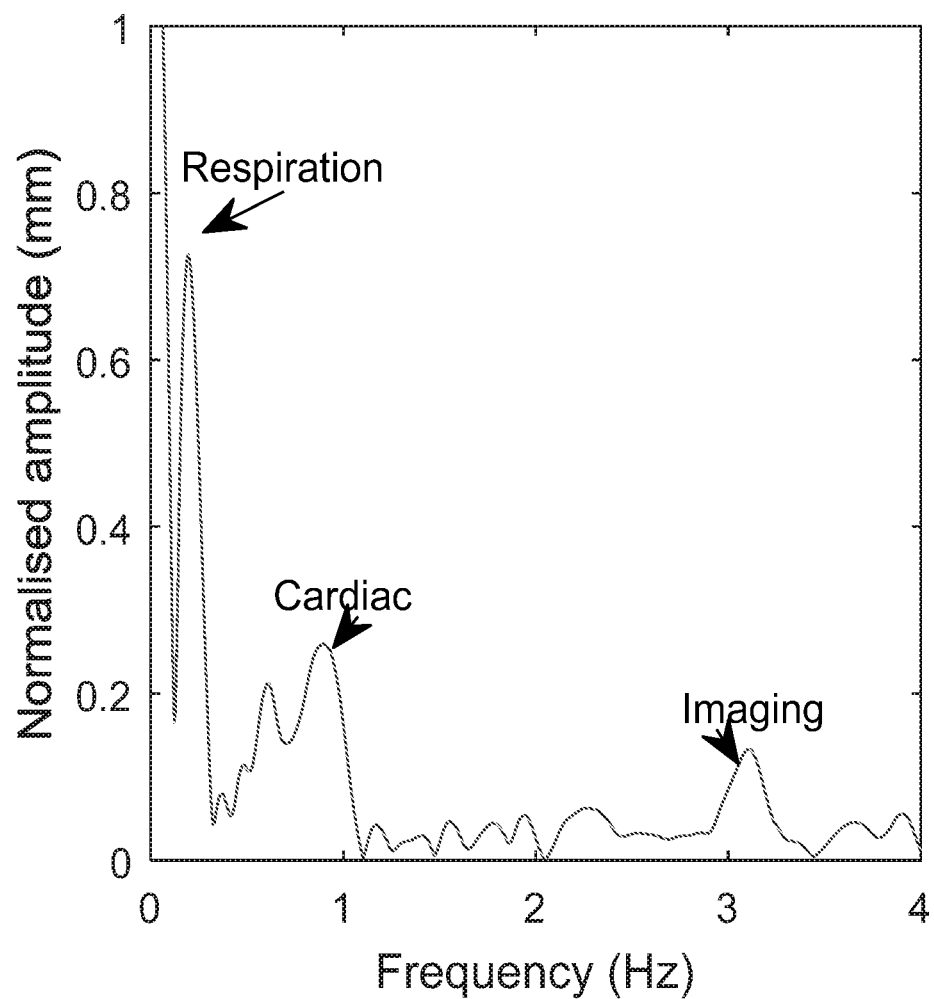
FIG. 15 is an example frequency spectrum of the difference between diaphragm position and scatter scaled to amplitude. Three frequency bands are shown: respiration, cardiac, and imaging. The spectrum is the Fourier transform of the difference between the scatter measure and diaphragm position followed by an apodization of 0.15 Hz with a Hanning window and the amplitude is normalized to the width of the Hanning window and frequency bin size. The average heart rate was 59.

The frequency analysis from one subject is shown in supporting FIG. 15. FIG. 15 shows an example frequency spectrum of the difference between diaphragm position[s] and scatter scaled to amplitude. Three frequency bands are shown: respiration, cardiac, and imaging. The spectrum is the Fourier transform of the difference between the scatter measure and diaphragm position followed by an apodization of 0.15 Hz with a Hanning window and the amplitude is normalized to the width of the Hanning window and frequency bin size. The average heart rate was 59.

Evident in this analysis are three dominant frequency bands, the largest, the respiratory band followed by a cardiac band with an average amplitude 0.4±0.1 mm followed by a band at the imaging frequency (3.1 Hz) with an average amplitude of 0.1±0.1 mm. These can be expressed as a 95% confidence interval of ±0.8 mm and ±0.2 mm for cardiac and imaging frequency respectively.

Figure 16A:
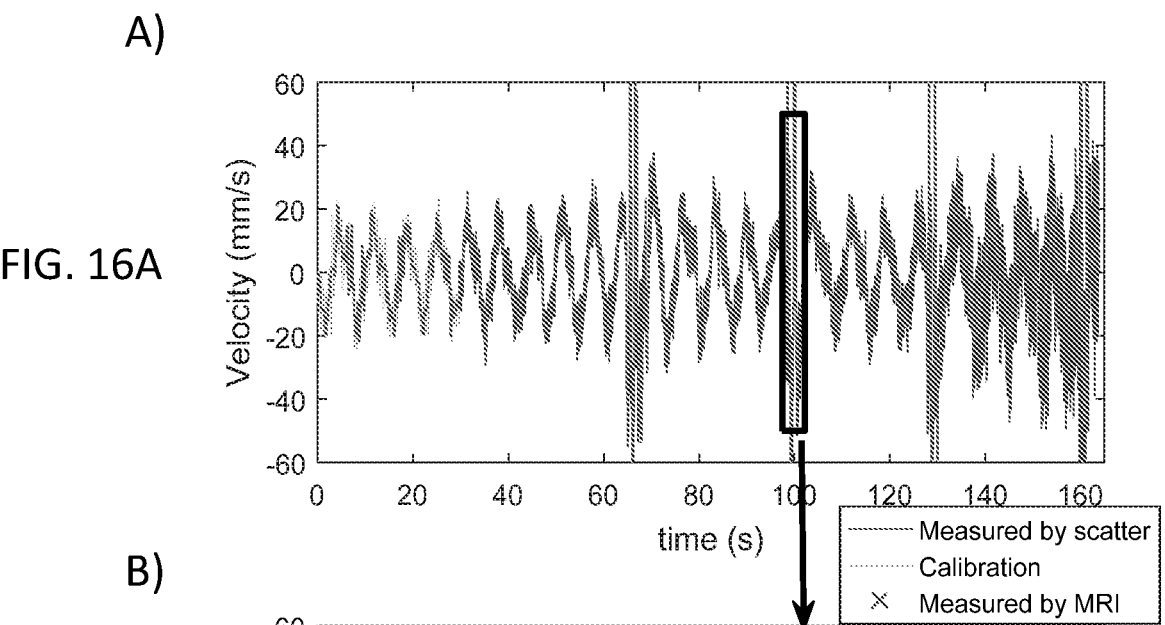
FIGS. 16A-16B plot velocity measured by scatter and MRI (FIG. 16A) with an excerpt (FIG. 16B) showing the fast response time to voluntary coughing (150 ms faster than the MRI measure).
Figure 16B:
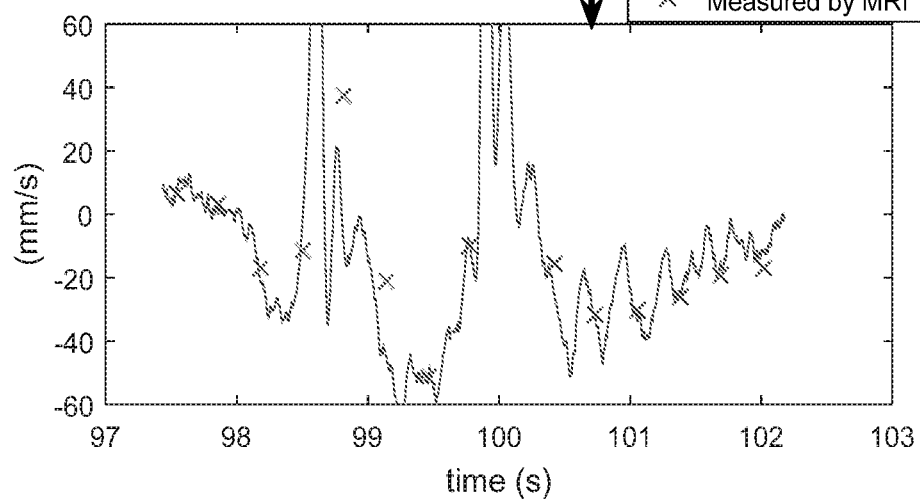

During the scan with deliberate coughing, the velocity estimated using both methods exceeded the standard range of +/−25 mm/s for all four coughs. In two of these the scattering measure detected the coughing 140 ms sooner than the imaging measure, and in the remaining two it was detected at the same time. This plot of Kalman filtered velocity is shown in FIGS. 16A-16B, which show velocity measured by scatter and MRI with an excerpt showing the fast response time to voluntary coughing (140 ms faster than the MRI measure).

Figures 17A, 17B:
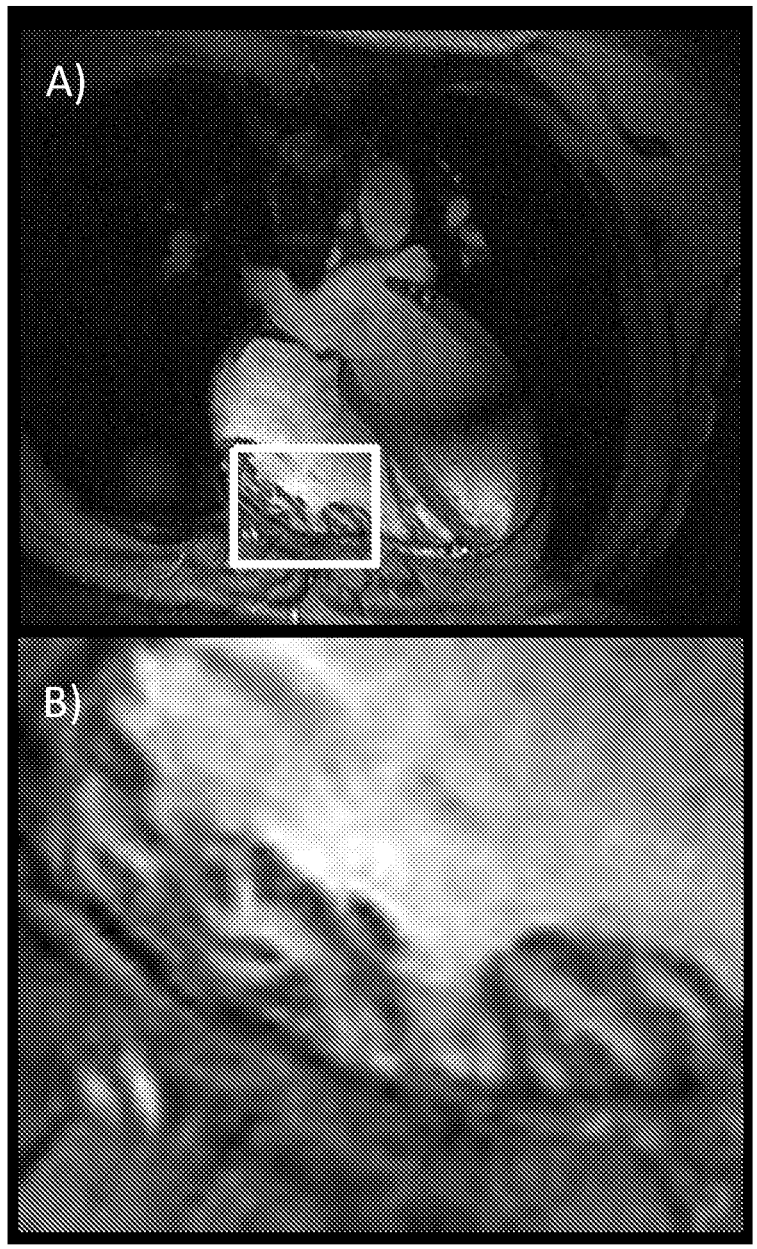
FIG. 17A is a single frame from free breathing gradient echo cine of the right side of the heart acquired and gated to end expiration using the new scatter prediction of diagphragm position.
FIG. 17B is an excerpt of FIG. 17A showing detail of the trabeculation in the right ventricle can be observed and no observable respiratory artefacts are present.

The image acquired using the real time cine scan is shown in FIGS. 17A-17B, which show a single frame from free breathing gradient echo cine of the right side of the heart acquired and gated to end expiration using the new scatter prediction of diaphragm position. Little to no respiratory artefacts are observed and the trabeculation of the right ventricle are well defined (FIG. 17B, which is an inset of FIG. 17A). Feedback delay delivery to the MPCUs ranged from 5 ms to 20 ms and pre-preparation of events was required for a total of 3 TRs (15 ms) to ensure no computational delays in waveform preparation this is a total feedback delay of 35 ms after the event.

Discussion

A new contact free measure of diaphragm position using the scattering measured by a local SAR monitor on a PTx system has been provided and evaluated. The 95% confidence interval of the measure was about ±2.2 mm, this is within a standard diaphragm navigator gating window size of 5 mm [52]. This error is dominated by differences that are slowly changing in time, this can be appreciated by the small temporal difference standard deviation of 0.4 mm. A frequency analysis found three dominant sources for the error, the greatest coincides with respiration. This can be expected as scatter is sensitive to both the liver position and lung filling volume, the latter of which may not be linear with diaphragm position. When used in practice as a source for binning or gating the effect of this will be to shift the bin or gate boundary by a small amount depending on the size of the bin.

The differences in position at the cardiac frequency are also a significant component of the overall error with a confidence interval of ±0.8 mm. These differences can originate from the motion of the heart and dynamic changes in blood volume throughout the cardiac cycle. For cardiac cine imaging this effect can inherently be resolved by gating the acquisition independently for each cardiac phase. The differences in position at the imaging range of frequencies was tenfold smaller than the overall error with a confidence interval of ±0.2 mm. As this is a non-physiological effect it can be classified as an error in the measurement. It is expected that this error is a result of a mechanical motion inside the RF coil induced by the gradients. This is likely to be specific to the TEM RF coil design as it contains two copper rods per transmit channel that are 50 mm long and 6 mm wide for adjusting tune and match on-the-fly using an autotune system [53].

In one subject, a significant drift was observed from the start to the end of the acquisition. This has implications for using this method. One reason for this can be an alteration in the gross subject to coil relationship which changes the S-Matrix between its measurement and the start of the acquisition, as evidenced by two channels average return being significantly different from that estimated by the measured S-Matrix in this subject. Such a change may be caused by a subject shifting between acquisition of the S-matrix and experiment or an electrical fault in the coil, given no image artefacts the former is more likely. An incorrect S-Matrix can have the effect that tiny drifts in one amplifier will appear in multiple return paths as the S-Matrix will fail to propagate the drift into the estimated return. A simple solution to this would be to incorporate the S-Matrix measurement into the start of each scan.

The high frequency of the diaphragm measurement lends itself to measuring respiratory velocity, which can enable the rapid detection of non-cyclic events such as coughing. Practically this can be used to inform the pulse sequence that such an event has occurred and prospectively hold the progression of encoding steps until the episode is over. Velocity could further be utilised to detect end-inspiration and separate out data acquired during inspiration from data during expiration.

This method was implemented on a 7T PTx MRI by programing the pulse sequence and image reconstruction computers to perform the real time measurement of diaphragm position. The high rate of measurement enabled the pulse sequence to open or close the respiratory gate independently for each cardiac phase. The advantage of using scatter over self-navigation methods [37] is that there is no requirement to use a radial encoding strategy or include navigator readouts [39], allowing both the choice of slice selection and encoding to be left to the target pulse sequence of choice.

In conclusion a new contact free quantitative measure of respiration is provided and shown that accurately resolves respiratory motion. The novel method utilizes scatter measured by existing PTx hardware and allows rapid, real time measurement of respiration.

REFERENCES

[34] Paling M R, Brookernan J R, Respiration artifacts in MR imaging: reduction by breath holding, J. Comput. Assist. Tornogr. [Internet] 10:1080-2.

[35] Wang Y, Grimm R C, Rossman P J, Debbins J P, Riederer S J, Ehman R L. 3D coronary MR angiography in multiple breath-holds using a respiratory feedback monitor. Magn. Reson. Med. [Internet] 1995; 34:11-16. doi: 10.1002/mrm.1910340104.

[36] Wang Y, Rossman P J, Grimm R C, Riederer S J, Ehman R L. Navigator-echo-based real-time respiratory gating and triggering for reduction of respiration effects in three-dimensional coronary MR angiography. Radiology 1996; 198:55-60. doi: 10.1148/radiology.198.1.8539406.

[37] Feng L, Axel L, Chandarana H, Block K T, Sodickson D K, Otazo R. XD-GRASP: Golden-angle radial MRI with reconstruction of extra motion-state dimensions using compressed sensing. Magn. Reson. Med. [Internet] 2015;O: n/a-n/a. doi: 10.1002/mrm.25665.

[38] Ehman R L, McNamara M T, Pallack M, Hricak H, Higgins C B. Magnetic resonance imaging with respiratory gating: techniques and advantages. AJR. Am. J. Roentgenol. [Internet] 1984; 143; 1175-82. doi: 10.2214/ajr.143,6.1175.

[39] Cheng J Y, Alley M T, Cunningham C H, Vasanawala S S, Pauly J M, Lustig M. Nonrigid motion correction in 3D using autofocusing with localized linear translations. Magn. Reson, Med. [Internet] 2012; 68:1785-97. doi: 10.1002/mrm.24189.

[40] Wang Y, Riederer S J, Ehman R L. Respiratory Motion of the Heart: Kinematics and the Implications for the Spatial Resolution in Coronary Imaging, Magn. Reson. Med. [Internet] 1995; 33:713-719. doi: 10.1002/mrm, 1910330517.

[41] Santelli C, Nezafat R, Goddu B, Manning W J, Smink J, Kozerke S, Peters D C. Respiratory bellows revisited for motion compensation: Preliminary experience for cardiovascular MR. Magn. Reson, Med. [Internet] 2011; 65:1097-1102. doi: 10.1002/mrm.22687.

[42] Buikman D, Helzel T, Röschmann P. The rf coil as a sensitive motion detector for magnetic resonance imaging. Magn. Reson. Imaging [Internet] 1988; 6:281-9.

[43] Zajíěk R, Oppl L, Vrba J, Broadband measurement of complex permitivity using reflection method and coaxial probes, Radioengineering 2008; 17:14-19.

[44] Nopp P, Rapp E, Pfutzner H, et al. Dielectric properties of lung tissue as a function of air content. Phys. Med. Biol. [Internet] 1993; 38:699-716. doi: 10.1088/0031-9155/38/6/005.

[45] Adriany G, Van de Moortele P-F, Wiesinger F, et al. Transmit and receive transmission line arrays for 7 Tesla parallel imaging. Magn. Reson, Med. [Internet] 2005; 53:434-45. doi: 10.1002/mrm.20321.

[46] Snyder C J, Delabarre L, Moeller S, Tian J, Akgun C, Van de Moortele P-F, Bolan P J, Ugurbil K, Vaughan J T, Metzger G J. Comparison between eight- and sixteen-channel TEM transceive arrays for body imaging at 7 T. Magn. Reson. Med. [Internet] 2012; 67:954-64. doi: 10.1002/mrm.23070.

[47] Snyder C J, DelaBarre L, van de Moortele P-F, Snyder A L, Akgun C, Tian J, Metzger G J, Ugurbil K, Vaughan J T. Stripline/TEM Transceiver Array for 7T Body Imaging. In: Proc. Intl. Soc. Mag. Reson. Med. Vol. 25; 2007. p. 164.

[48] Snyder C, Vaughan J T, Lemaire C A. Remotely adjustable reactive and resistive electrical elemens and method. 2012: US008299681B2, doi: US008299681B2.

[49] Schmitter 5, Wu X, Uurbil K, Van De Moortele P F. Design of parallel transmission radiofrequency pulses robust against respiration in cardiac MRI at 7 Tesla. Magn. Reson. Med. 2015; 74:1291-1305. doi: 10.1002/mrm.25512.

[50] Kalman R E. A New Approach to Linear Filtering and Prediction Problems. J, Basic Eng. [Internet] 1960; 82:35. doi: 10.1115/1.3662552.

[51] Hess AT, van der Kouwe A J, Tisdall M D, Neubauer S, Robson M D. 2D Diaphragm navigation with rapid gradient echo images: validation at 3T and application at 7T. In: ISMRM 23rd Annual Meeting & Exhibition. Vol. 0.; 2015. p. 2565. doi: 10.1002/mrm.25262.

[52] Fischer R W, Botnar R M, Nehrke K, Boesiger P, Manning W J, Peters D C. Analysis of residual coronary artery motion for breath hold and navigator approaches using real-time coronary MRI. Magn. Reson. Med. [Internet] 2006; 55:612-618, doi: 10.1002/mrm.20809.

[53] Keith G A, Rodgers C T, Hess A T, Snyder C J, Vaughan J T, Robson M D. Automated tuning of an eight-channel cardiac transceive array at 7 tesla using piezoelectric actuators. Magn. Reson. Med. [Internet] 2015; 73:2390-2397. doi: 10.1002/mrm.25356.

Example 4

Background

An alternative to ECG is provided requiring no additional hardware other than that provided with a commercial parallel transmit MRI scanner. Forward and return voltages are measured on an RF transmit line by the local SAR monitor. Returned voltages are a function of reflection from the subject and coupling through the subject from other transmitters and it is measured by the scattering (S) matrix. If the objects (and their complex permittivity) change within these RF fields, this is detected in the S-matrix. An method to characterise the cardiac cycle from the changing S-matrix is presented and is demonstrated in a cardiac cine acquisition.

Methods

Setup: 7T MRI (VB17, Step 2.3, Siemens), 8 channel PTX, local SAR monitor, 8 channel TEM cardiac transmit/receive coil. S-matrix measurements were made using a frequency multiplexed (2 kHz channel spacing) 5 ms Gauss RF pulse every TR=10 ms. The S-matrix and ECG were recorded in 10 subjects for 165 s including an initial 15 s breath hold.

Figure 18A:
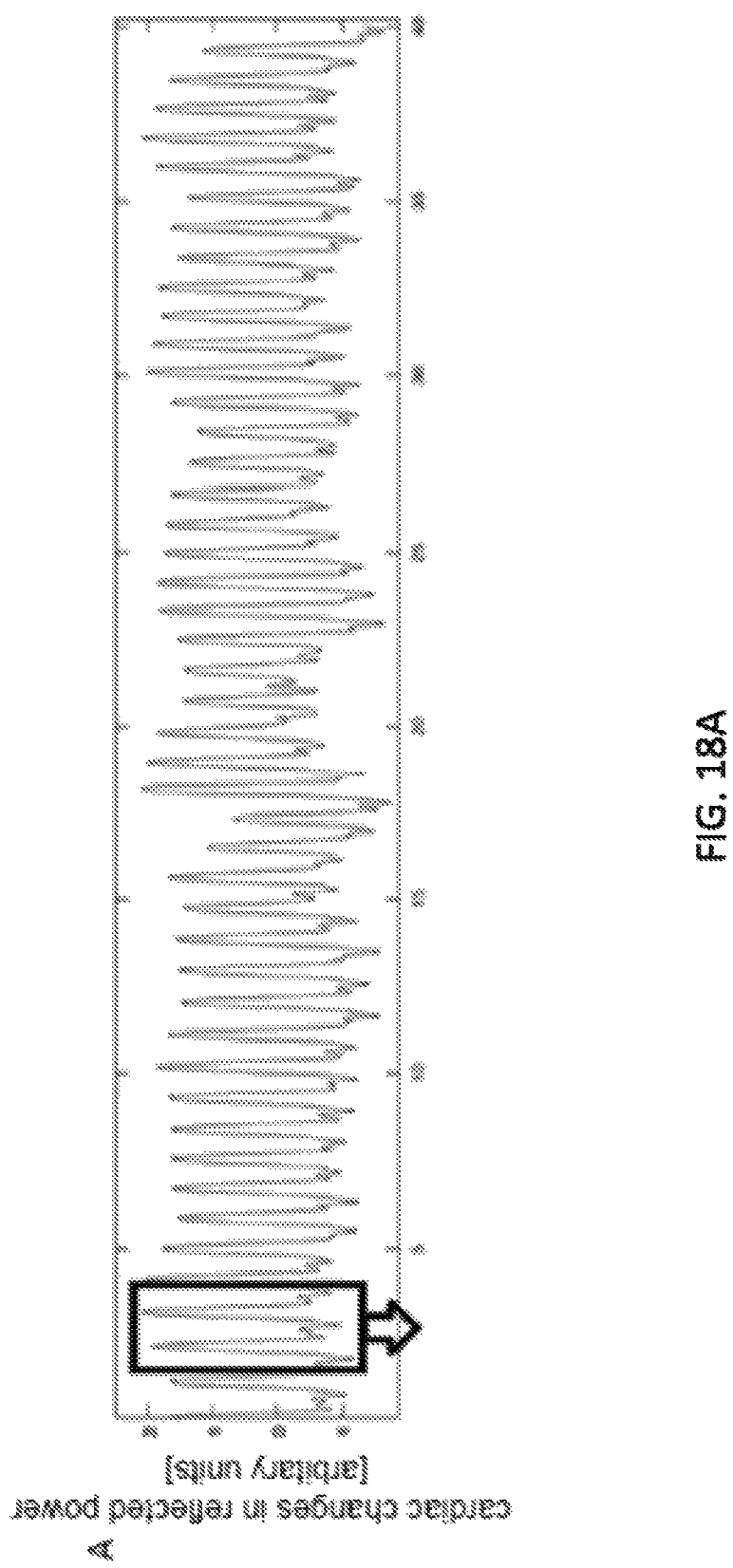
FIG. 18A is an example of the raw cardiac trace extracted by the independent component analysis (ICA). The main peak shown is the feature detection with an embodiment of the method as described herein. The full time course is shown.
Figure 18B:
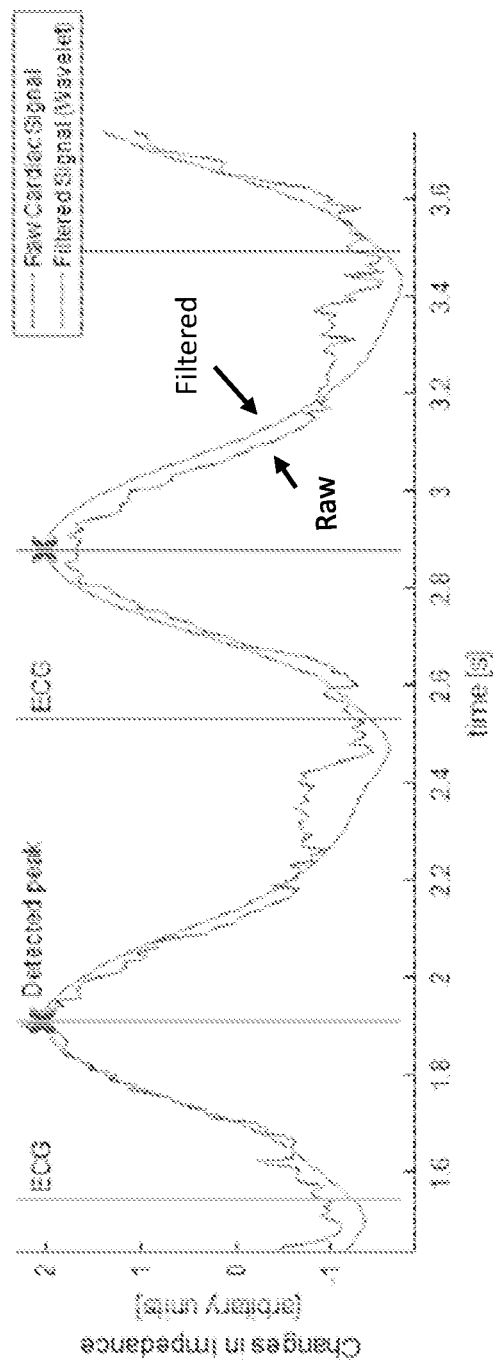
FIG. 18B shows two selected peaks from FIG. 18A.

A time series of the 8×8 S-matrix was split into real and imaginary components, providing 128 observations per time point. The data was temporally de-trended and the cardiac signal was extracted using an independent component analysis of cardiac band pass filtered data. The cardiac component was identified by a Welch power spectrum density estimate with highest power and the cardiac mixing vector determined. The mixing vector was used to establish a raw, unfiltered scalar signal. FIGS. 18A-18B show an example of this raw trace.

The cardiac signal was analysed using a multi-resolution discrete wavelet transform (DVVT) with a maximal overlap. A mother wavelet with (N=5) vanishing moments of symlets was used. The dominate heart frequency DWT was chosen and a peak detection carried out.

A 2D GRE cardiac cine was acquired and retrospectively gated with this method based on the eight return voltages measured during transmit, these are a row-sum of the S-Matrix.

Results

Using the ECG as a gold standard, the sensitivity and positive predictive value of the feature detection was 100%, the standard deviation of the difference in trigger time between ECG and the new method was 15 ms during breath holding and 22 ms while free breathing with a mean trigger delay of 302 ms and 260 ms respectively.

Figures 19A, 19B:
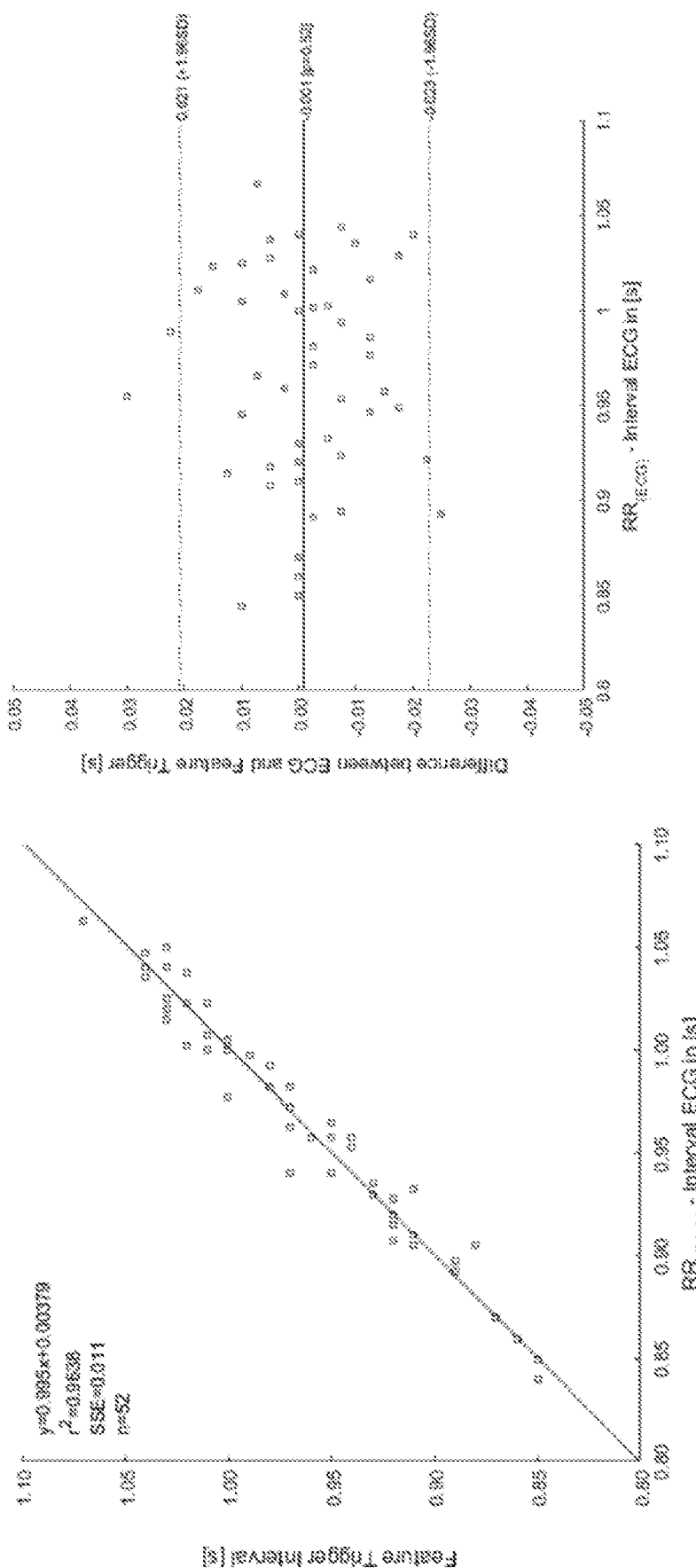
FIG. 19A is a correlation of the R-R duration derived from ECG and an embodiment of a method as described herein.
FIG. 19B is a Bland-Altman plot of the R-R duration derived from ECG and an embodiment of a method as described herein.
Figures 20A, 20B:
FIGS. 20A-20B are single frames from CINE GRE reconstruction using the cardiac trigger based on the reflection confidants measured during transmit RF pulses, with a 12° flip angle 8 k-space lines per phase of 23 ms acquired with a fixed 41 phases and total scan time of 13 seconds. Shown are one end systole (FIG. 20A) and one end diastole (FIG. 20B) time frames.

FIGS. 18A-18B show an example of the raw cardiac trace extracted by the ICA. The main peak shown is the feature detected with the proposed method. FIG. 18A is the full time course and FIG. 18B two selected peaks. FIGS. 19A and 19B show a correlation (FIG. 19A) and a Bland-Altman plot (FIG. 19B) of the R-R duration derived from ECG and the proposed method, respectively. FIGS. 20A-20B show Cine GRE reconstructed using the cardiac trigger based on the reflection confidents measured during transmit RF pulses, with a 12° flip angle 8 k-space lines per phase of the 23 ms acquired with a fixed 41 phases and total scan time of 13 s. Shown are one end systole (FIG. 20A) and one end diastole (FIG. 20B) time frames.

Conclusion

A new method for ECG-free cardiac synchronisation in MRI is provided that can be rolled out to PTX cardiac MRI scanners.

Example 5

Described in this example is a contact-free cardiac MRI triggering method based on reflected power measurements that requires no additional hardware other than that provided with a commercial parallel transmit (pTx) MRI scanner and wherein the influence of B1+ shim on the cardiac information extracted is evaluated. Time series of scattering matrices of the pTx monitoring system were used with random, uniformly distributed phases to simulate B1+ shims. Preliminary results in 7T MRI are shown with successfully, retrospectively gated 2D-CINE images using the present method.

Purpose

As noted above, ECG is the go-to method for cardiac MRI synchronization. ECG, however, requires preparation, electrodes and sometimes expert adjustment, An alternative is provided herein requiring no additional hardware other than that provided with a commercial parallel transmit (pTx) MRI scanner. Compared herein are monitoring the scattering matrix and monitoring only scatter from an excitation RF-pulse with a range of B1+ shimming modes.

Methods

A 7T MRI Scanner (VB17, Step 2.3, Siemens, Erlangen, Germany), equipped with 8-channel pTx. The local SAR monitor consists of 8 directional couplers (DICOs) connected on the transmission lines of a TEM cardiac transmit/receive coil [54] was used. The relationship between all channels of an N-port pTx coil is described by the scattering matrix(S). If the objects and their complex permittivity change within these RF-fields, this is reflected as a change in scattering [55]. S(t) was modeled as two components, one constant ($S_{exp}$) and one resulting from cardiac motion ($\Delta S_{cardiac}$). For the case where S is resolved, $\Delta S_{cardiac}$ can be measured. However, during an excitation RF-pulse the returned voltage $\vec{V}_{ref}(t)$, which is measured by the DICOs, is a function of $S(t)$ and the amplifiers forward voltage $\vec{V}_{fwd}(t)$ and the applied B1+shim($\vec{A}$) as follows:

$$\vec{V}_{ref}(t)=(S_{exp}+\Delta S_{cardiac}(t))[\vec{A}\odot\vec{V}_{fwd}(t)] \quad [1]$$

If $S_{exp}$ is measured before a scan, expected interplay between channels can be removed, and normalization can be done by an element wise vector division ($\oslash$) to form a vector ($\vec{\Gamma}(t)$) that is sensitive to cardiac motion as follows:

$$\vec{\Gamma}(t)=\vec{V}_{ref}(t)\oslash S_{exp}[\vec{A}\odot\vec{V}_{fwd}(t)]=\Delta S_{cardiac}(t)[\vec{A}\odot\vec{V}_{fwd}(t)]\oslash S_{exp}[\vec{A}\odot\vec{V}_{fwd}(t)]+\hat{u} \quad [2]$$

$\vec{\Gamma}(t)$ is utilized as a vector of 8 real and 8 imaginary components and $\hat{u}$ is a unit vector.

To extract a cardiac measure from either $\vec{\Gamma}(t)$ or $S(t)$, the following method was applied: measurements were temporally de-trended and the cardiac signal was extracted using an independent component analysis of cardiac band pass filtered signals. The cardiac component was identified by a Welch power spectrum density estimate with highest power in the cardiac frequency band (1=0.6-2.4 Hz) and the cardiac mixing vector was determined. The cardiac signal was analysed using a multiresolution discrete wavelet transform (DWT) with a maximal overlap. A mother wavelet with (N=5) vanishing moments of symlets was used and the mean heart rate was approximated using a fast-Fourier transform. The resulting dominate heart frequency DWT was chosen and a cardiac trigger event was determined using a peak detection of this signal (an example is shown in FIGS. 25A-25D for $\vec{\Gamma}(t)$ and $S(t)$, Data Acquisition An S(t) monitoring pulse sequence was created to transmit a frequency multiplexed (2 kHz channel spacing) 5 ms Gauss RF-pulse every TR=10 ms in 6 healthy adults (Male, age=24-39) during a 15 s breath-hold in compliance with ethical regulations. ECG was recorded during all measurements.

Simulation of B1-Shimming on RF-Excitation used for MRI

The time series of S-Matrices was averaged to determine $S_{exp}$. 10,000 vectors with random, uniformly distributed phases were generated to emulate potential B1+ shim sets ($\vec{A}_r$). The S-matrix time-series were used to determine $\vec{\Gamma}(t)$ for each $\vec{A}_t$ to simulate reflected power measurements based only on excitation RF-pulses used in B1+ shimming. The time of the cardiac trigger event (peak) was determined for each B1+ shim and each S-matrix combination. Further, one 2D-GRE cardiac cine (product sequence) was acquired to test retrospective gating with the proposed method using $\vec{\Gamma}(t)$ based on the eight return voltages measured during transmit.

Results

Figure 26:
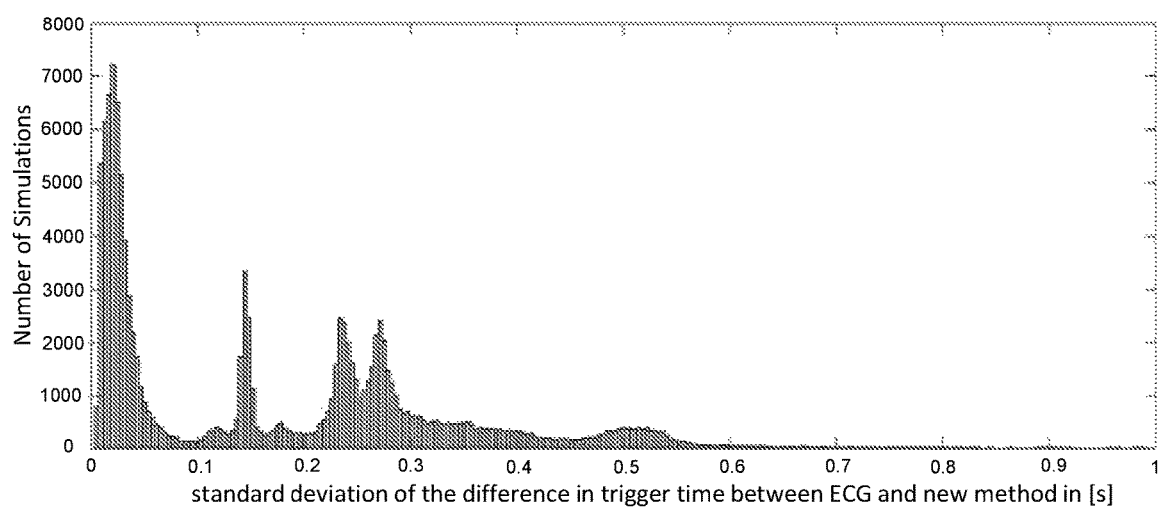
FIG. 26 is an example of a simulation of all applied, random B1+Shimming combinations and their impact on the cardiac signal extraction and gating using the proposed method. Exact trigger identification is assumed to have a standard deviation of the differences below 100 ms Values above 200 ms identify an incorrect cardiac motion estimation and values in-between extract systole detection.
Figure 27:
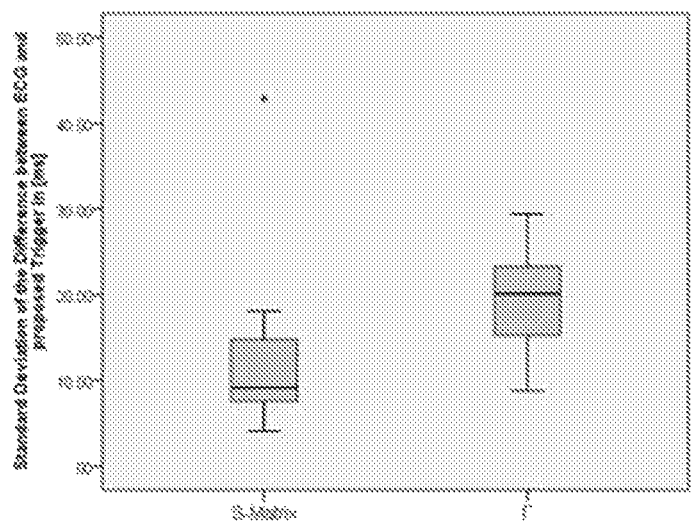
FIG. 27 shows a boxplot of the standard deviation of difference between ECG and main peak detection of the proposed method using the S-Matrix and simulated B1+ shimming with Γ, choosing the dominant mode of each dataset for comparison.
Figure 28:
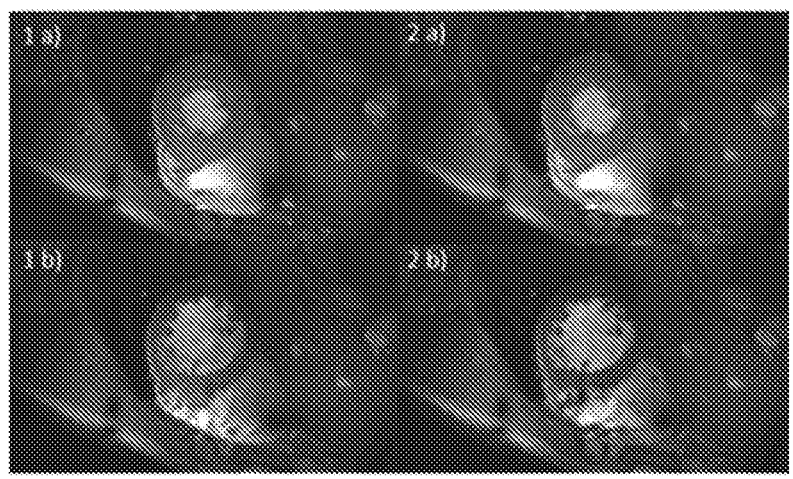
FIG. 28 represents a short-axis view of Cine GRE reconstructed using the ECG trigger (1) and cardiac trigger (2) based on the reflection coefficients measured during transmit RF-pulses, with a 25° flip angle 8 k-space lines per phase of 29 ms acquired with a fixed 33 phases and total scan time of 13s. Shown are one end-systole (A) and one end-diastole (B) time frames.

The standard deviation of the difference in trigger time between ECG and the present method (jitter) using the monitoring pulses and S(t) was 12.58±9.1 ms. For simulated B1+ shimming and the use of $\vec{\Gamma}(t)$, it varied considerably as a function of shim, see FIG. 26, with the dominant modes having a jitter of 19.43±6.75 ms and a number of RF shim settings providing no cardiac trace. FIG. 27 shows Boxplot of the standard deviation of difference between ECG and main peak detection of the proposed method using the 5-Matrix and simulated B1+ shimming with Γ, choosing the dominant mode of each dataset for comparison. Two time frames from the retro-gated cine, are shown in in FIG. 28 and compared with ECG gating.

Discussion

It is possible to extract cardiac gating information from the reflected voltage of an imaging RF-pulse in a pTx setup as described. However, it is dependent on the B1+ shim, with some B1+ shims yielding no viable cardiac trace. Therefore, during selection of $\vec{A_j}$; (B1+ shim), knowledge of $\Delta S_{cardiac}(t)$ can be taken into account.

The suitability of this method for cardiac gating at 7T has been shown with preliminary results on retrospectively gated 2D-CINE images without any pulse sequence modification. The images were acquired without any further external hardware nor sequence changes.

Conclusion

B1+ shim can influence the cardiac trace extracted by a new method for contact-free cardiac synchronisation in MRI but can still be used for successful gating on pTx cardiac MRI scanners without additional hardware.

REFERENCES

[54] Snyder, C. J. et al. Comparison between eight- and sixteen-channel TEM transceive arrays for body imaging at 7 T. Magn. Reson, Med, 67,954-964 (2012).

[55] Buikman, D., Helzel, T. & Roeschmann, P. The rf coil as a sensitive motion detector for magnetic resonance imaging. Magn. Reson. Imaging 6,281-289 (1988).

Example 6

Cardiovascular MRI at ultra-high field strength is a growing field of research and as such there is a need for reliable, accurate, and user-independent triggering and gating. A novel approach is provided herein that uses directional couplers (DICO's) from the SAR monitoring system and an 8-channel pTx coil to measure the reflection coefficients simultaneously to determine cardiac motion with an independent component analysis and Gaussian shaped RF-monitoring pulses. This method can improve cardiac imaging at ultra-high field CMR by providing robust triggering in periods of breath-hold and free-breathing, additional gating information and an optimised workflow with no additional set-up.

A purpose of this example is to explore new cardiac motion estimations, to interrogate the feature space and the ability to use RF-scatter to gate cardiac acquisitions.

Methods

Previous work on RF reflection was used to estimate motion using pick up coils or additional RF sources [56]-[59]. A method is provided herein that uses an 8-channel transmit RF coil with separate RF amplifiers and directional couplers (DICO's) on each of these transmit channels to determine whether the scattering matrix (S-matrix) measurements from the DICO's can be used to determine cardiac motion with an independent component analysis (ICA). The returned voltages are a function of reflection from the subject and coupling through the subject from other transmitters. The S-Matrix detects if the objects and their complex permittivity change within these RF fields.

$$S_{i,j} = \frac{V_{i,j,Return}}{V_{j,incident}} \quad [1]$$

A 7T MRI Scanner (VB17, Step 2.3, Siemens 7.0 T Magnetom scanner, Erlangen, Germany), 8-channel PTx system with local SAR monitor and an 8 channel TEM cardiac transmit/receive coil was used with four elements placed anterior on the chest of the subject and four elements placed posterior [60]. S-matrix measurements were made using a frequency multiplexed (2 kHz channel spacing) 5 ms, monitoring Gauss RF pulse every TR=10 ms in 6 healthy adults (Male, age=24-39 years) during a 15 s breath-hold followed by free-breathing for 25 s.

Data Pre-Processing

The time series of the 8×8 S-matrix was split into real and imaginary components, providing 128 observations per time point. The data was temporally de-trended and the cardiac signal was extracted using an ICA (FastICA [61] for Matlab, Version 2.5) of cardiac band-pass filtered data. The cardiac component was identified by a Welch power spectrum density estimate with highest power in the respective cardiac frequency band (f=0.6-2.4 Hz). The ICA de-mixing vector was used to establish a raw, unfiltered scalar signal.

Cardiac Signal Analysis and Feature Detection 5 features were identified and assessed in a retrospective signal analysis to detect different phases of the heart cycle. A main peak detection (feature 1), the start of the diastasis when the heart is almost at rest (feature 2), two for the start of atrial contraction (features 3 and 4) and one to detect the start of ventricular contraction (feature 5). Using the unfiltered and de-mixed cardiac signal three further traces were established to identify the features. The first is derived from a discrete wavelet transform (DWT) with a maximal overlap. A mother wavelet with N=5 vanishing moments of the family of symlets was used and the dominate heart frequency DWT and peak detection was carried out. The other two are the first and second derivatives derived from a low pass filtered signal to identify periods of rest and high velocity in the cardiac cycle.

Results

Figure 29B:
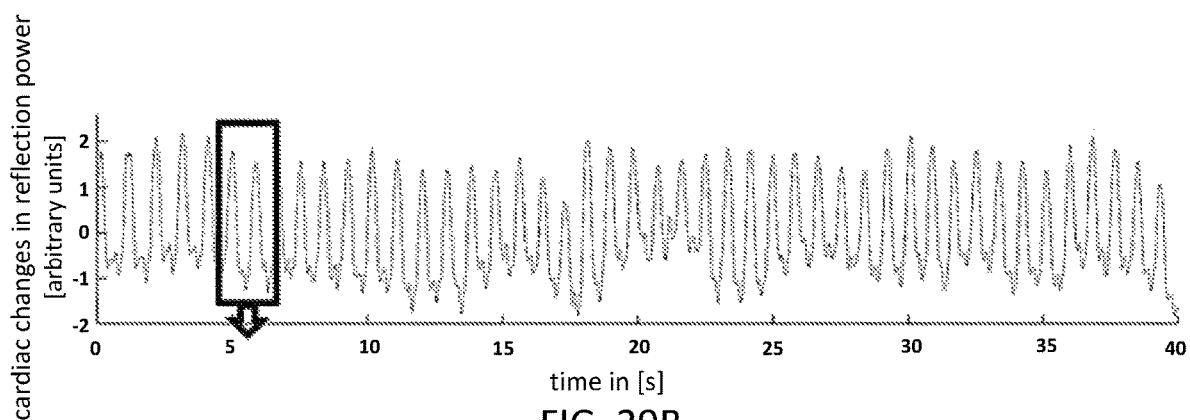
Figure 29C:
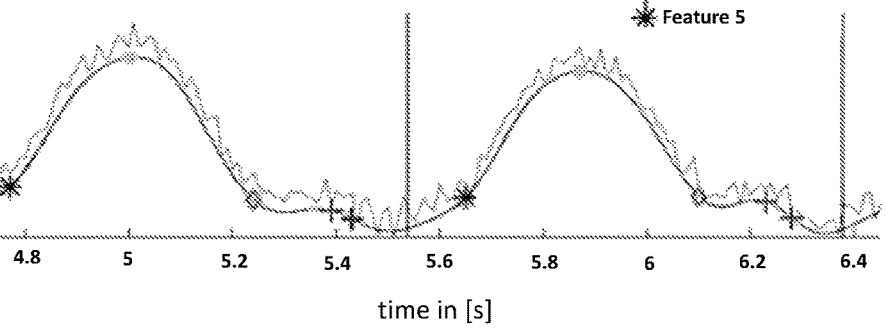
Figure 29D:
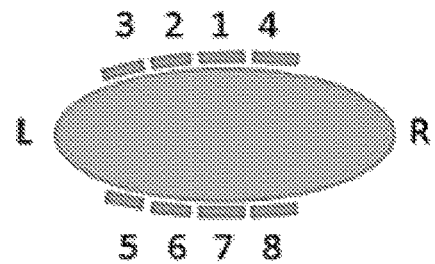

FIG. 29A shows an example of the raw power reflection on Coil 2 resulting from scattering and reflection from all coils (compare FIG. 29D) and the resulting cardiac trace extracted by the ICA. FIG. 28B is the full time course and FIG. 29C two selected peaks. Main peak shown is with feature 1 (green star). Diastasis detection by the violet diamond (feature 2), atrial contraction with red and blue crosses (feature 3 and 4 respectively) and feature 5 indicated by the black stars. Vertical red lines are ECG-trigger time points (R-peak).

Using the ECG as a gold standard, the sensitivity and positive predictive value of the feature 1 detection was 100%, the mean of the standard deviation of the difference in trigger time between ECG and the new method was 12.5 ms during breath-holding and 22 ms while free breathing with a mean trigger delay of 302 ms and 260 ms respectively.

Figure 30A:
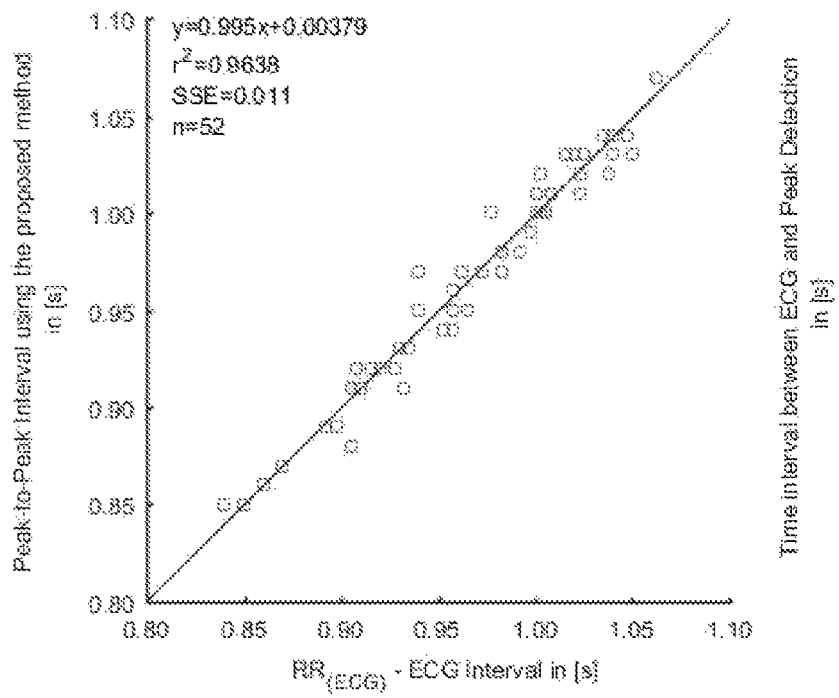
FIGS. 30A and 30B represent a correlation and Bland-Altman plot of the R-R duration derived from ECG and an example of proposed main peak detection of the cardiac signal in subject 1 during breath hold
Figure 30B:
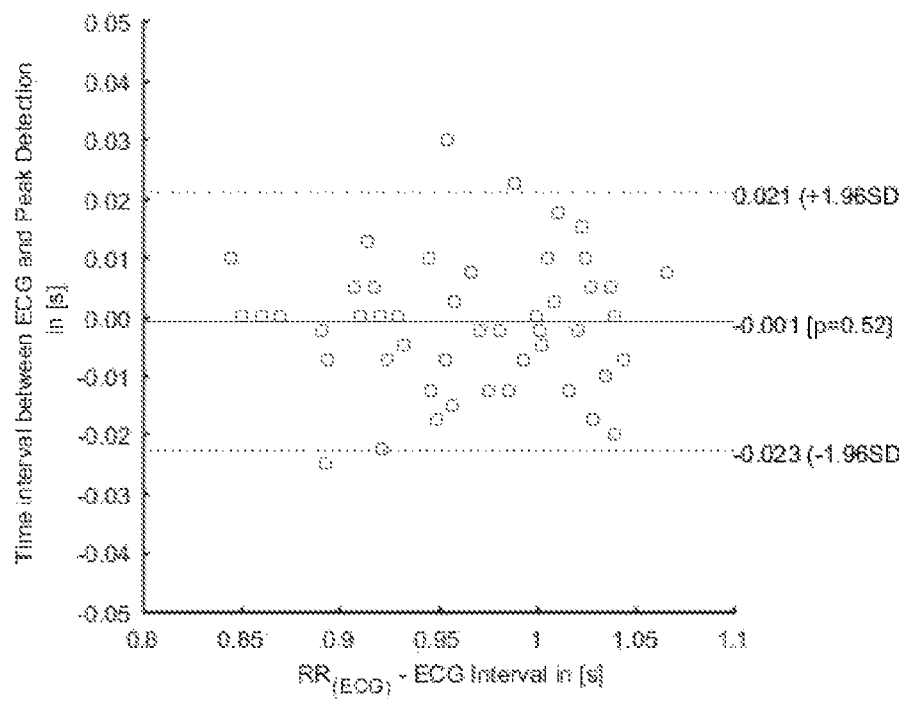
Figure 31:
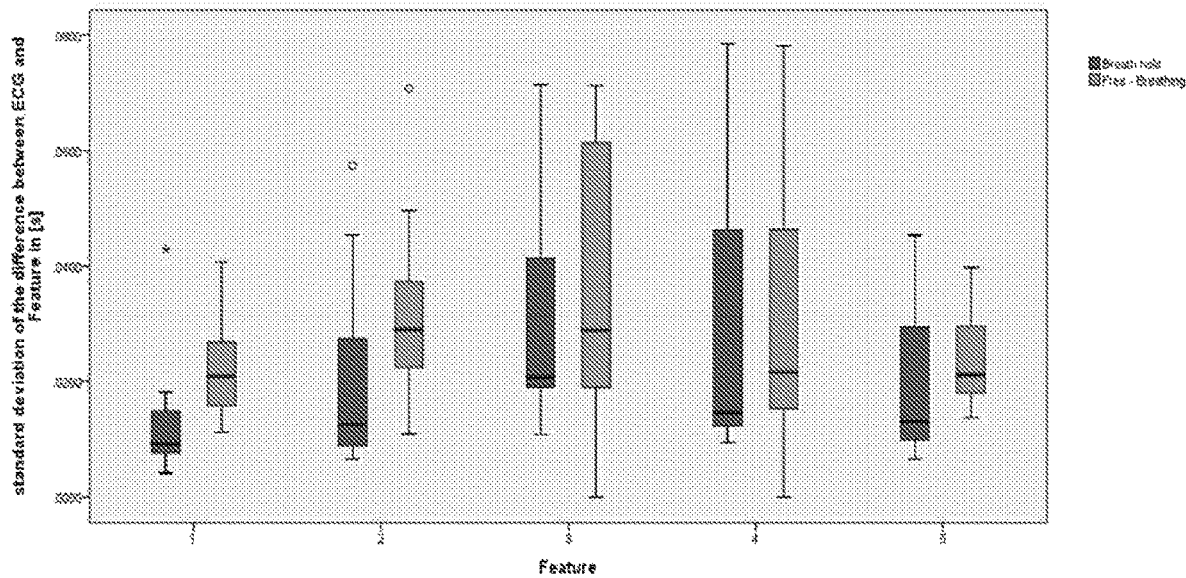
FIG. 31 is a boxplot of the standard deviation of the difference between the features and ECG trigger grouped by different features in breathhold. The lowest variation is achieved for the features 1 (main peak detection) whereas features 3 and 4 (Atrial Systole) show the highest variance.

The Bland-Altman analysis demonstrated that the RR-interval was within 21 ms of that calculated with ECG on a 96% confidence interval (see FIGS. 30A and 30B). The standard deviation of the difference in trigger time of the other features are shown in FIG. 31.

Discussion

The present method can achieve an automated, retrospective estimation of cardiac motion using a full scattering matrix derived from reflected power measurements with the commercial SAR-monitor of a 7T MRI. The cardiac motion can be estimated in-vivo during breath hold as well as in free breathing using an ICA. Features 3 and 4, which aim to detect the atrial contraction (corresponding P-wave in the ECG), do not provide a reliable detection when changes due to atrial contraction were around the noise floor of the data, resulting in a lower sensitivity and positive predictive value in some subjects. Feature 2, which aims to detect the start of the diastasis, shows a good overall performance and can provide additional information compared to ECG and its single peak detection. Only in higher mean heart rates is a lower sensitivity (mean Se=88%) observed which gives rise to a reduced duration of the resting state of the heart and therefore a smaller change in the refilling.

Conclusion

The present method for cardiac motion estimation in MRI can be rolled out to PTx cardiac MRI scanners assessing different stages of the heart movement.

REFERENCES

[56] Buikman, D., Helzel, T. & Roeschmann, P. The rf coil as a sensitive motion detector for magnetic resonance imaging. Magn. Reson. Imaging 6, 281-289 (1988).

[57] Graesslin, I. et al. Advancements in Contact-free Respiration Monitoring using RF Pick-up coils. Proc. 18th Sci. Meet. Int. Soc. Magn. Reson. Med. 3045 (2010).

[58] Graesslin, I. et al. An Alternative Concept for Non-Sequence Interfering, Contact-free Respiration Monitoring. Proc. 17th Sci. Meet. Int. Soc. Magn. Reson. Med. Honolulu, 752 (2009).

[59] Guido P. Kudielka, Christopher J. Hardy, Pierre-André Vuissoz, Jacques Felblinger, A. C. S. B. Utilization of the receive coil for cardiovascular and respiratory motion representation. in Proc. Intl, Soc. Mag. Reson, Med. 23 (2015) 0705. 2, 2015 (2015).

[60] Snyder, C. J. et al, Comparison between eight- and sixteen-channel TEM transceive arrays for body imaging at 7 T. Magn. Reson. Med. 67, 954-964 (2012)

[61] Gavert, H., Hurri, J., Sarela, J. & Hyvarinen, A. FastICA package for MATLAB, (2005)

Example 7

A method is provided to measure respiratory motion in mm units based on the scatter of a parallel transmit coil. The respiratory changes in scatter are observed by the local SAR monitor and converted into a respiratory measure through a calibration phase. The method was compared to the diaphragm position measured in MR images. The standard deviation of the difference between the two was 1.1±0.4 mm across six volunteers. The method was implemented into a free breathing cardiac cine which showed no respiratory artefact when used to gate.

Introduction

Respiratory motion remains a limiting factor to extending the acquisition time of cardiac MRI that is often needed to increase the spatial resolution. Several navigation methods have been proposed [62]-[66]. The present method is contact-free, has no sequence design constraints or additional hardware and provides the diaphragm position in mm units. It uses RF safety measurements on a parallel transmit system (pTx)[67]. pTx RF coils are an N-Port network where N is the number of transmit channels. The combination of coil design and complex permittivities of the subject's tissue determine the scatter (S) matrix, which can be measured by monitoring the RF with directional couplers (DICO's) on each of the coils. During respiration the lungs complex permittivity changes [68] due to changing air content and movement of the organs changes the load of the network.

Methods

Figure 32:
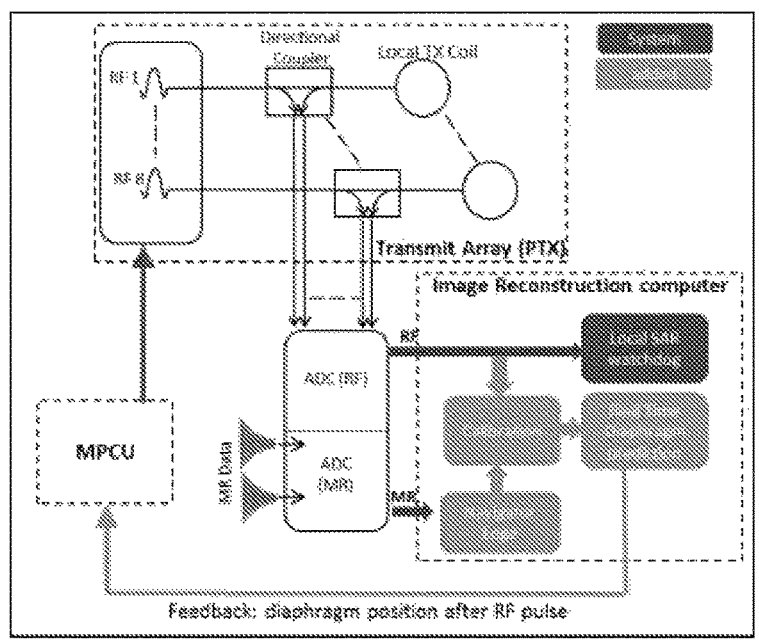
FIG. 32 is an example of a system schematic showing components of the pTx local SAR monitor in blue and the added software components to measure the diaphragm position in real time from the SAR monitor directional coupler measurements.

A Siemens 7T MRI scanner was used with pTx and local SAR monitor (VB17-step-2.3), and local transmit array [69]-[70]. The system measures the forward and returned RF voltage for each transmit line as depicted in FIG. 32. The vector $\vec{V}_{ret}(t)$ describes the complex returned RF voltages and can be modelled as a function of the expected scatter-matrix $S_{exp}$ (N×N, which is measured prior to scanning), the change in S due to respiration $\Delta S_{motion}(t)$, and the measured forward voltage $[\vec{A} \odot \vec{V}_{fwd}(t)]$ which is an element wise multiplication the B1+ shim $(\vec{A})$ and forward voltage of the amplifier $\vec{V}_{fwd}(t)$ as shown in equation 1.

$$\vec{V}_{ret}(t)=(S_{exp}+\Delta S_{motion}(t))[\vec{A} \odot \vec{V}_{fwd}(t)] \quad [1]$$

For a single B1+ shim $\Delta S_{motion}(t)$ cannot be solved for, however it can determine a vector $\vec{\Gamma}(t)$ that is a function of $\Delta S_{motion}(t)$, using an element wise complex division of the returned voltage resulting from $S_{exp}$ as follows:

$$\vec{\Gamma}(t)=\vec{V}_{ret}(t) \oslash (S_{exp}[\vec{A} \odot \vec{V}_{fwd}(t)]) \quad [2]$$

The complex vector $\vec{\Gamma}(t)$ is determined from data sampled over the central 50 µs of each RF pulse (k) and split into its real and imaginary components, giving a 16 element vector $\vec{\Gamma}'_k$. Finally, a mixing vector $\vec{m}$ and constant offset c are determined using a calibration cycle where the diaphragm position is measured for 30s with MRI and is recorded. $\vec{m}$ and c are determined by minimising the difference between $d_k$ and the diaphragm position (linear regression).

$$d_k = \vec{\Gamma}'_k \vec{m} + c \quad [3]$$

Seven healthy male volunteers were recruited according to institutional ethical practices. A sagittal spoiled gradient echo (SPGR) image was setup through the right hemi-diaphragm from which both a diaphragm image and $\vec{\Gamma}'_k$ can be determined. The SPGR had a flip angle ~5°, TR/TE: 5/2 ms, GRAPPA of 2 and 6:8 phase partial Fourier, matrix size of 304×156, FOV of 300×300 mm, duration 322 ms, repeated for 2:45 s (513 measurements). The first 30 s were used for calibration of $\vec{m}$ and the remaining 2:15 s for evaluation. For assessment the diaphragm position measured in the MR images is up sampled to the RF pulse rate.

To evaluate the method, a pulse sequence and image reconstruction program was setup to perform the calibration using a diaphragm navigator [71]. The sequence performed prospective respiratory gating and cardiac synchronisation in real-time for each RF pulse. A free-breathing cardiac cine SPGR was setup with a 1×1×3 mm resolution with a mm acceptance window.

Results

Figure 33A:
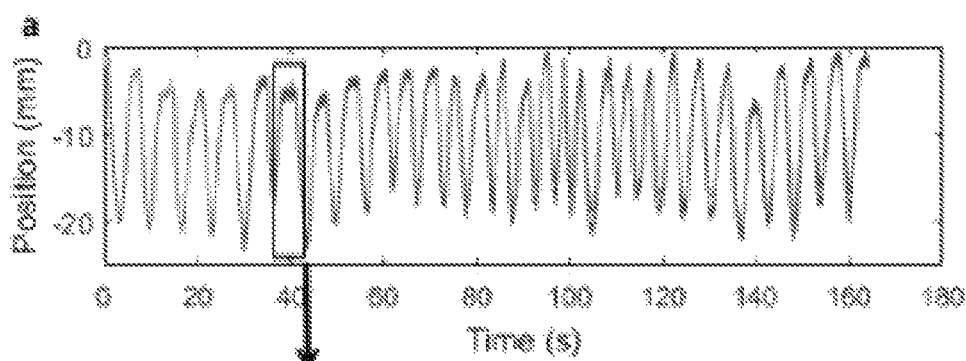
FIGS. 33A-33C.
Figure 33B:
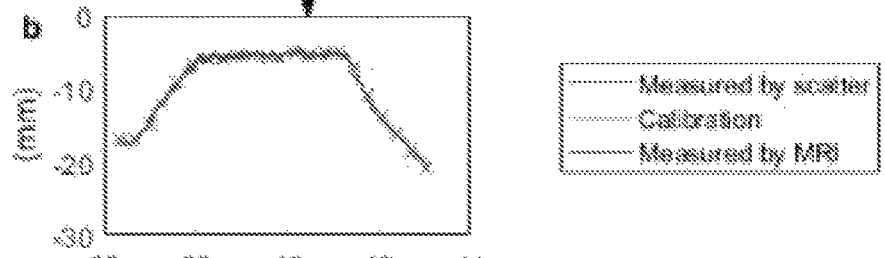
Figure 33C:
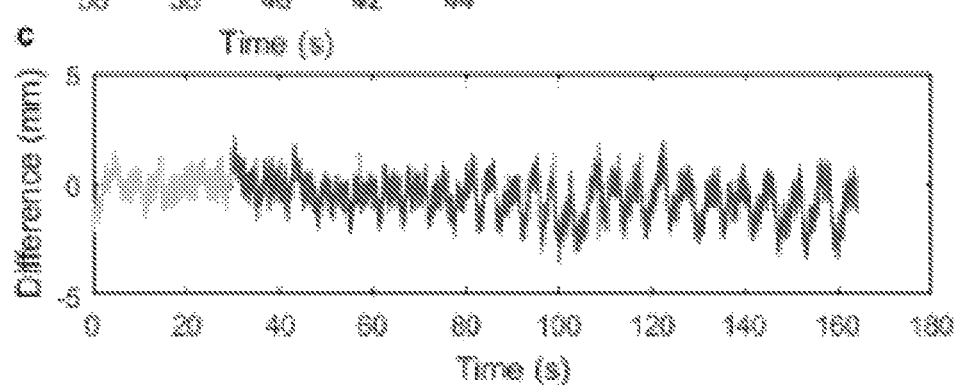

The measured diaphragm position from one subjects is shown in FIGS. 33A-33C. In six of the subjects the standard deviation of the difference to the diaphragm position in the image was 1.1±0.4 mm. The standard deviation of the discrete differentiation of this difference was calculated and divided by √2 giving 0.4±0.1 mm In one of the subjects a 20 mm drift was observed from the start of the scan to the end, along with a 40% deviation in reflected voltage compared to that expected by $S_{exp}$ indicating a change in the system.

Figures 34A, 34B:
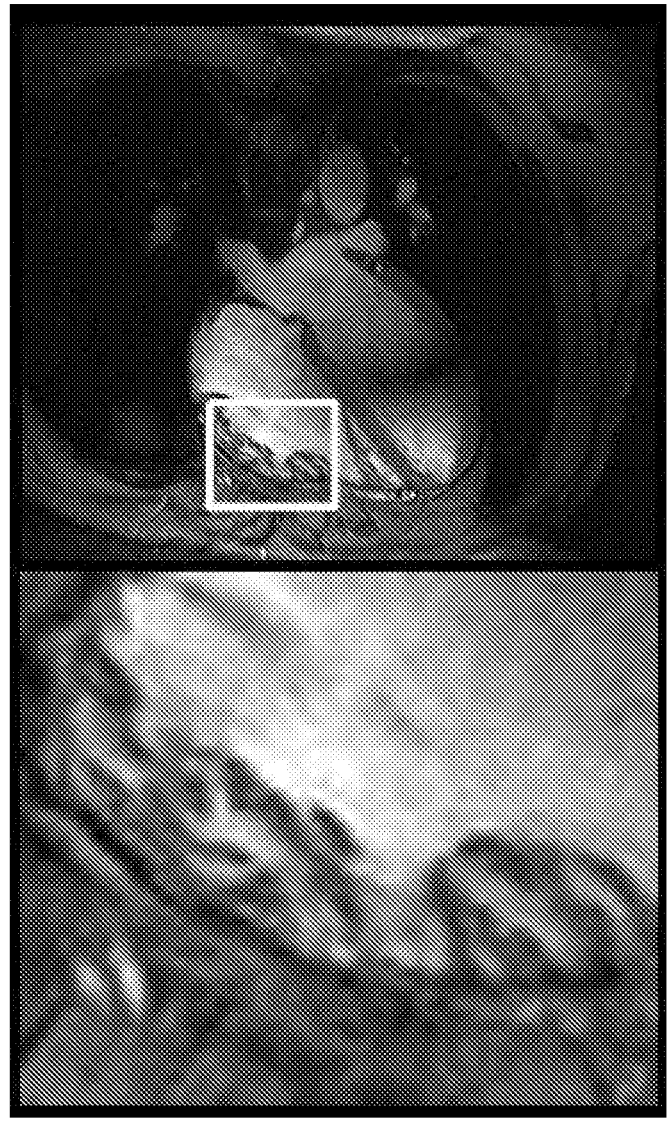
FIGS. 34A and 34B show a single time frame from the spoiled gradient echo cine acquired on the 7T MRI. The B1+ shim was optimised over the right side of the heart, with no respiratory artefacts observed and good clarity on small trabecular structures of the right ventricle. The flip angle was ~10°, TR/TE 5/2 ms, matrix 304×256, field of view 300×253 mm and 29 ms per cardiac phase and slice thickness of 3 mm and inplane resolution of 1×1 mm2.

FIGS. 34A and 34B shows a single time frame from the free breathing cardiac cine.

Discussion

The present method is shown to rapidly determine the diaphragm position for TR-to-TR respiratory gating. The use of the s-matrix for detecting changes in the position of the internal organs provides a new approach for quantitative real-time motion correction.

The approach enabled the acquisition of free breathing cine which was respiratory artefact free. The method can be calibrated for one or more, or even each B1+ shim, used as can be appreciated by $\vec{A}$ in the equations.

Conclusion

The method provides rapid diaphragm position that is contact- and hardware-free. Once calibrated the diaphragm position can be determined rapidly during a single excitation pulse.

REFERENCES

[62] Paling M R, Brookeman J R. Respiration artifacts in MR imaging: reduction by breath holding. J, Comput. Assist. Tomogr. 10:1080-2,

[63] Wang Y, Riederer S J, Ehman R L. Respiratory Motion of the Heart: Kinematics and the Implications for the Spatial Resolution in Coronary Imaging. Magn. Reson. Med. 1995; 33:713-719, doi: 10.1002/mrm.1910330517.

[64] Wang Y, Rossman P J, Grimm R C, Riederer S J, Ehman R L. Navigator-echo-based real-time respiratory gating and triggering for reduction of respiration effects in three-dimensional coronary MR angiography. Radiology 1996; 198:55-60, doi: 10.1148/radiology.198.1.8539406.

[65] Cheng J Y, Alley M T, Cunningham C H, Vasanawala S S, Pauly J M, Lustig M. Nonrigid motion correction in 3D using autofocusing with localized linear translations. Magn. Reson. Med. 2012; 68:1785-97. doi: 10.1002/mrm.24189.

[66] Feng L, Axel L, Chandarana H, Block K T, Sodickson D K, Otazo R. XD-GRASP: Golden-angle radial MRI with reconstruction of extra motion-state dimensions using compressed sensing. Magn. Reson, Med, 2015; 0:n/a-n/a. doi: 10.1002/mrm.25665.

[67] Hess A, Rodgers C, Robson M, Real-time diaphragm navigation using reflected power measurements from a multiple channel transmit RF coil on a human 7T. In: 24th meeting of the International socieity for magnetic resonance in medcine. Singapore: 2016, p. 3309.

[68] Nopp P, Rapp E, Pfutzner H, et al. Dielectric properties of lung tissue as a function of air content. Phys. Med. Biol. 1993; 38; 699-716. doi: 10.1088/0031-9155/38/6/005.

[69] Snyder C J, DelaBarre L, Metzger G J, van de Moortele P-F, Akgun C, Ugurbil K, Vaughan J T. Initial results of cardiac imaging at 7 Tesla. Magn. Reson. Med. 2009; 61:517-24. doi: 10.1002/mrm.21895.

[70] Hess A T, Bissell M M, Ntusi N A B, et al. Aortic 4D flow: Quantification of signal-to-noise ratio as a function of field strength and contrast enhancement for 1.5 T, 3T, and 7T. Magn. Reson. Med. 2015; 73. doi: 10.1002/mrm.25317.

[71] Hess A T, van der Kouwe A J, Tisdall M D, Neubauer S, Robson M D. 2D Diaphragm navigation with rapid gradient echo images: validation at 3T and application at 7T. In: ISMRM 23rd Annual Meeting & Exhibition. Vol. 0; 2015. p. 2565. doi: 10.1002/mrm.25262.

Example 8

Motion has the potential to severely corrupt MR images of the abdomen and thorax, primarily due to the superior-inferior motion of the diaphragm during the respiratory cycle. A number of solutions exist to address this, which can broadly be categorized into breath-hold methods [72],[73] and respiratory gating or binning methods [74]-[76]. Breath-holding remains the mainstay when acquisition durations can be restricted to fewer than 15 s. The alternative is to resolve the respiratory cycle, which comes with a trade-off between measuring the diaphragm position by introducing a sequence design constraint, such as a navigator echo [74], [77], encoding strategies with self-gating attributes [75], or the use of a bellows that provides a surrogate measure of diaphragm location [76] [78], [79].

Radiofrequency (RF) coils in MRI are sensitive to changes in the conductivity of tissues within their electric fields. In receiver arrays this effect has been monitored by measuring noise characteristics [80] and by introducing a reference transmitter (termed a "pilot-tone navigator") [81], Use of the transmit RF coil for monitoring dates back to 1988 when it was reported by Buikrnan et al. [82], who used a directional coupler (DICO) to monitor the returned power from the coil, More recently, pickup coils on a 3T parallel transmit (pTx) body coil were used to observe changes in the transmit coil current with respiration in multiple transmitters [83]; in later work, the authors identified that drifts in the transmit amplifiers confounded the continuous monitoring of respiration [84], and the use of low-power monitoring pulses was proposed. Like bellows, these methods provide a subject-dependent surrogate measure of respiration.

At 7T, abdominal and thoracic imaging uses local transmit pTx [85], [86] to improve homogeneity of the $B_1^+$ fields and reduce the total specific absorption rate burden. An intrinsic part of the safety monitoring in many MRI systems is the use of DICOs to measure the transmit current in each channel during RF pulses. Each channel of the transmit array is strongly coupled to the underlying tissue. Thus, these DICO measurements, which are already collected by the system during the RF pulses in any standard sequence, in conjunction with a calibration process, contain sufficient respiratory information to enable accurate tracking of the diaphragm.

A pTx RF coil can be characterized as an N-port electrical network, in which N is the number of transmit channels. This network has N inputs (the voltage and current into each channel) and N outputs (the voltage and current returned from each channel). During RF excitation, DICOs of a pTx system measure a time series of return and forward voltages ($\vec{V}_{ret}(t)$ and $\vec{V}_{fwd}(t)$, respectively), both complex vectors of length N. The voltages ($\vec{V}_{ret}(t)$ and $\vec{V}_{fwd}(t)$ are related to each other by the time-dependent scattering matrix, S(t), assuming no measurement error, by $$\vec{v}_{ret}(t) = S(t)\vec{v}_{fwd}(t) \qquad [1]$$

Each element of the N×N matrix S(t) is a ratio of input to output voltages of the network. The load of this network can be characterized by the impedance matrix Z(t). The impedance $Z_{i,j}(t)$ is the ratio of induced voltage on port i to a feed current on port j, as such S(t) and Z(t) are related using the characteristic impedance $Z_0$ (usually 50Ω) using the following equation, in which I is the identity matrix [87]:

$$S(t) = \left(\frac{1}{Z_0}Z(t) - I\right)\left(\frac{1}{Z_0}Z(t) + I\right)^{-1} \qquad [2]$$

Following the notation of Malmivuo and Plonsey [88], the induced voltage is proportional to the dot product of the lead fields ($\vec{J}_{li}(\vec{x}, t)$) of channels i and j, in which the lead field, $\vec{J}_{Li}(\vec{x}, t)$, is the current density at the spatial location $\vec{x}$ per unit input current on channel i [88] in units of m$^{-2}$. Equation [3] can be used to quantify the sensitivity of the network to the underlying tissue complex conductivity ($\sigma(\vec{x}, t)$ in units of Sm$^{-1}$) for each element to produce the symmetric matrix Z(t).

$$Z_{i,j}(t) = \int_V \frac{1}{\sigma(\vec{x}, t)} \vec{J}_{Li}(\vec{x}, t) \cdot \vec{J}_{Lj}(\vec{x}, t) dv \qquad [3]$$

Multiple tissue types, each with different $\sigma(\vec{x}, t)$, are present within each coil element's region of sensitivity, $J_{Li}(\vec{x}, t)$. As the subject breathes, the tissue changes, along with the complex conductivity of the lung tissue itself [89], [90]. These physiological perturbations in Z(t) give rise to similar changes in S(t).

However, during a pTx MRI scan that uses static $B_1^+$ shimming (i.e., all channels transmit the same pulse), a constant relationship is present among all ports, and Equation [1] cannot be inverted to determine S(t). Thus, $\vec{v}_{ret}(t)$ can be used as a measure of S(t), but $\vec{v}_{ret}(t)$ is also perturbed by any instability in any of the N RF amplifiers. Although these instabilities will be within the amplifier specification, they can be greater than the physiological effects. Previously, it has been suggested that $\vec{v}_{ret}(t)$ can be normalized on a channel-by-channel basis using $\vec{v}_{fwd}(t)$ [84], [91]. However, this does not take into account the presence of off-diagonal terms in S(t), Methods All experiments were carried out on a Magnetom 7 T scanner (Siemens, Erlangen, Germany) equipped with eight pTx channels and local specific absorption rate monitoring (software version VB17, step 2.3). The local specific absorption rate monitor consists of eight directional couplers (DICO's), one for each transmit channel, which monitor the complex forward $\vec{v}_{fwd}(t)$ and returned $\vec{v}_{ret}(t)$ RF voltage on each transmit channel. They can be demodulated by the carrier frequency and connected to the MR receivers' analog-to-digital converter that digitizes them at 1 MHz during all RF transmissions. The digitized voltages are delivered in real time to the specific absorption rate monitor. An eight-channel local transmit-receive RF coil was custom-built using the transmission line method, consisting of four elements positioned posteriorly and four anteriorly. Each element is 150 mm long and separated by 50-mm center to center and positioned for maximum coverage of the heart [86], [92]-[95].

Magnitude and Sensitivity of Respiratory Motion

In one healthy volunteer S(t) was measured by transmitting frequency-multiplexed, 5 ms, Gaussian RF pulses every 10 ms for 20 s during free breathing. The frequency spacing between each channel was 2 kHz. The scattering matrix, S, was calculated for each RF pulse using the DICO-measured voltages for each channel i, $\vec{V}_{fwd,i}$ and $\vec{V}_{ret,i}$. A Fourier transform was used to separate out the frequency components, j, corresponding to each channel, forming the matrix $V_{i,j}^{fwd}$ and $V_{i,j}^{ret}$. $V^{fwd}$ is a diagonal matrix, and $\vec{V}^{fwd}$=diag($V^{fwd}$) defined. Using Equation [1], S was calculated for each RF pulse, which were concatenated to form the time-varying matrix S(t), with 10-ms time resolution.

To evaluate the magnitude of amplifier noise and drift on DICO measurements made during a static $B_1^+$ shim, two synthetic return vectors were formed using this S(t). The amplifier effects were removed by taking the average over all time points of $\vec{V}^{fwd}(t)$ to form $\vec{V}^{ret,ideal}(t)=S(t)\vec{V}^{fwd}$. A second return vector was formed, preserving amplifier effects, as $\vec{V}^{ret,measured}(t)=S(t)\vec{V}^{fwd}(t)$.

Electromagnetic simulations of the transmission line coil on a model human thorax were carried out to understand the spatial sensitivity profiles of S. A simulation was run of the Transverse Electromagnetic Array (TEM) (1) centred over the heart and used in this paper. The simulation was conducted in Semcad X (Speag, ZMT, Zürich, Switzerland). The simulation used ideal decoupling (that is a single channel was simulated at one time while the others were removed from the simulation). The virtual family member Duke from IT'IS foundation was used in this simulation. The coil was tuned and matched to 50Ω impedance and the simulation had a resolution of 1 mm isotropic. To calculate the spatial sensitivity of the complex impedance matrix, each coil sensitivity ($\vec{J}_{Li}(v, t)$ in equation 3 of the paper) was calculated as the simulated current field divided by the drive current. The spatial distribution of the sensitivity of the impedance matrix is calculated as:

$$\frac{1}{\sigma(\vec{x}, t)} \vec{J}_{Li}(\vec{x}, t) \cdot \vec{J}_{Lj}(\vec{x}, t) \qquad [3.2]$$

Method

S(t) can be modeled as the sum of a temporally invariant matrix $S_0$ and a motion-dependent matrix $\Delta S_{motion}(t)$ as follows:

$$S(t)=S_0+\Delta S_{motion}(t) \qquad [4]$$

$S_0$ is measured before the target image acquisition using the frequency multiplexed RF pulse, as done previously, at an arbitrary respiratory state. During the $B_1^+$ shimmed target image acquisition, all channels transmit with identical frequency. To track respiratory motion, a vector $\vec{\Gamma}(t)$ is calculated from an element-wise division of N×1 vector $\vec{v}_{ret}(t)$ by the return expected given $S_0$ (expected return=$S_0 \vec{v}_{fwd}(t)$) as follows:

$$\vec{\Gamma}(t) = \frac{\vec{v}_{ret}(t)}{[S_0 \vec{v}_{fwd}(t)]} = 1 + \frac{[\Delta S_{motion}(t) \vec{v}_{fwd}(t)]}{[S_0 \vec{v}_{fwd}(t)]} \qquad [5]$$

The complex vector $\vec{\Gamma}(t)$ is determined from the central 50 μs of DICO data sampled for each RF pulse. A diaphragm position estimate ($d^{est}(t)$) is formed by summing the real and imaginary components of $\vec{\Gamma}(t)$ with weighting vectors and as follows:

$$d^{est}(t)=\text{real}(\vec{\Gamma}(t)) \cdot \vec{m}_r + \text{imag}(\vec{\Gamma}(t)) \cdot \vec{m}_i + c \qquad [6]$$

where c is a constant offset.

$\vec{m}_r$, $\vec{m}_i$, and c are determined in a calibration in which the diaphragm position is measured with MRI and $\vec{\Gamma}(t)$ is recorded for each diaphragm image and determined using a least-squares optimization.

Validation

Seven healthy male volunteers were recruited according to the institution's ethical practices. A $B_{1+}$ shim was applied that adjusts only the phase of each channel to maximize the minimum $B_1^+$ over the edge of the diaphragm for both inspiration and expiration [96]. A sagittal spoiled gradient echo (SPGR) image was prescribed through the right hemidiaphragm, from which both a diaphragm position and $\vec{\Gamma}(t)$ can be determined. The SPGR had a flip angle between 2° and 10°, a train of 71 sinc RF pulses of 1.0 ms long, repetition time (TR)/echo time of 5.0/2.0 ms, generalized autocalibrating partial parallel acquisition iPAT factor of 2 and 6:8 phase partial Fourier, matrix size of 304×156, and field of view of 300×300 mm² for a total acquisition duration of 322 ms. This was repeated for 2 min 45 s, giving a total of 512 images and 512×71 sets of forward and returned voltage vectors.

The diaphragm images along with digitized forward and returned RF voltages were processed in MATLAB (MathWorks, Natick, Mass., USA) and $\vec{\Gamma}'(t)$ determined retrospectively. The diaphragm position in the images was determined using edge detection and upsampled to the RF pulse rate using linear interpolation. The first 93 images (30 s) were used for calibration; the remaining 420 images were used to evaluate the estimate $d^{est}(t)$. No temporal filtering was applied to the diaphragm estimate.

A frequency analysis on the difference between $d^{est}(t)$ and diaphragm position in the target images for each subject was done with a Fourier transform of the difference, and an energy-conserving Hanning apodization of 0.15 Hz.

One subject was instructed to cough four times during the acquisition after the initial 30-s calibration, to evaluate the response of the system to nonperiodic respiration. For this assessment, a Kalman filter [97] was used to estimate diaphragm velocity from both the scattering and image-based diaphragm positions. The Kalman filter gain (Δ*) was 2.9 s⁻¹ for velocity and 0.16 for position [97]. Velocities out of the standard range (−25 to 25 mm/s) are taken to be the start of coughing.

Real-Time Pulse Sequence

To evaluate the practicality of this method for prospective, real-time, respiratory-state detection, a pulse sequence was developed. This contained two parts, the first being calibration using an SPGR diaphragm navigator [98] sequence with three imaging RF pulses between each navigator and lasting 30 s, and the second part being the target imaging acquisition. The navigator had a matrix size of 210×21, field of view of 300×300 mm, slice thickness of 13 mm, TR/echo time 3,5/1.5 ms. The three target image RF pulses were used to determine ~G during calibration. The target image acquisition part of the sequence received feedback on the diaphragm position each TR. The sequence opened or closed a respiratory gate for each TR, as determined by the diaphragm position estimated. The time for this feedback loop was 35 ms from measurement to an adapted execution. This included a 2-ms calculation time, 15-ms pulse pre-preparation time, and an 18-ms buffer for fluctuations in network communication and computation time.

The present method was implemented on the scanners image reconstruction system. It consisted of an image reconstruction and edge detection for the navigator images, a functional unit to perform the calibration, and online calculation of the diaphragm position from scattering, which is transmitted back to the MPCUs of the pTx.

For this work the target imaging sequence was a 2D cine SPGR pulse sequence. A horizontal long-axis cine of the right side of the heart was acquired in a single healthy volunteer as follows: separate $B_1^+$ shims were set for the right hemidiaphragm and right side of the heart for the navigator and image, respectively, with a ±3-mm acceptance window at end expiration. The cine had a flip angle of approximately 10°, TR/echo time 5.0/2.0 ms, matrix 304×256, field of view 300×253 mm, 29 ms per cardiac phase, and slice thickness of 3 mm.

Results

Magnitude and Sensitivity of Respiratory Motion in Scattering

Figures 35A, 35B, 35C:
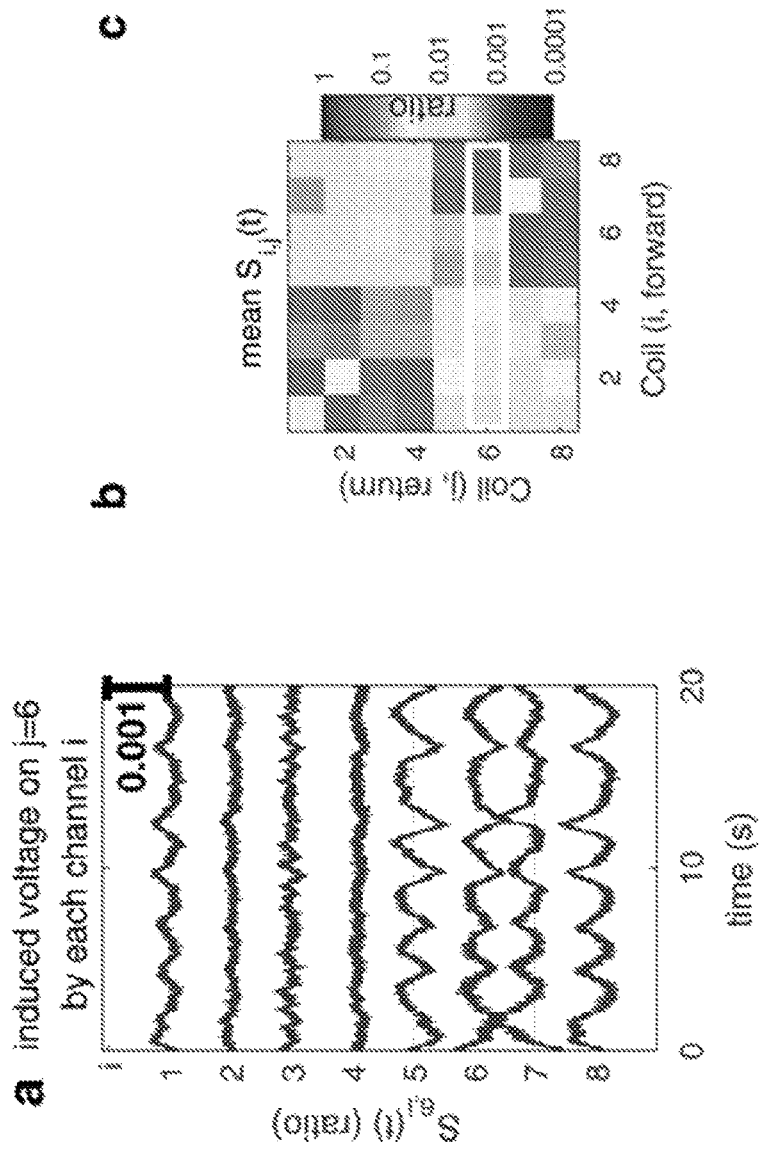
FIGS. 35A-35C illustrate components of the scattering matrix.
Figure 36A:
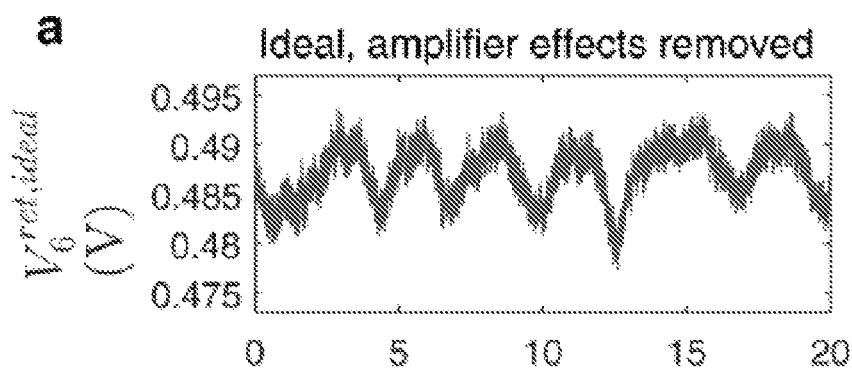
Figure 36B:
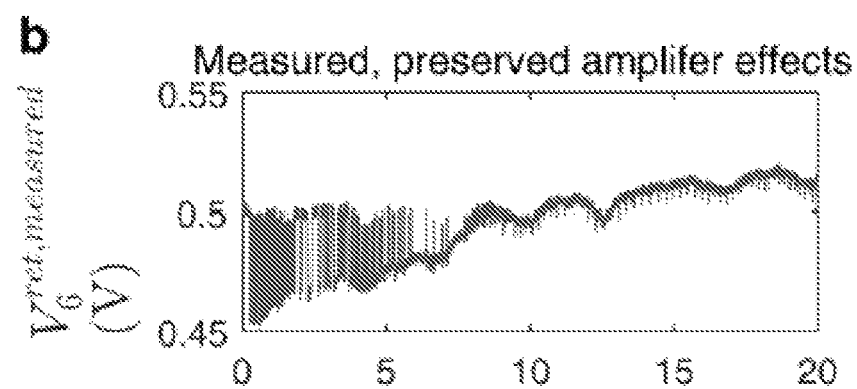
Figure 36C:
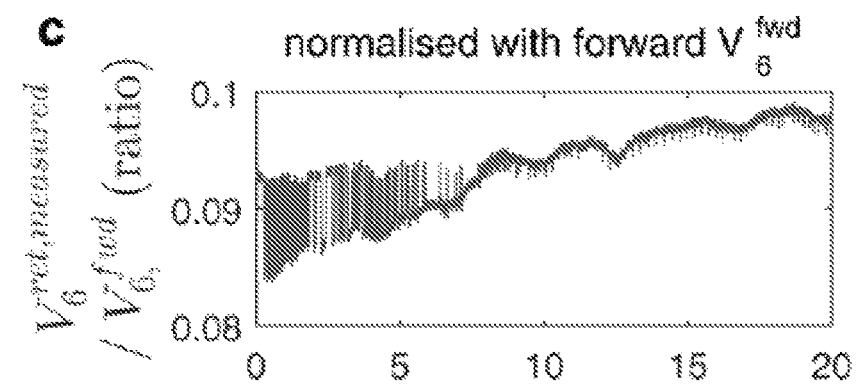

FIGS. 35A-35C show the sixth row of the scattering matrix, measured continuously for 20 s, its mean, and its standard deviation. These data show that the physiological motion exceeds the DIGO measurement error, that $\Delta S_{motion}(t)$ has similar magnitude both on and off the diagonal. FIGS. 36A-36D plot the components of the synthetic return vectors for channel 6. These figures demonstrates that the amplifier influences on $V_6^{ret,measured}(t)$ exceed the physiological fluctuations, which also holds in the other channels. FIGS. 36A-36D also show that normalization of $V_6^{ret,measured}(t)$ using the forward voltage of channel 6 is insufficient to recover the respiratory information, which is recovered with $\Gamma_6(t)$.

Figure 40A:
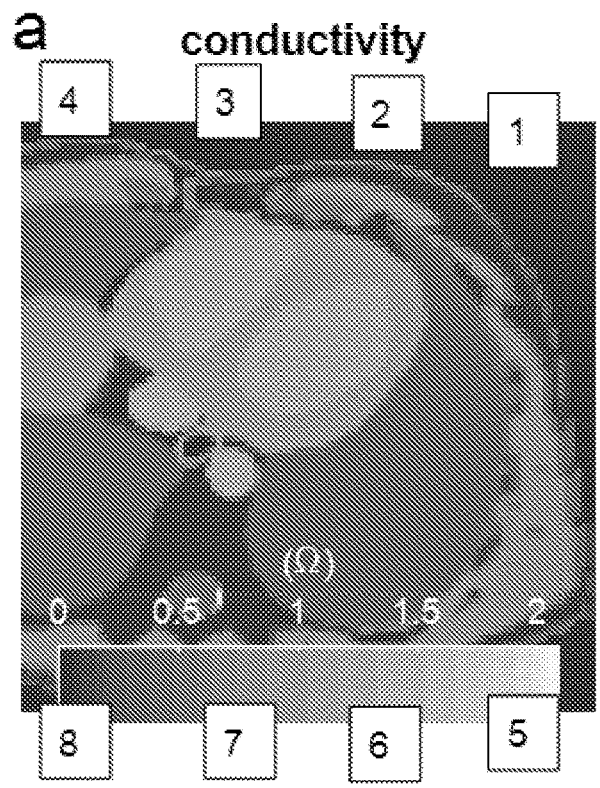
FIGS. 40A-40C.
Figure 40B:
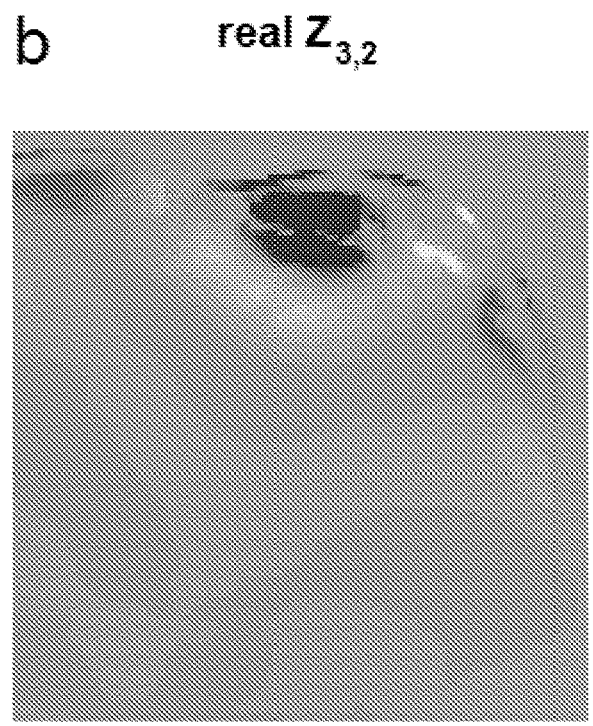
Figure 40C:
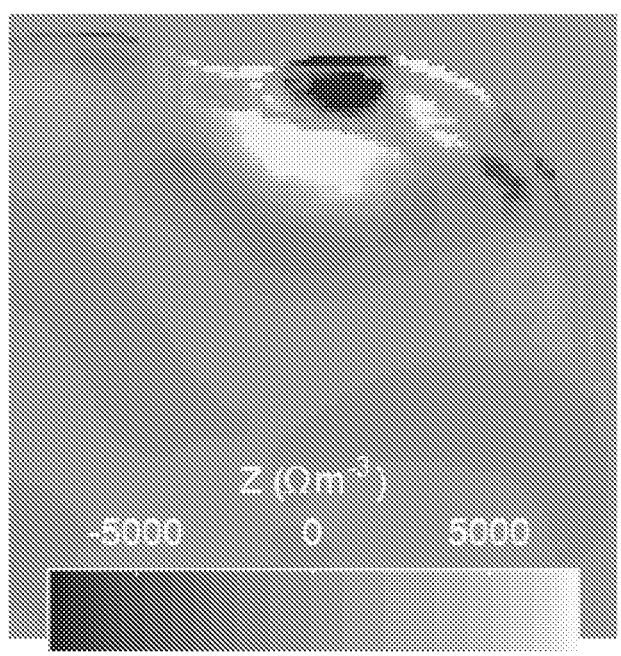
Figure 41:
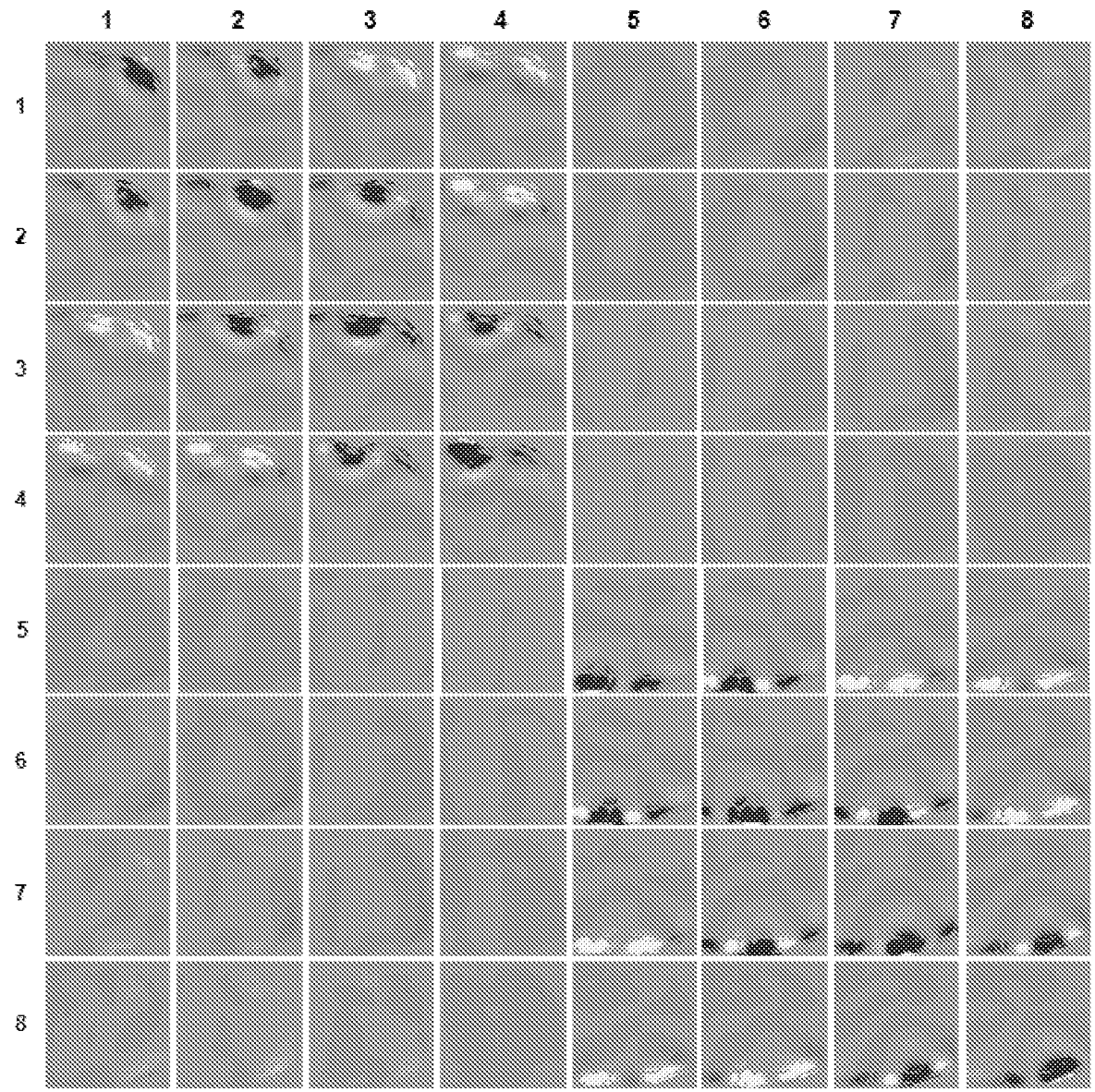
FIG. 41 illustrates the real part of the spatial distribution of sensitivity of the impedance between channels i and j. This matrix is symmetric and otherwise distinctly different sensitivity patterns are shown. See colorbar in FIGS. 30A-30C.

Plotted in FIGS. 40A-40C and FIG. 41 is a transverse slice through the thorax of the spatial distribution of the sensitivity of the impedance matrix Z in $\Omega m^{-3}$. FIGS. 40A-40C compares real and imaginary components and shows that the real and imaginary components have different sensitivity distributions as is evident in the sign of real and imaginary terms. FIG. 41 shows how the real part of all the sensitives vary spatially. Notably there are both positive and negative contributions.

Validation

In six subjects, the root mean square error in $d^{est}(t)$ (difference compared with MRI) was 1.460.5 mm, but in one subject there was a gradual increase in $d^{est}(t)$ to 20 mm in diaphragm position by the end of the scan. On inspection in this subject, the elements of $\vec{\Gamma}(t)$ ranged from 0.6 to 1.4, substantially out of its expected range of 0.95 to 1.05. This subject was excluded from further analysis, as this implies a large change in $S_0$ between its measurement and the start of the validation scan.

Figure 37C:
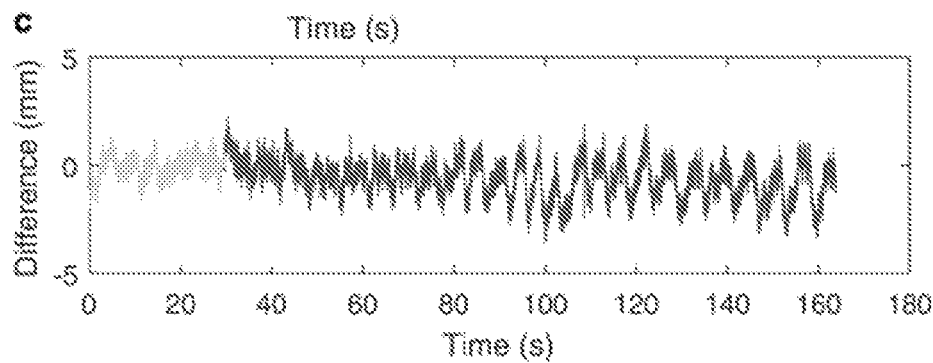
Figure 42:
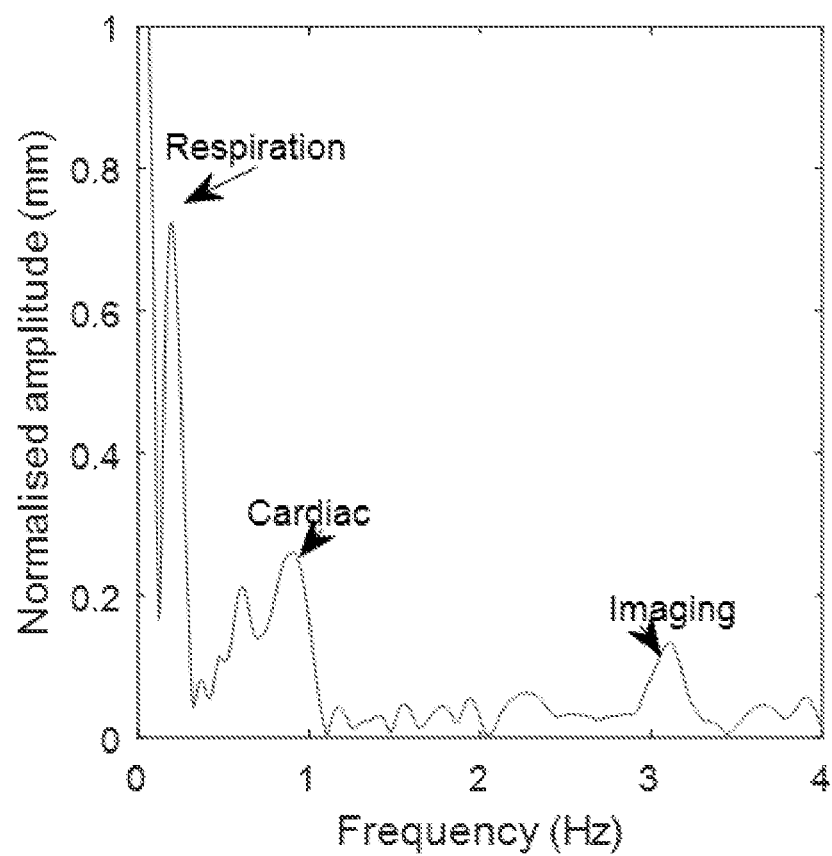
FIG. 42 is an exemplary frequency spectrum of the difference between diaphragm position and scatter scaled to amplitude, three frequency bands are labelled, respiration, cardiac, and imaging. The spectrum is the Fourier transform of the difference between the scatter measure and diaphragm position followed by an apodization of 0.15 Hz with a Hanning window and the amplitude is normalized to the width of the Hann window and frequency bin size. The average heart rate was 59 beats per minute in this subject. The unlabelled peak at 0 Hz is a constant offset, and the unlabelled peak at 0.6 Hz is expected to be the cross modulation of cardiac and respiration frequencies.

FIGS. 37A-37C compare the scattering-estimated diaphragm position with the MRI-measured position for one of the successful subjects. The difference between the two diaphragm positions show a small but systematic variation as a function of respiration. The frequency analysis from one of the six typical subjects is shown in FIG. 42. This shows three frequency bands: a respiratory band with an amplitude of 1.0±0.3 mm, a cardiac band with an amplitude of 0.4±0.1 mm, and a band at the imaging frequency (3.1 Hz) with an amplitude 010.1±0.1 mm.

Figure 38A:
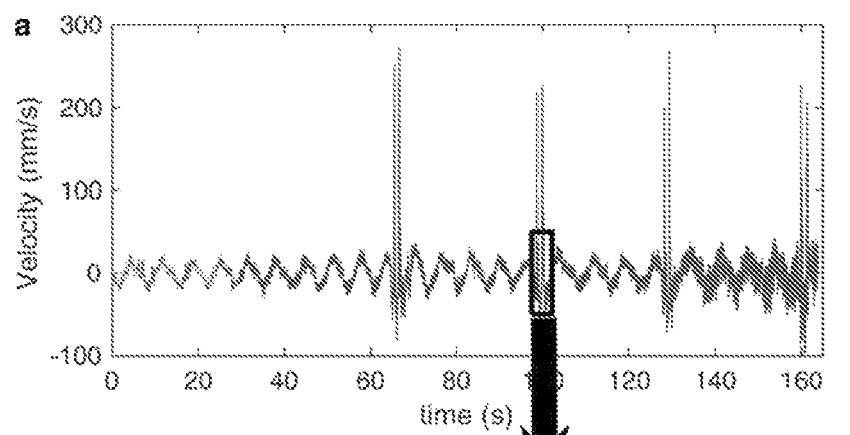
FIGS. 38A-38B show diaphragm velocity estimated from the diaphragm position estimates and MRI (FIG. 38A) with an excerpt (FIG. 38B) showing the fast response time of the scattering-based estimate when observing coughing (140 ms faster than the MRI measure).
Figure 38B:
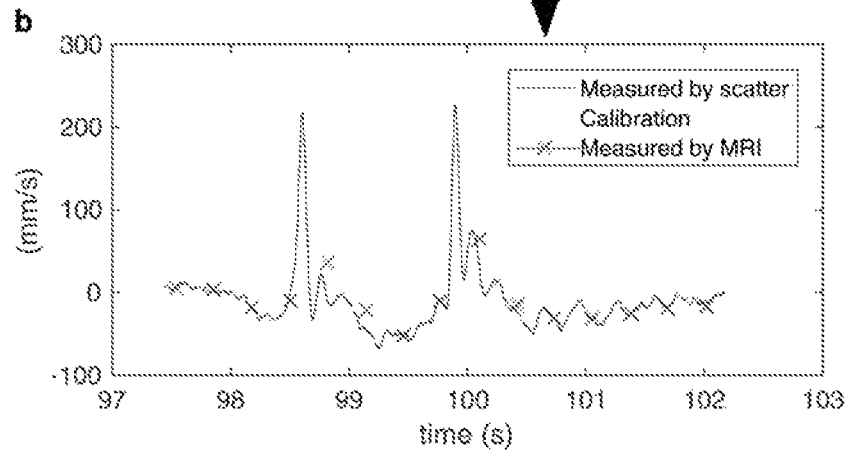

During the scan with deliberate coughing, the velocity estimated using both methods exceeded the standard range of ±25 mm/s for all four coughs. This plot of Kalman-filtered velocity is shown in FIGS. 38A and 38B.

Real-Time Pulse Sequence

Figures 39A, 39B:
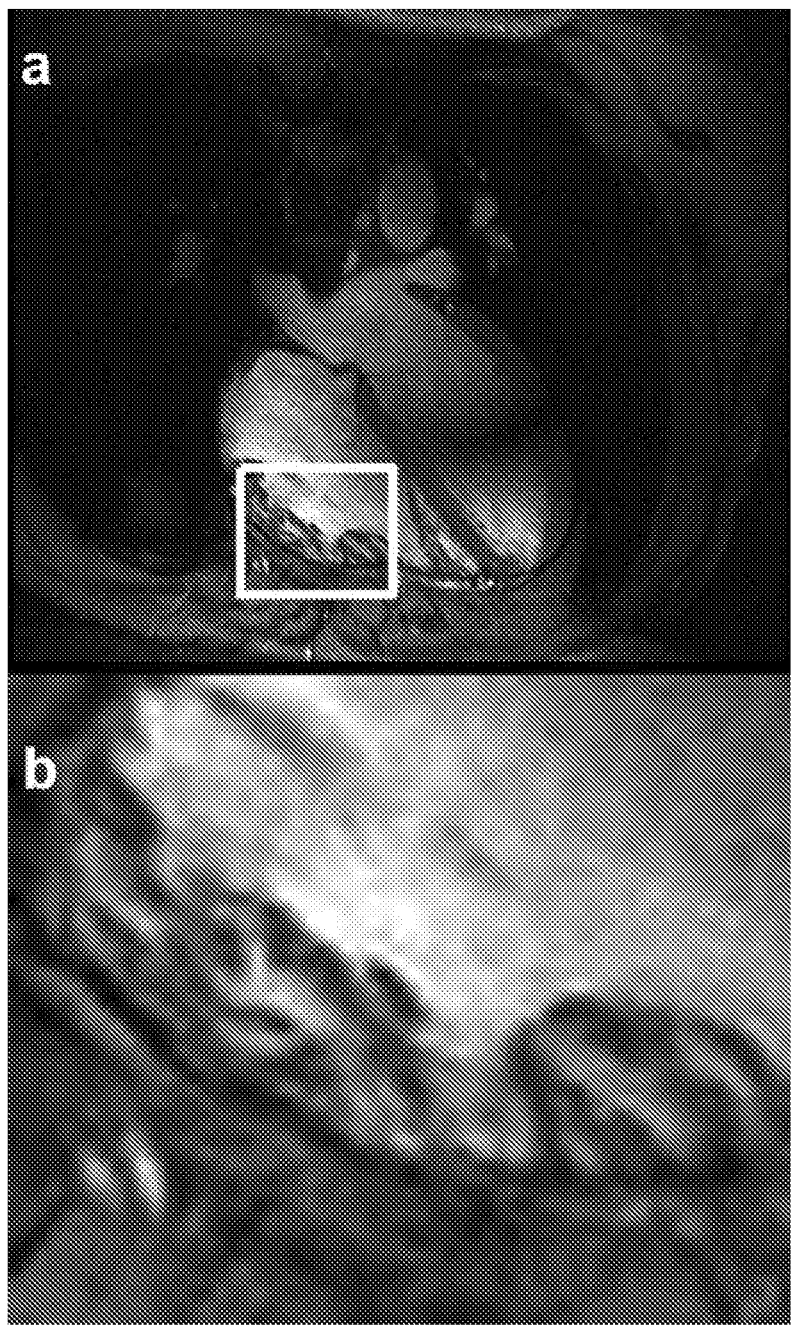
FIGS. 39A-39B demonstrate a single frame from a free-breathing gradient echo cine of the right side of the heart acquired and gated to end expiration using the new diaphragm position estimation (FIG. 39A.

FIGS. 39A and 39B show one frame of the cine scan and an enlarged insert, respectively; this scan presented no respiratory artefacts and has sharply defined trabeculations on the right ventricle.

Discussion

A method to estimate diaphragm position using DICO measures from an RF safety supervision system is shown. The root mean square error is smaller than the window size of a standard diaphragm navigator (1.4 mm compared with 5 mm) [99]. A frequency analysis found three dominant sources for the error: The greatest coincides with respiration, as would be expected, as scattering is sensitive to both the liver position and lungfilling volume, the latter of which may not be linear with diaphragm position. When used in practice as a source for binning or gating, the effect of diaphragm position error will be to shift the bin or gate boundary by a small amount depending on the size of the bin.

The error at the imaging frequency of 0.1 mm may be due to the system applying $B_0$ eddy current compensation through adjusting the system frequency. As a transmission line coil's scattering is a function of frequency, a change in the measurement frequency will result in a change in scattering. This would be consistent with observations that this error is linear with respect to the sampled line of k-space.

In one subject, $\vec{\Gamma}$ was out of its expected range; this can be because of a substantial change in $S_0$, which can be caused by the subject or coil moving between the measurement of $S_0$ and the validation scan, as a result of subject discomfort. Although the calibration was initially successful, there was a gradual increase in $d^{est}$. This can be attributed to the incorrect value of $S_0$ initially being compensated by the calibration, the calculation of $\vec{\Gamma}$ then being unable to correct for drift in $\vec{v}_{fwd}$.

The high-frequency, nonfiltered diaphragm measurement also lends itself to measuring diaphragm velocity, which has enabled the rapid detection of noncyclic events such as coughing. Practically, this can be used to inform the pulse sequence that such an event has occurred, and prospectively hold the progression of encoding steps until the episode is over. Diaphragm velocity can be used to detect end-inspiration and to separate the data acquired during inspiration from the data during expiration.

The advantage of using RF scattering over self-navigation methods [75] is that there is no requirement to use a radial encoding strategy or to include navigator readouts [77], which allow the operator to choose both the imaged slice and its encoding freely and presents improvements to existing methodology.

Some may be more familiar with noise covariance matrices in the context of a receiver array. Noise covariance, like scattering, is a function of impedance [80], [100]. One difference lies in the signal source: Noise covariance are measurements made of small thermally driven fluctuations (Johnson noise) and detected using a temporal correlation in a large set of measurements, whereas scattering measurements use external RF power and require a minimum number of N measurements to measure S(t), Additionally, the diagonal of a noise covariance matrix has no phase information and is only sensitive to changes in tissue conductivity and not permittivity [80].

In conclusion, demonstrated herein is a rapid, real-time, and quantitative method to estimate diaphragm position that uses the scattering of a transmit coil to provide an accurate measure of diaphragm position.

REFERENCES

[72] Paling M R, Brookeman J R. Respiration artifacts in MR imaging: reduction by breath holding. J Comput Assist Tomogr 1986; 10:1080-1082.

[73] Wang Y, Grimm R C, Rossman P J, Debbins J P, Riederer S J, Ehman R L. 3D coronary MR angiography in multiple breath-holds using a respiratory feedback monitor. Magn Reson Med 1995: 34:11-16.

[74] Wang Y, Rossman P J, Grimm R C, Riederer S J, Ehman R L. Navigator echo-based real-time respiratory gating and triggering for reduction of respiration effects in three-dimensional coronary MR angiography. Radiology 1996; 198:55-60.

[75] Feng L, Axel L, Chandarana H, Block K T, Sodickson D K, Otazo R. XD-GRASP: golden-angle radial MRI with reconstruction of extra motion-state dimensions using compressed sensing. Magri Reson Med 2016; 75:775-788.

[76] Ehman R L, McNamara M T, Pallack M, Hricak H, Higgins C B. Magnetic resonance imaging with respiratory gating: techniques and advantages. AJR Am J Roentgenol 1984; 143:1175-1182.

[77] Cheng J Y, Alley M T, Cunningham C H, Vasanawala S S, Pauly J M, Lustig M. Nonrigid motion correction in 3D using autofocusing with localized linear translations. Magn Reson Med 2012; 68; 1785-1797.

[78] Wang Y, Riederer S J, Ehman R L. Respiratory motion of the heart: kinematics and the implications for the spatial resolution in coronary imaging. Magn Reson Med 1995; 33:713-719.

[79] Santelli C, Nezafat R, Goddu B, Manning W J, Smink J, Kozerke S, Peters D C. Respiratory bellows revisited for motion compensation: preliminary experience for cardiovascular MR. Magn Reson Med 2011; 65:1097-1102.

[80] Andreychenko A, Raaijmakers A J E, Sbrizzi A, Crijns S P M, Lagendijk J J W, Luijten P R, van den Berg C A T. Thermal noise variance of a receive radiofrequency coil as a respiratory motion sensor. Magn Reson Med 2017; 77:221-228.

[81] Speier P, Fenchel M, Rehner R. PT-Nav: a novel respiratory navigation method for continuous acquisitions based on modulation of a pilot tone in the MR-receiver. In Proceedings from the European Society for Magnetic Resonance in Medicine and Biology, Edinburgh, United Kingdom, 2015. p. 128.

[82] Buikman D, Helzel T, R€oschmann P. The RF coil as a sensitive motion detector for magnetic resonance imaging. Magn Reson Imaging 1988; 6:281-289.

[83] Graesslin I, Stahl H, Nehrke K, Harvey P, Smink J, Mens G, Senn A, B€ornert P. An alternative concept for non-sequence interfering, contact-free respiration monitoring. In Proceedings of the 17$^{th}$ Annual meeting of ISMRM, Honolulu, Hi., USA, 2009. p. 753.

[84] Graesslin I, Mens G, Guillaume A, Stahl H, Koken P, Vernickel P, Harvey P, Smink J, Nehrke K, Boernert P. Advancements in contact-free respiration monitoring using RF pick-up coils. In Proceedings of the 18th Annual meeting of ISMRM, Stockholm, Sweden, 2010. p. 3045.

[85] Raaijmakers A J E, Italiaander M, Voogt I J, Luijten P R, Hoogduin J M, Klomp D W J, Van Den Berg C A T. The fractionated dipole antenna: a new antenna for body imaging at 7 T. Magn Reson Med 2016; 75:1366-1374.

[86] Snyder C J, Delabarre L, Moeller S, Tian J, Akgun C, Van de Moortele P-F, Bolan P J, Ugurbil K, Vaughan J T, Metzger G J. Comparison between eight- and sixteen-channel TEM transceive arrays for body imaging at 7T. Magn Reson Med 2012; 67:954-964.

[87] Russet P. Electromagnetics, microwave circuit and antenna design for communications engineering, 2nd ed. Norwood, Mass., USA: Artech House; 2006.

[88] Malmivuo J, Plonsey R. Bioelectromagnetism: principles and applications of bioelectric and biomagnetic fields. New York: Oxford University Press, USA; 1995.

[89] Zaj_iček R, Oppl L, Vrba J. Broadband measurement of complex permittivity using reflection method and coaxial probes. Radioengineering 2008; 17:14-19.

[90] Nopp P, Rapp E, Pfutzner H, et al. Dielectric properties of lung tissue as a function of air content. Phys Med Biol 1993; 38:699-716.

[91] Hess A T, Rodgers C T, Robson M D. Real-time diaphragm navigation using reflected power measurements from a multiple channel transmit RF coil on a human 7T. In Proceedings of the 24th Annual Meeting of ISMRM, Singapore, 2016. p. 1839.

[92] Adriany G, Van de Moortele P-F, Wiesinger F, et al. Transmit and receive transmission line arrays for 7 Tesla parallel imaging. Magn Reson Med 2005; 53:434-445.

[93] Snyder C J, Delabarre L, van de Moortele P-F, Snyder A L, Akgun C, Tian J, Metzger G J, Ugurbil K, Vaughan J T. Stripline/TEM transceiver array for 7T body imaging. In Proceedings of the 16th Annual Meeting of ISMRM, Berlin, Germany, 2007. p. 164.

[94] Snyder C, Vaughan J T, Lemaire C A. Remotely adjustable reactive and US008299681B2.

[95] Keith G A, Rodgers C T, Hess A T, Snyder C J, Vaughan J T, Robson M D. Automated tuning of an eight-channel cardiac transceive array at 7 Tesla using piezoelectric actuators. Magn Reson Med 2015; 73:2390-2397.

[96] Schmitter S, Wu X, Ugurbil K, Van De Moortele P F. Design of parallel transmission radiofrequency pulses robust against respiration in cardiac MRI at 7 Tesla. Magn Reson Med 2015; 74:1291-1305.

[97] Kalman R E. A new approach to linear filtering and prediction problems. J Basic Eng 1960; 82:35.

[98] Hess A T. van der Kouwe A J, Tisdall M D, Neubauer S, Robson M D. 2D diaphragm navigation with rapid gradient echo images: validation at 3T and application at 7T. In Proceedings of the 23rd Annual Meeting of ISMRM, Toronto, Ontario, Canada, 2015. p. 2565.

[99] Fischer R W, Botnar R M, Nehrke K, Boesiger P, Manning W J, Peters D C. Analysis of residual coronary artery motion for breath hold and navigator approaches using real-time coronary MRI. Magn Reson Med 2006; 55:612-618.

[100] Roemer P B, Edelstein W A, Hayes C E, Souza S P, Mueller O M. The NMR phased array. Magri Reson Med 1990; 16:192-225.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Therefore, at least the following is claimed:

1. A method for extraction of subject motion from multi-transmit electrical coupling in imaging of the subject, comprising:
   positioning a subject in association with a scanner, wherein the scanner has one or more transmit coils;
   starting one or more MR imaging pulse sequences with the scanner, wherein the one or more MR imaging pulse sequences comprise a plurality of RF pulses;
   collecting one or more S-matrix measurements over a period of time using the scanner, wherein the measurements are based on the reflected power of the plurality of RF pulses;
   performing a calibration on the one or more S-matrix measurements to determine a mixing vector and a constant;
   determining a reflection coefficient from the one or more calibrated S-matrix measurements;
   forming a measurement vector from the reflection coefficient;
   determining a position of an anatomical structure of the subject using the measuring vector, mixing vector, and constant; and
   outputting the determined position of the anatomical structure of the subject.

2. The method of claim 1, wherein starting one or more MR imaging pulse sequences further comprises diaphragm navigator imaging with the scanner.

3. The method of claim 1, wherein the plurality of RF pulses are part of a gradient echo (GRE) sequence, an inversion recovery sequence, or a balanced steady state free precession sequence, individually or in combination.

4. The method of claim 1, wherein the scanner has a plurality of transmit coils and the pulses are the same on each individual transmit coil of the plurality of transmit coils of the scanner.

5. The method of claim 1, wherein the scanner has a plurality of transmit coils and a pulse on at least one individual transmit coil of the plurality of transmit coils is different than the pulses on the other transmit coils of the plurality of transmit coils.

6. The method of claim 1, wherein the plurality of RF pulses are frequency multiplexed pulses, parallel transmit spokes, or parallel transmit spirals, individually or in combination.

7. The method of claim 1, wherein processing the split S-matrix measurements comprises demeaning, de-trending or filtering the split S-matrix measurements, individually or in combination.

8. The method of claim 1, wherein the scanner is a magnetic resonance (MR) scanner for MR imaging of a region of interest of the subject.

9. The method of claim 1, wherein the method is a computer-implemented method.

10. A method for extracting subject motion from multi-transmit electrical coupling in imaging of the subject, comprising:
   positioning a subject in association with a scanner, wherein the scanner has one or more transmit coils;
   activating one or more MR imaging pulses comprising a plurality of RF pulses;

collecting a plurality of S-matrix measurements over a period of time using the scanner to create a time series of S-matrix measurements, wherein the plurality of S-matrix measurements are based on the reflected power of the plurality of RF pulses;

splitting the time series of S-matrix measurements into real and imaginary components to form split S-matrix measurements;

processing the split S-matrix measurements;

extracting and identifying a raw cardiac signal of the subject from the processed split S-matrix measurements;

determining a mixing vector from the raw cardiac signal;

establishing a signal from the mixing vector;

analyzing the signal;

detecting features of a cardiac cycle from the analyzed signal; and correlating the detected cardiac cycle features with cardiac motion of the subject.

11. The method of claim 10, wherein the signal from the mixing vector is a scalar signal.

12. A system, comprising:
a magnetic resonance (MR) scanner including one or more transmit coils;
at least one computing device having a processor and a memory; and
at least one application executable in the at least one computing device stored in the memory that, when executed by the processor, the application causes the at least one computing device to:
start one or more MR imaging pulse sequences with the scanner, wherein the one or more MR imaging pulse sequences comprise a plurality of RF pulses;
collect one or more S-matrix measurements over a period of time using the scanner, wherein the measurements are based on the reflected power of the plurality of RF pulses;
perform a calibration on the one or more S-matrix measurements to determine a mixing vector and a constant;
determine a reflection coefficient from the one or more calibrated S-matrix measurements;
form a measurement vector from the reflection coefficient;
determine a position of an anatomical structure of the subject using the measuring vector, mixing vector, and constant; and
output the determined position of the anatomical structure of the subject.

13. The system of claim 12, wherein the application further causes the at least one or more computing devices to start diaphragm navigator imaging with the scanner.

14. The system of claim 12, wherein the plurality of RF pulses are part of a gradient echo (GRE) sequence, an inversion recovery sequence, or a balanced steady state free precession sequence, individually or in combination.

15. The system of claim 12, wherein the scanner has a plurality of transmit coils and the pulses are the same on each individual transmit coil of the plurality of transmit coils of the scanner.

16. The system of claim 12, wherein the scanner has a plurality of transmit coils and a pulse on at least one individual transmit coil of the plurality of transmit coils is different than the pulses on the other transmit coils of the plurality of transmit coils.

17. The system of claim 12, wherein the plurality of RF pulses are frequency multiplexed pulses, parallel transmit spokes, or parallel transmit spirals, individually or in combination.

18. The system of claim 12, wherein processing the split S-matrix measurements comprises demeaning, de-trending or filtering the split S-matrix measurements, individually or in combination.

* * * * *